(12) United States Patent
Kadoma et al.

(10) Patent No.: US 10,236,448 B2
(45) Date of Patent: Mar. 19, 2019

(54) BENZO[A] ANTHRACENE COMPOUND, LIGHT-EMITTING ELEMENT, DISPLAY DEVICE, ELECTRONIC DEVICE, AND LIGHTING DEVICE

(71) Applicant: Semiconductor Energy Laboratory Co., Ltd., Kanagawa-ken (JP)

(72) Inventors: Hiroshi Kadoma, Kanagawa (JP); Kaori Ogita, Kanagawa (JP); Tsunenori Suzuki, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 200 days.

(21) Appl. No.: 14/926,861

(22) Filed: Oct. 29, 2015

(65) Prior Publication Data

US 2016/0126463 A1 May 5, 2016

(30) Foreign Application Priority Data

Oct. 31, 2014 (JP) .................................. 2014-222441

(51) Int. Cl.
*H01L 51/00* (2006.01)
*C09K 11/06* (2006.01)
(Continued)

(52) U.S. Cl.
CPC ........ *H01L 51/0054* (2013.01); *C07D 209/86* (2013.01); *C09K 11/06* (2013.01);
(Continued)

(58) Field of Classification Search
None
See application file for complete search history.

(56) References Cited

U.S. PATENT DOCUMENTS 8,771,840 B2 7/2014 Suzuki et al.
2007/0224447 A1 9/2007 Sotoyama et al.
(Continued)

FOREIGN PATENT DOCUMENTS

CN 101445422 6/2009
CN 103187531 A * 7/2013
(Continued)

OTHER PUBLICATIONS

Derwent English abstract for CN 101445422 A (2009).*
(Continued)

*Primary Examiner* — Sin J Lee
(74) *Attorney, Agent, or Firm* — Husch Blackwell LLP

(57) ABSTRACT

Provided is a light-emitting element with high emission efficiency including a fluorescent material as a light-emitting substance. In a light-emitting element including a pair of electrodes and an EL layer between the pair of electrodes, a delayed fluorescence component due to triplet-triplet annihilation accounts for 20% or more of light emitted from the EL layer, and the light has at least one emission spectrum peak in the blue wavelength range. The EL layer includes an organic compound in which an energy difference between the lowest singlet excited energy level and the lowest triplet excited energy level is 0.5 eV or more. The EL layer includes a benzo[a]anthracene compound.

15 Claims, 23 Drawing Sheets

(51) Int. Cl.
*C07D 209/86* (2006.01)
*H01L 51/50* (2006.01)
*H01L 27/32* (2006.01)

(52) U.S. Cl.
CPC .. *H01L 51/0072* (2013.01); *C09K 2211/1007* (2013.01); *C09K 2211/1011* (2013.01); *C09K 2211/1014* (2013.01); *C09K 2211/1029* (2013.01); *H01L 27/3209* (2013.01); *H01L 51/006* (2013.01); *H01L 51/0058* (2013.01); *H01L 51/504* (2013.01); *H01L 51/5012* (2013.01); *H01L 51/5016* (2013.01); *H01L 51/5028* (2013.01); *H01L 2251/5376* (2013.01)

(56) References Cited

U.S. PATENT DOCUMENTS

| | | |
|---|---|---|
| 2007/0247063 A1 | 10/2007 | Murase et al. |
| 2010/0069647 A1 | 3/2010 | Suzuki et al. |
| 2010/0301318 A1 | 12/2010 | Kuma et al. |
| 2011/0233604 A1 | 9/2011 | Ikeda |
| 2012/0126205 A1 | 5/2012 | Kawamura et al. |
| 2012/0126208 A1 | 5/2012 | Kawamura et al. |
| 2012/0126209 A1 | 5/2012 | Kawamura et al. |
| 2012/0153268 A1 | 6/2012 | Kawamura et al. |
| 2014/0296538 A1 | 10/2014 | Suzuki et al. |
| 2014/0339522 A1 | 11/2014 | Nonaka et al. |
| 2016/0104847 A1* | 4/2016 | Xia .................. H01L 51/0052 257/40 |

FOREIGN PATENT DOCUMENTS

| | | | |
|---|---|---|---|
| KR | 2011103819 A | * | 9/2011 |
| KR | 10-2012-0038422 | | 4/2012 |

OTHER PUBLICATIONS

Chemical Abstract (Accession No. 2011:1211918)—English abstract for KR 2011103819 A (2011).*
Derwent English abstract for CN 103187531 A (2013).*
Machine-assisted English translation for KR 2011103819 A (Kim et al). (Year: 2011).*
Kondakov, D.Y. et al., "Triplet Annihilation Exceeding Spin Statistical Limit in Highly Efficient Fluorescent Organic Light-Emitting Diodes," Journal of Applied Physics, vol. 106, No. 12, Dec. 15, 2009, pp. 124510-1-124510-7.
Suzuki, T. et al., "Highly Efficient Long-Life Blue Fluorescent Organic Light-Emitting Diode Exhibiting Triplet-Triplet Annihilation Effects Enhanced by a Novel Hole-Transporting Material," Japanese Journal of Applied Physics, vol. 53, Jan. 1, 2014, pp. 052102-1-052102-6.

* cited by examiner

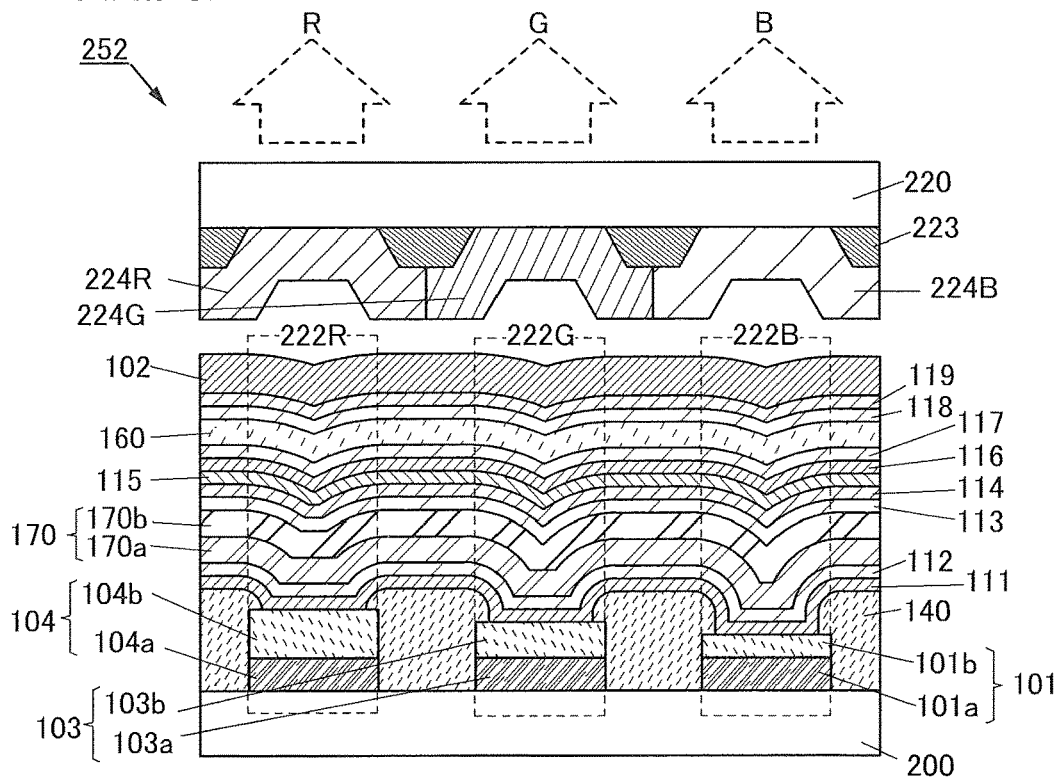
FIG. 5A
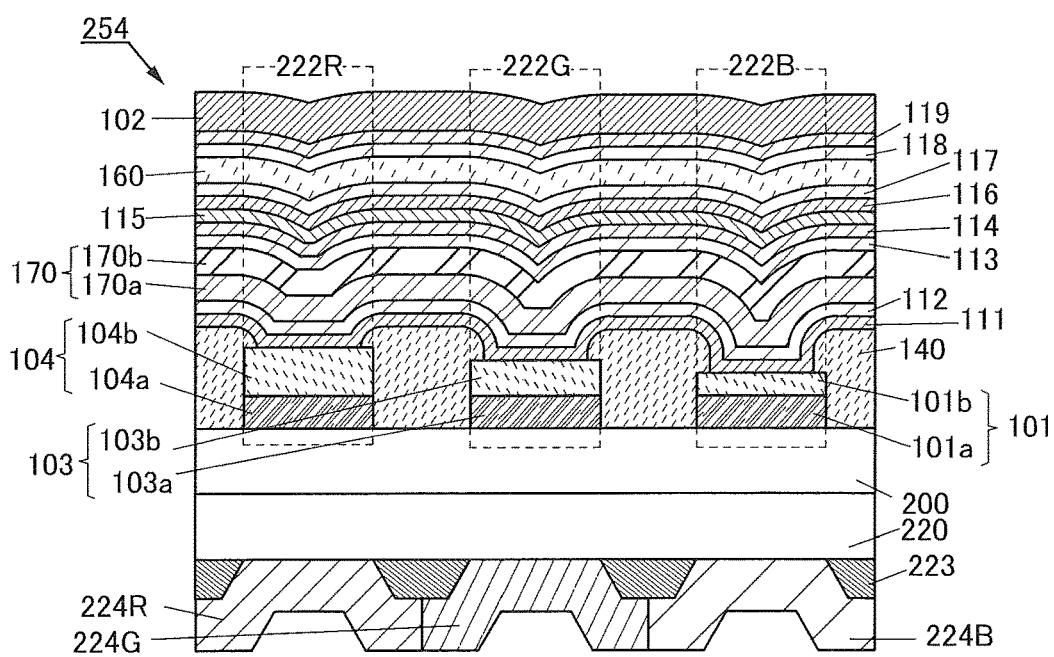
FIG. 5B
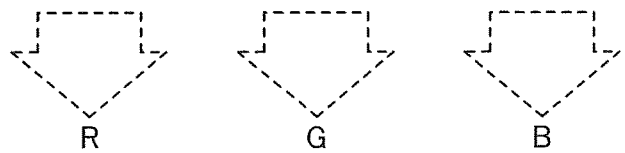

BENZO[A] ANTHRACENE COMPOUND, LIGHT-EMITTING ELEMENT, DISPLAY DEVICE, ELECTRONIC DEVICE, AND LIGHTING DEVICE

BACKGROUND OF THE INVENTION

1. Field of the Invention

One embodiment of the present invention relates to a benzo[a]anthracene compound. One embodiment of the present invention relates to a light-emitting element in which a light-emitting layer capable of providing light emission by application of an electric field is provided between a pair of electrodes, and also relates to a display device, an electronic device, and a lighting device including the light-emitting element.

Note that one embodiment of the present invention is not limited to the above technical field. The technical field of one embodiment of the invention disclosed in this specification and the like relates to an object, a method, or a manufacturing method. In addition, one embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting device, a lighting device, a power storage device, a storage device, a method of driving any of them, and a method of manufacturing any of them.

2. Description of the Related Art

In recent years, research and development have been extensively conducted on light-emitting elements using electroluminescence (EL). In a basic structure of such a light-emitting element, a layer containing a light-emitting material (an EL layer) is interposed between a pair of electrodes. By application of a voltage between the electrodes of this element, light emission from the light-emitting material can be obtained.

Since the above light-emitting element is a self-luminous type, a display device using this light-emitting element has advantages such as high visibility, no necessity of a backlight, and low power consumption. Furthermore, such a light-emitting element also has advantages in that the element can be manufactured to be thin and lightweight, and has high response speed.

In the case of a light-emitting element (e.g., an organic EL element) whose EL layer contains an organic material as a light-emitting material and is provided between a pair of electrodes, application of a voltage between the pair of electrodes causes injection of electrons from a cathode and holes from an anode into the EL layer having a light-emitting property and thus a current flows. By recombination of the injected electrons and holes, the light-emitting organic material is brought into an excited state to provide light emission.

Note that an excited state formed by an organic material can be a singlet excited state (S*) or a triplet excited state (T*). Light emission from the singlet-excited state is referred to as fluorescence, and light emission from the triplet excited state is referred to as phosphorescence. The formation ratio of S* to T* in the light-emitting element is statistically considered to be 1:3. In other words, a light-emitting element including a phosphorescent material has higher emission efficiency than a light-emitting element containing a fluorescent material. Therefore, light-emitting elements including phosphorescent materials capable of converting a triplet excited state into light emission has been actively developed in recent years.

Among light-emitting elements including phosphorescent materials, a light-emitting element that emits blue light in particular has yet been put into practical use because it is difficult to develop a stable material having a high triplet excited energy level. For this reason, the development of a more stable fluorescent material for a light-emitting element that emits blue light has been conducted and a technique for increasing the emission efficiency of such a light-emitting element has been searched.

As an emission mechanism capable of converting part of a triplet excited state into light emission, triplet-triplet annihilation (TTA) is known. The term TTA refers to a process in which, when two triplet excitons approach each other, excited energy is transferred and spin angular momentum are exchanged to form a singlet exciton.

As compounds in which TTA occurs, anthracene compounds are known. Non-Patent Document 1 discloses that the use of an anthracene compound as a host material in a light-emitting element that emits blue light achieves an external quantum efficiency exceeding 10%. It also discloses that the proportion of the delayed fluorescence component due to TTA in the anthracene compound is approximately 10% of emissive components of the light-emitting element.

Furthermore, tetracene compounds are known as compounds in which a delayed fluorescence component due to TTA accounts for a large proportion. Non-Patent Document 2 discloses that the delayed fluorescence component due to TTA in light emitted from a tetracene compound accounts for a larger proportion than that for an anthracene compound.

REFERENCES

Non-Patent Documents

Non-Patent Document 1: Tsunenori Suzuki and six others, Japanese Journal of Applied Physics, Vol. 53, 052102 (2014)

Non-Patent Document 2: D. Y. Kondakov and three others, Journal of Applied Physics, Vol. 106, 124510 (2009)

SUMMARY OF THE INVENTION

What is important in increasing the emission efficiency of a light-emitting element including a fluorescent material is to convert energy of triplet excitons, which do not contribute to light emission, into energy of singlet excitons, which have a light-emitting property, with high conversion efficiency; i.e., conversion of triplet exciton energy into singlet exciton energy by TTA is important. To achieve this, an increase in the proportion of a delayed fluorescence component due to TTA in emissive components of a light-emitting element is especially important. This is because an increased proportion of a delayed fluorescence component due to TTA means that singlet excitons having a light-emitting property are formed in a higher ratio.

Tetracene compounds, which are known as compounds in which a delayed fluorescence component due to TTA accounts for a large proportion, have lower excited energy than anthracene compounds and emit yellow light or light with a longer wavelength than yellow light. Therefore, tetracene compounds are difficult to use as a host material in a light-emitting element that emits blue light. To increase the emission efficiency of a light-emitting element that emits blue light, a compound which has high excited energy and in which a delayed fluorescence component due to TTA accounts for a large proportion is needed.

In view of the above, an object of one embodiment of the present invention is to provide a light-emitting element that has high emission efficiency and includes a fluorescent material. Another object of one embodiment of the present invention is to provide a light-emitting element that emits blue light with high emission efficiency. Another object of one embodiment of the present invention is to provide a compound in which a delayed fluorescence component due to TTA accounts for a large proportion of emissive components. Another object of one embodiment of the present invention is to provide a light-emitting element in which a delayed fluorescence component due to TTA accounts for a large proportion of emissive components. Another object of one embodiment of the present invention is to provide a novel compound. Another object of one embodiment of the present invention is to provide a light-emitting element including a novel compound. Another object of one embodiment of the present invention is to provide a novel light-emitting device with high emission efficiency and low power consumption. Another object of one embodiment of the present invention is to provide a novel display device.

Note that the description of the above object does not preclude the existence of other objects. In one embodiment of the present invention, there is no need to achieve all the objects. Objects other than the above objects will be apparent from and can be derived from the description of the specification and the like.

In one embodiment of the present invention, the emission efficiency of a light-emitting element at least including an EL layer is improved in such a manner that TTA is efficiently caused in the EL layer to convert triplet excitons which do not contribute to light emission into singlet excitons and then light is emitted from the singlet excitons or light is emitted from a guest material (a fluorescent dopant) via energy transfer.

What is important in causing TTA in the EL layer efficiently is the use of, as a host material, a compound in which a delayed fluorescence component due to TTA accounts for a large proportion of emissive components. Particularly in a light-emitting element that emits blue light, the use of a compound with high excited energy as a host material is important.

One embodiment of the present invention is a light-emitting element including a pair of electrodes and an EL layer between the pair of electrodes. A delayed fluorescence component due to triplet-triplet annihilation accounts for 20% or more of light emitted from the EL layer, and the light has at least one emission spectrum peak in a blue wavelength range.

One embodiment of the present invention is a light-emitting element including a pair of electrodes and an EL layer between the pair of electrodes. A delayed fluorescence component due to triplet-triplet annihilation accounts for 20% or more of light emitted from the EL layer, and the light has at least one emission spectrum peak at a wavelength greater than or equal to 400 nm and less than or equal to 550 nm.

One embodiment of the present invention is a light-emitting element including a pair of electrodes and an EL layer between the pair of electrodes. The EL layer includes an organic compound in which an energy difference between a lowest singlet excited energy level and a lowest triplet excited energy level is 0.5 eV or more. A delayed fluorescence component accounts for 20% or more of light emitted from the EL layer, and the light has at least one emission spectrum peak in a blue wavelength range.

One embodiment of the present invention is a light-emitting element including a pair of electrodes and an EL layer between the pair of electrodes. The EL layer includes an organic compound in which an energy difference between a lowest singlet excited energy level and a lowest triplet excited energy level is 0.5 eV or more. A delayed fluorescence component accounts for 20% or more of light emitted from the EL layer, and the light has at least one emission spectrum peak at a wavelength greater than or equal to 400 nm and less than or equal to 550 nm.

In each of the above structures, a difference in equivalent energy value between a peak wavelength of a fluorescence spectrum and a peak wavelength of a phosphorescence spectrum of the organic compound is preferably 0.5 eV or more.

One embodiment of the present invention is a light-emitting element including a pair of electrodes and an EL layer between the pair of electrodes. The EL layer includes a compound having a benzo[a]anthracene skeleton, and a delayed fluorescence component accounts for 20% or more of light emitted from the EL layer.

In each of the above structures, the EL layer preferably includes a guest material capable of emitting fluorescence.

In each of the above structures, the guest material preferably includes a pyrene skeleton.

Another embodiment of the present invention is a benzo[a]anthracene compound represented by a general formula (G1).

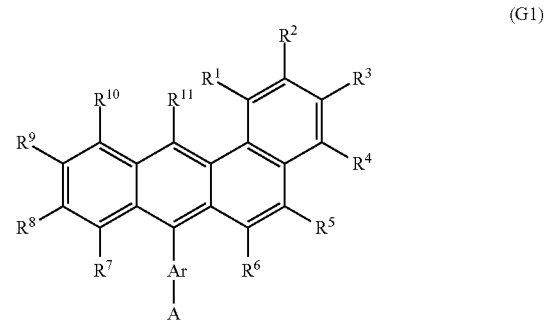

(G1)

In the general formula (G1), A represents a substituted or unsubstituted carbazolyl group, $R^1$ to $R^{10}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms, $R^{11}$ represents any of hydrogen, an alkyl group having 1 to 6 carbon atoms, a cycloalkyl group having 3 to 6 carbon atoms, and a substituted or unsubstituted phenyl group, and Ar represents an arylene group having 6 to 13 carbon atoms. The arylene group may include one or more substituents and the substituents may be bonded to each other to form a ring.

Another embodiment of the present invention is a benzo[a]anthracene compound represented by a general formula (G2).

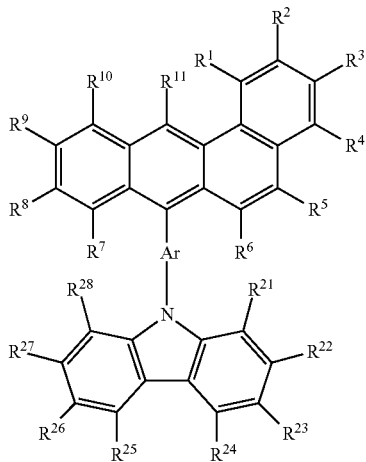

(G2)

In the general formula (G2), $R^1$ to $R^{10}$ and $R^{21}$ to $R^{28}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms, $R^{11}$ represents any of hydrogen, an alkyl group having 1 to 6 carbon atoms, a cycloalkyl group having 3 to 6 carbon atoms, and a substituted or unsubstituted phenyl group, and Ar represents an arylene group having 6 to 13 carbon atoms. The arylene group may include one or more substituents and the substituents may be bonded to each other to form a ring.

Another embodiment of the present invention is a benzo[a]anthracene compound represented by a general formula (G3).

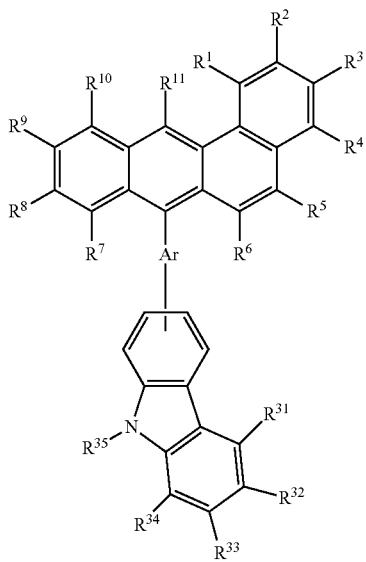

(G3)

In the general formula (G3), $R^1$ to $R^{10}$ and $R^{31}$ to $R^{35}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms, $R^{11}$ represents any of hydrogen, an alkyl group having 1 to 6 carbon atoms, a cycloalkyl group having 3 to 6 carbon atoms, and a substituted or unsubstituted phenyl group, and Ar represents an arylene group having 6 to 13 carbon atoms. The arylene group may include one or more substituents and the substituents may be bonded to each other to form a ring.

In the benzo[a]anthracene compound having any of the above structures, Ar is preferably any of a substituted or unsubstituted phenylene group and a substituted or unsubstituted biphenyldiyl group.

In the benzo[a]anthracene compound having any of the above structures, Ar is preferably a substituted or unsubstituted phenylene group.

In the benzo[a]anthracene compound having any of the above structures, Ar is preferably a substituted or unsubstituted m-phenylene group.

Another embodiment of the present invention is a benzo[a]anthracene compound represented by a general formula (G4).

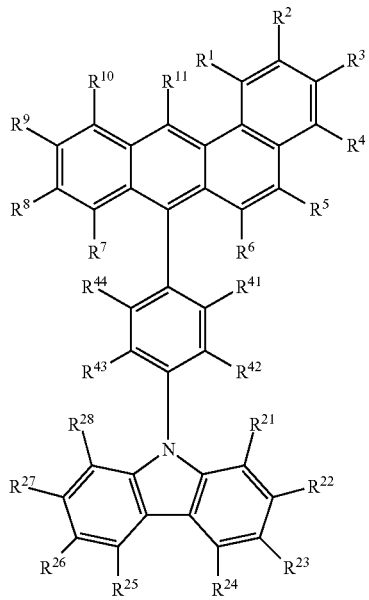

(G4)

In the general formula (G4), $R^1$ to $R^{10}$, $R^{21}$ to $R^{28}$, and $R^{41}$ to $R^{44}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms, and $R^{11}$ represents any of hydrogen, an alkyl group having 1 to 6 carbon atoms, a cycloalkyl group having 3 to 6 carbon atoms, and a substituted or unsubstituted phenyl group.

Another embodiment of the present invention is a benzo[a]anthracene compound represented by a general formula (G5).

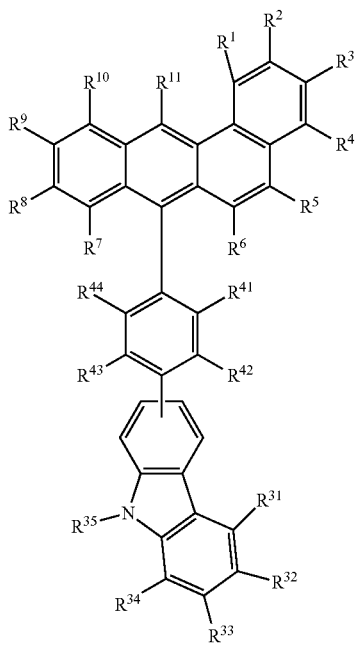

(G5)

In the general formula (G5), $R^1$ to $R^{10}$, $R^{31}$ to $R^{35}$, and $R^{41}$ to $R^{44}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms, and $R^{11}$ represents any of hydrogen, an alkyl group having 1 to 6 carbon atoms, a cycloalkyl group having 3 to 6 carbon atoms, and a substituted or unsubstituted phenyl group.

Another embodiment of the present invention is a benzo[a]anthracene compound represented by a structure formula (100).

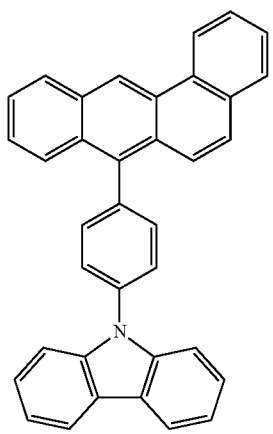

(100)

Another embodiment of the present invention is a light-emitting element including a pair of electrodes and an EL layer between the pair of electrodes. The EL layer includes a benzo[a]anthracene compound described in any of the above structures.

Another embodiment of the present invention is a light-emitting element including a pair of electrodes and an EL layer between the pair of electrodes. The EL layer includes a benzo[a]anthracene compound described in any of the above structures, and a delayed fluorescence component accounts for 20% or more of light emitted from the EL layer.

In each of the above structures, the EL layer preferably includes a guest material capable of emitting fluorescence.

In each of the above structures, the guest material preferably has a function of exhibiting an emission spectrum peak in a blue wavelength range.

In each of the above structures, the guest material is preferably capable of emitting delayed fluorescence.

In each of the above structures, the guest material preferably includes a pyrene skeleton.

Another embodiment of the present invention is a display device including the light-emitting element with any of the above structures, a color filter, a seal, or a transistor. Another embodiment of the present invention is an electronic device including the display device and a housing or a touch sensor. Another embodiment of the present invention is a lighting device including the light-emitting element with any of the above-described structures and a housing or a touch sensor. The category of one embodiment of the present invention includes not only the light-emitting device including the light-emitting element but also an electronic device including the light-emitting device. Thus, a light-emitting device in this specification means an image display device or a light source (including a lighting device). The light-emitting device may be included in a module in which a connector such as a flexible printed circuit (FPC) or a tape carrier package (TCP) is connected to a light-emitting device, a module in which a printed wiring board is provided on the tip of a TCP, or a module in which an integrated circuit (IC) is directly mounted on a light-emitting element by a chip on glass (COG) method.

According to one embodiment of the present invention, a light-emitting element that has high emission efficiency and includes a fluorescent material can be provided. According to one embodiment of the present invention, a light-emitting element that emits blue light with high emission efficiency can be provided. According to one embodiment of the present invention, a compound in which a delayed fluorescence component due to TTA accounts for a large proportion of emissive components can be provided. According to one embodiment of the present invention, a light-emitting element in which a delayed fluorescence component due to TTA accounts for a large proportion of emissive components can be provided. According to one embodiment of the present invention, a novel compound can be provided. According to one embodiment of the present invention, a light-emitting element including a novel compound can be provided. According to one embodiment of the present invention, a novel light-emitting device with high emission efficiency and low power consumption can be provided. According to one embodiment of the present invention, a novel display device can be provided.

Note that the description of these effects does not preclude the existence of other effects. One embodiment of the present invention does not necessarily achieve all the effects listed above. Other effects will be apparent from and can be derived from the description of the specification, the drawings, the claims, and the like.

BRIEF DESCRIPTION OF THE DRAWINGS

In the accompanying drawings:

FIGS. 5A and 5B are each a schematic cross-sectional view of a light-emitting element according to one embodiment of the present invention;

DETAILED DESCRIPTION OF THE INVENTION

Figure 1A:
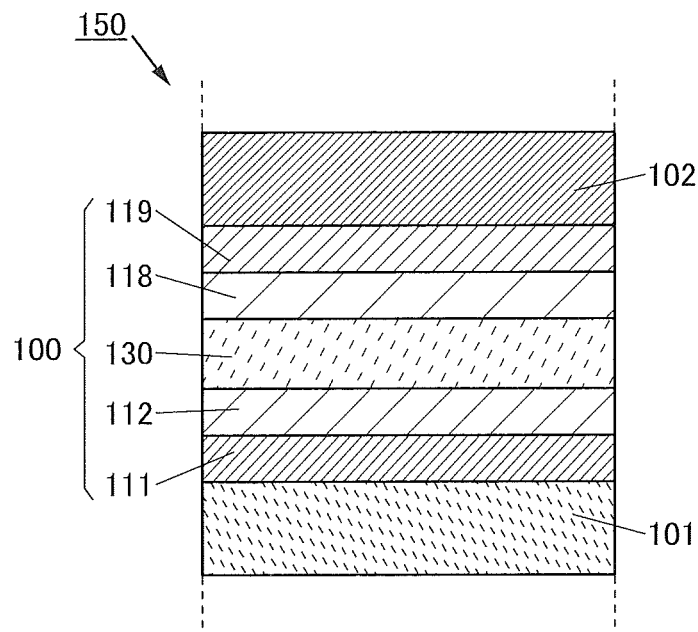
FIGS. 1A and 1B are schematic cross-sectionals views of a light-emitting element according to one embodiment of the present invention and FIG. 1C is a schematic diagram illustrating the correlation of energy levels.

Embodiments of the present invention will be explained below with reference to the drawings. However, the present invention is not limited to description to be given below, and it is to be easily understood that modes and details thereof can be variously modified without departing from the purpose and the scope of the present invention. Accordingly, the present invention should not be interpreted as being limited to the content of the embodiments below.

Note that the position, the size, the range, or the like of each structure illustrated in drawings and the like is not accurately represented in some cases for simplification. Therefore, the disclosed invention is not necessarily limited to the position, the size, the range, or the like disclosed in the drawings and the like.

Note that the ordinal numbers such as "first", "second", and the like in this specification and the like are used for convenience and do not denote the order of steps or the stacking order of layers. Therefore, for example, description can be made even when "first" is replaced with "second" or "third", as appropriate. In addition, the ordinal numbers in this specification and the like are not necessarily the same as those which specify one embodiment of the present invention.

In the description of modes of the present invention in this specification and the like with reference to the drawings, the same components in different diagrams are commonly denoted by the same reference numeral in some cases.

In this specification and the like, the terms "film" and "layer" can be interchanged with each other depending on the case or circumstances. For example, the term "conductive layer" can be changed into the term "conductive film" in some cases. Also, the term "insulating film" can be changed into the term "insulating layer" in some cases.

In this specification and the like, a singlet excited state (S*) means a singlet state having excited energy. Among singlet excited states, an excited state having the lowest energy is referred to as the lowest singlet excited state. Furthermore, a singlet excited energy level means an energy level in a singlet excited state. Among singlet excited energy levels, the lowest excited energy level is referred to as the lowest singlet excited energy ($S_1$) level. Note that in this specification and the like, simple expressions "singlet excited state" and "singlet excited energy level" mean the lowest singlet excited state and the $S_1$ level, respectively, in some cases.

In this specification and the like, a triplet excited state (T*) means a triplet state having excited energy. Among triplet excited states, an excited state having the lowest energy is referred to as the lowest triplet excited state. Furthermore, a triplet excited energy level means an energy level in a triplet excited state. Among triplet excited energy levels, the lowest excited energy level is referred to as the lowest triplet excited energy ($T_1$) level. Note that in this specification and the like, simple expressions "triplet excited state" and "triplet excited energy level" mean the lowest triplet excited state and the $T_1$ level, respectively, in some cases.

In this specification and the like, a fluorescent material refers to a material that emits light in the visible light region when the singlet excited state relaxes to the ground state. A phosphorescent material refers to a material that emits light in the visible light region at room temperature when the triplet excited state relaxes to the ground state. That is, a phosphorescent material refers to a material that can convert triplet excited energy into visible light.

Note that in this specification and the like, room temperature refers to a temperature in the range from 0° C. to 40° C.

In this specification and the like, the blue wavelength range refers to a range in which the wavelength is greater than or equal to 400 nm and less than or equal to 550 urn, and the blue light emission refers to light emission with at least one emission spectrum peak in the range.

Embodiment 1

In this embodiment, a light-emitting element of one embodiment of the present invention will be described below with reference to FIGS. 1A and 1B and FIGS. 2A to 2C.

Structure Example of Light-Emitting Element

First, a structure of a light-emitting element of one embodiment of the present invention is described below with reference to FIGS. 1A to 1C.

FIG. 1A is a schematic cross-sectional view of a light-emitting element 150 of one embodiment of the present invention.

The light-emitting element 150 includes an EL layer 100 between a pair of electrodes (an electrode 101 and an electrode 102). The EL layer 100 includes at least a light-emitting layer 130. Note that in this embodiment, although description is given assuming that the electrode 101 and the electrode 102 of the pair of electrodes serve as an anode and a cathode, respectively, they can be interchanged for the structure of the light-emitting element 150.

The EL layer 100 illustrated in FIG. 1A includes a functional layer in addition to the light-emitting layer 130. The functional layer includes a hole-injection layer 111, a hole-transport layer 112, an electron-transport layer 118, and an electron-injection layer 119. Note that the structure of the EL layer 100 is not limited to the structure illustrated in FIG. 1A, and a structure may be employed in which at least one selected from the hole-injection layer 111, the hole-transport layer 112, the electron-transport layer 118, and the electron-injection layer 119 is included. Alternatively, the EL layer 100 may include a functional layer which is capable of lowering a hole injection barrier or an electron injection barrier, improving a hole-transport property or an electron-transport property, inhibiting a hole-transport property or an electron-transport property, or suppressing a quenching phenomenon by an electrode, for example.

Figure 1B:
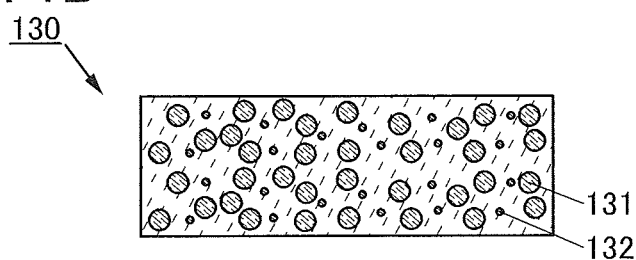

FIG. 1B is a schematic cross-sectional view of an example of the light-emitting layer 130 in FIG. 1A. The light-emitting layer 130 in FIG. 1B includes at least a host material 131 and a guest material 132.

The host material 131 preferably has a function of converting triplet excited energy into singlet excited energy by causing TTA, so that the triplet excited energy generated in the light-emitting layer 130 can be partly converted into singlet excited energy by TTA in the host material 131. The singlet excited energy generated by TTA can be transferred to the guest material 132 and extracted as phosphorescence. In order to achieve this, the lowest singlet excited energy ($S_1$) level of the host material 131 is preferably higher than the $S_1$ level of the guest material 132. In addition, the lowest triplet excited energy ($T_1$) level of the host material 131 is preferably lower than the $T_1$ level of the guest material 132.

Note that the host material 131 may be composed of a single compound or a plurality of compounds. The guest material 132 may be a light-emitting organic material, and the light-emitting organic material is preferably a material capable of emitting fluorescence (hereinafter also referred to as a fluorescent material). A fluorescent material is used as the guest material 132. Note that the guest material 132 may be read as the fluorescent material.

<Emission Mechanism of Light-Emitting Element>

First, an emission mechanism of the light-emitting element 150 is described below.

In the light-emitting element 150 of one embodiment of the present invention, voltage application between a pair of electrodes (electrodes 101 and 102) causes electrons and holes to be injected from the cathode and the anode, respectively, into the EL layer 100 and current flows. By recombination of the injected electrons and holes, excitons are formed. The ratio of singlet excitons to triplet excitons in the excitons formed by the carrier recombination is 1:3 according to the statistically obtained probability. Therefore, the probability of formation of singlet excitons is 25%.

Note that the term "exciton" refers to a pair of carriers (an electron and a hole). Since an exciton has excited energy, a material where an exciton is formed is brought into an excited state.

Through two processes described below, singlet excitons are formed in the EL layer 100 and light emission from the guest material 132 can be obtained. The processes are (α) direct formation process and (β) TTA process.

<<(α) Direct Formation Process>>

The case where carriers (electrons and holes) recombine in the light-emitting layer 130 included in the EL layer 100 to form a singlet exciton is first described.

When the carriers recombine in the host material 131, excitons are formed to bring the host material 131 into an excited state (a singlet excited state or a triplet excited state). At this time, in the case where the excited state of the host material 131 is a singlet excited state, singlet excited energy transfers from the $S_1$ level of the host material 131 to the $S_1$ level of the guest material 132, thereby forming the singlet excited state of the guest material 132. Note that the case where the excited state of the host material 131 is a triplet excited state is described in later in (β) TTA process.

When the carriers recombine in the guest material 132, excitons are formed to bring the guest material 132 into an excited state (a singlet excited state or a triplet excited state).

In the case where the formed excited state of the guest material 132 is a singlet excited state, light emission is obtained from the singlet excited state of the guest material 132. To obtain high emission efficiency in this case, the fluorescence quantum yield of the guest material 132 is preferably high.

In the case where the formed excited state of the guest material 132 is a triplet excited state, the triplet excited state of the guest material 132 is thermally deactivated and does not contribute to light emission because the guest material 132 is a fluorescent material. However, if the $T_1$ level of the host material 131 is lower than the $T_1$ level of the guest material 132, the triplet excited energy of the guest material 132 can be transferred from the $T_1$ level of the guest material 132 to the $T_1$ level of the host material 131. In this case, the triplet excited energy can be converted into singlet excited energy by (β) TTA process described later.

In the case where the $T_1$ level of the host material 131 is higher than the $T_1$ level of the guest material 132, if the weight ratio of the guest material 132 to the host material 131 is low, the probability of carrier recombination in the guest material 132 can be reduced. In addition, the probability of energy transfer from the $T_1$ level of the host material 131 to the $T_1$ level of the guest material 132 can be reduced. Specifically, the weight ratio of the guest material 132 to the host material 131 is preferably greater than 0 and less than or equal to 0.05.

<<(β) TTA Process>>

The case where a singlet exciton is formed from triplet excitons formed in the carrier recombination process in the light-emitting layer 130 is described.

Here, the case where the $T_1$ level of the host material 131 is lower than the $T_1$ level of the guest material 132 is described. The correlation of energy levels in this case is schematically shown in FIG. 1C. What terms and signs in FIG. 1C represent are listed below. Note that the $T_1$ level of the host material 131 may be higher than the $T_1$ level of the guest material 132.

Host (131): the host material 131
Guest (132): the guest material 132 (fluorescent material)
$S_{FH}$: the $S_1$ level of the host material 131
$T_{FH}$: the $T_1$ level of the host material 131
$S_{FG}$: the $S_1$ level of the guest material 132 (fluorescent material)
$T_{FG}$: the $T_1$ level of the guest material 132 (fluorescent material)

Carriers recombine in the host material 131 and excitons are formed to bring the host material 131 into an excited state. At this time, in the case where the formed excitons are triplet excitons and two of the formed triplet excitons approach each other, a reaction in which one of them is converted into a singlet exciton having energy of the $S_1$ level ($S_{FH}$) of the host material 131 might be caused (see TTA in FIG. 1C). This is represented by the following general formula (G11) or general formula (G12).

$$^3H + {}^3H \rightarrow {}^1H^* + {}^1H \quad (G11)$$

$$^3H + {}^3H \rightarrow {}^3H^* + {}^1H \quad (G12)$$

The general formula (G11) represents a reaction in the host material 131 in which a singlet exciton ($^1H^*$) is formed from two triplet excitons ($^3H$) with a total spin quantum number of 0. The general formula (G12) represents a reaction in the host material 131 in which an electronically or oscillatorily excited triplet exciton ($^3H^*$) is formed from two triplet excitons ($^3H$) with a total spin quantum number of 1 (atomic unit). In the general formulae (G11) and (G12), $^1H$ represents the singlet ground state of the host material 131.

Although the reactions in the general formulae (G11) and (G12) occur at the same probability, there are three times as many pairs of triplet excitons with a total spin quantum number of 1 (atomic unit) as pairs of triplet excitons with a total spin quantum number of 0. In other words, when an exciton is formed from two triplet excitons, the singlet-triplet exciton formation ratio is 1:3 according to the statistically obtained probability. In the case where the density of the triplet excitons in the light-emitting layer 130 is sufficiently high (e.g., $1 \times 10^{-12}$ cm$^{-3}$ or more), only the reaction of two triplet excitons approaching each other can be considered whereas deactivation of a single triplet exciton is ignored.

Thus, by one reaction in the general formula (G11) and three reactions in the general formula (G12), one singlet exciton ($^1H^*$) and three triplet excitons ($^3H^*$) which are electronically or oscillatorily excited are formed from eight triplet excitons ($^3H$). This is represented by a general formula (G13).

$$8{}^3H \rightarrow {}^1H^* + 3{}^3H^* + 4{}^1H \quad (G13)$$

The electronically or oscillatorily excited triplet excitons ($^3H^*$), which are formed as in the general formula (G13), become triplet excitons ($^3H$) by relaxation and then repeat the reaction in the general formula (G13) again with other triplet excitons. Hence, in the general formula (G13), if all the triplet excitons ($^3H$) are converted into singlet excitons ($^1H^*$), five triplet excitons ($^3H$) form one singlet exciton ($^1H^*$) (a general formula (G14)).

$$5{}^3H \rightarrow {}^1H^* + 4{}^1H \quad (G14)$$

The ratio of singlet excitons ($^1H^*$) to triplet excitons ($^3H$) which are directly formed by recombination of carriers injected from a pair of electrodes is statistically as follows: $^1H^*:{}^3H=1:3$. That is, the probability of singlet excitons being directly formed by recombination of carriers injected from a pair of electrodes is 25%.

When the singlet excitons directly formed by recombination of carriers injected from a pair of electrodes and the singlet excitons formed by TTA are put together, eight singlet excitons can be formed from twenty excitons (the sum of singlet excitons and triplet excitons) directly formed by recombination of carriers injected from a pair of electrodes (a general formula (G15)). That is, TTA can increase the probability of singlet exciton formation from 25%, which is the conventional value, to at most 40% (=8/20).

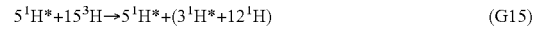

$$5{}^1H^* + 15{}^3H \rightarrow 5{}^1H^* + (3{}^1H^* + 12{}^1H) \quad (G15)$$

Figure 1C:
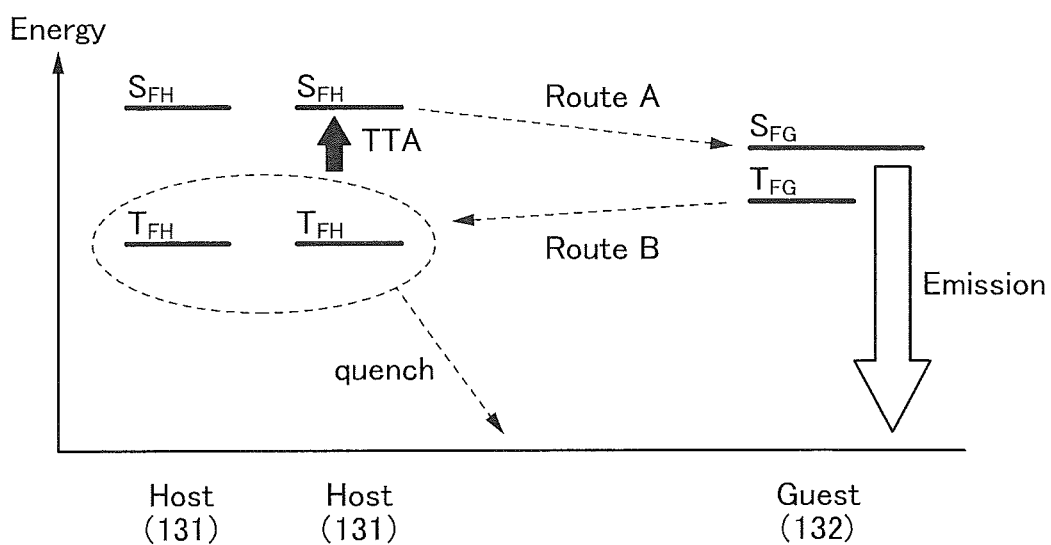

In the singlet excited state of the host material 131 which is formed by the singlet excitons formed by the above process, energy is transferred from the $S_1$ level ($S_{FH}$) of the host material 131 to the $S_1$ level ($S_{FG}$) of the guest material 132, which is lower than $S_{FH}$ (see Route A in FIG. 1C). Then, the guest material 132 brought into a singlet excited state emits fluorescence.

In the case where carriers recombine in the guest material 132 and an excited state formed by the formed excitons is a triplet excited state, if the $T_1$ level ($T_{FH}$) of the host material 131 is lower than the $T_1$ level ($T_{FG}$) of the guest material, triplet excited energy of $T_{FG}$ is not deactivated and transferred to $T_{FH}$ (see Route B in FIG. 1C) to contribute to TTA.

In the case where the $T_1$ level ($T_{FG}$) of the guest material 132 is lower than the $T_1$ level ($T_{FH}$) of the host material 131, the weight ratio of the guest material 132 to the host material 131 is preferably low. Specifically, the weight ratio of the guest material 132 to the host material 131 is preferably greater than 0 and less than or equal to 0.05, in which case, the probability of carrier recombination in the guest material 132 can be reduced. In addition, the probability of energy transfer from the $T_1$ level ($T_{FH}$) of the host material 131 to the $T_1$ level ($T_{FG}$) of the guest material 132 can be reduced.

As described above, triplet excitons formed in the light-emitting layer 130 can be converted into singlet excitons by TTA, so that light emitted from the guest material 132 can be efficiently obtained.

<TTA Efficiency>

Since TTA can increase the probability of formation of singlet excitons and the emission efficiency of a light-emitting element as described above, increasing the probability of occurrence of TTA (also referred to as TTA efficiency) is important for high emission efficiency. That is, it is important that a delayed fluorescence component due to TTA account for a large proportion of light emitted from the light-emitting element.

As described above, owing to the TTA process, the probability of formation of singlet excitons can be increased to at most 40% including 25% occupied by the singlet excitons that are directly formed by recombination of carriers injected from a pair of electrodes. Thus, a delayed fluorescence component due to TTA can account for at most 37.5% ((40%−25%)/40%) of light emitted from the light-emitting element.

Anthracene compounds are generally used as a host material in a light-emitting element that emits blue light, and a delayed fluorescence component due to TTA accounts for approximately 10% of light emission. In contrast, tetracene compounds known as a compound with high TTA efficiency are difficult to use as a host material in a light-emitting element that emits blue light because they are compounds that emit yellow light or light with a longer wavelength than yellow light.

Thus, to achieve a light-emitting element that emits blue light and has high emission efficiency in which a delayed fluorescence component due to TTA accounts for a large proportion, the use of a compound in which a delayed fluorescence component due to TTA accounts for a large proportion as in tetracene and which has high excited energy like anthracene, as a host material, is required.

<Quantum Chemical Calculations>

Figure 2A:
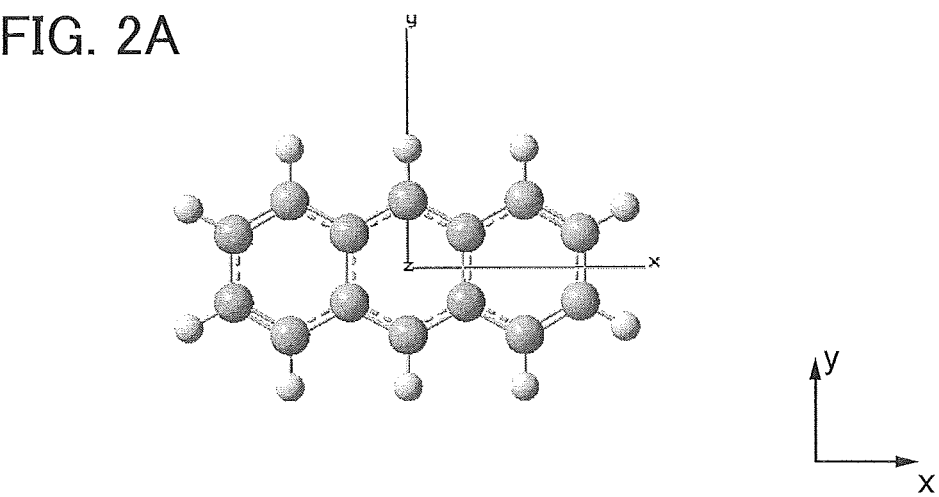
FIGS. 2A to 2C show calculation examples of compounds according to one embodiment of the present invention.
Figure 2B:
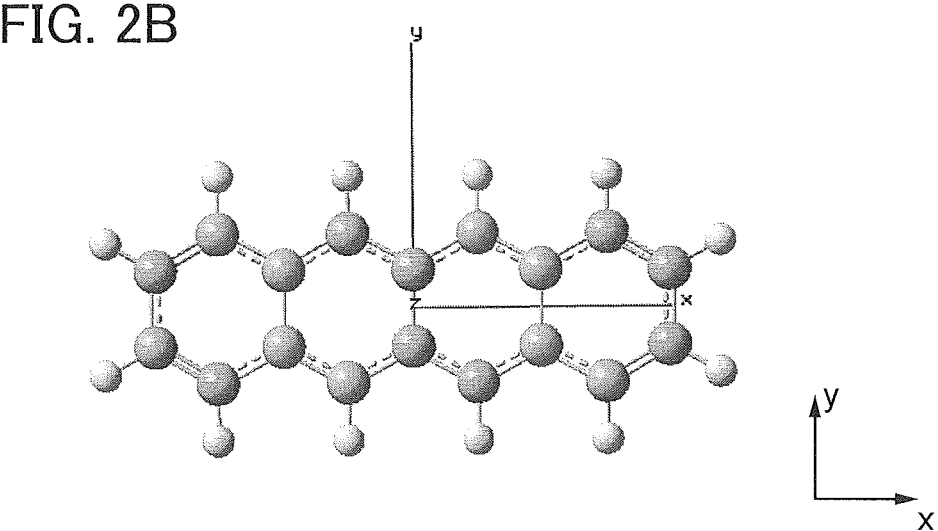
Figure 2C:
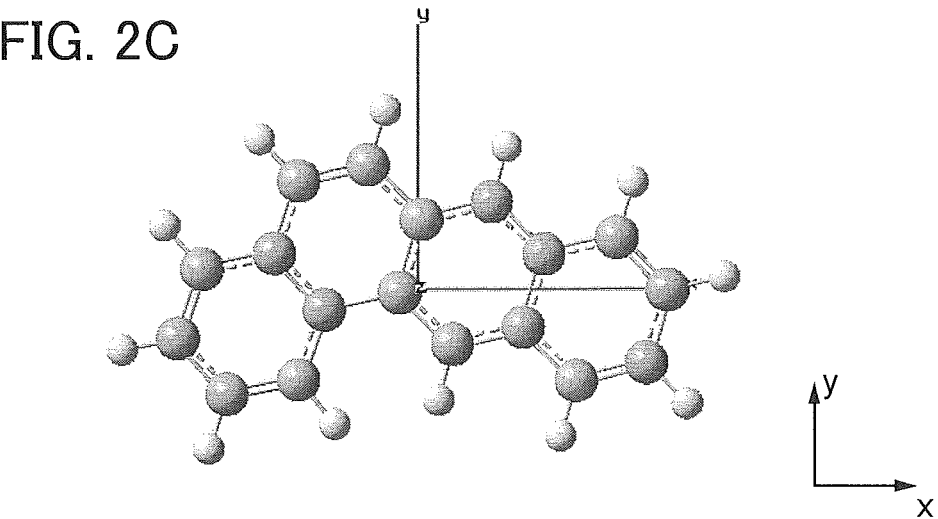

Quantum chemical calculations were performed to find the excited energy levels ($S_1$ level and $T_1$ level) and the transition dipole momentum and oscillator strengths from the singlet ground state to the lowest singlet excited state of anthracene, which is a tricyclic aromatic hydrocarbon, and tetracene and benzo[a]anthracene, which are tetracyclic aromatic hydrocarbons. The compounds used for the calculations are shown in FIGS. 2A to 2C and the calculation results are listed in Table 1. Note that FIG. 2A shows anthracene, FIG. 2B tetracene, and FIG. 2C benzo[a]anthracene. The calculation method is described below.

TABLE 1

| Abbreviation | $S_1$ level (eV) | $T_1$ level (eV) | Transition dipole moment | | | Oscillator strength |
|---|---|---|---|---|---|---|
| | | | x | y | z | |
| Anthracene | 3.24 | 1.84 | 0 | 0.846 | 0 | 0.0568 |
| Tetracene | 2.46 | 1.16 | 0 | 0.893 | 0 | 0.0481 |
| Benzo[a]anthracene | 3.36 | 2.08 | −0.436 | −0.651 | 0 | 0.0506 |

To find the $S_1$ levels, $T_1$ levels, transition dipole momentum, and oscillator strengths of the above compounds, the most stable structure in the singlet ground state of each compound was calculated using the density functional theory (DFT). As the quantum chemistry computational program, Gaussian 09 was used. A high performance computer (manufactured by SGI Japan, Ltd.) was used for the calculation. As a basis function, 6-311G (d,p) was used, and as a functional, B3LYP was used. The time-dependent density functional theory (TD-DFT) was further used to find the $S_1$ level, the $T_1$ level, and the transition dipole moment from the singlet ground state to the lowest singlet excited state. In the DFT, the total energy is represented as the sum of potential energy, electrostatic energy between electrons, electronic kinetic energy, and exchange-correlation energy including all the complicated interactions between electrons. Also in the DFT, an exchange-correlation interaction is approximated by a functional (a function of another function) of one electron potential represented in terms of electron density to enable high-accuracy calculations.

As listed in Table 1, benzo[a]anthracene is a tetracyclic aromatic hydrocarbon but has a $S_1$ level and a $T_1$ level that are approximately as high as those of anthracene, which is a tricyclic aromatic hydrocarbon.

The transition dipole moment of benzo[a]anthracene is approximately as high as those of anthracene and tetracene, and the oscillator strength of benzo[a]anthracene is also sufficiently high. The transition dipole momentum and oscillator strengths shown in Table 1 relate to the transition from the singlet ground state to the lowest singlet excited state in the compounds. The arrows in FIGS. 2A to 2C indicate the directions (x, y, and z) of the transition dipole momentum. The z-direction is perpendicular to the paper. The reason for the negative value of the transition dipole moment of benzo[a]anthracene is because the directions of the transition dipole moment are opposite to the x- and y-directions in FIGS. 2A to 2C. Since the magnitude of the transition dipole moment can be evaluated from its absolute value, the transition dipole moment of benzo[a]anthracene can be found sufficiently large.

A large transition dipole moment and high oscillator strength from the singlet ground state to the lowest singlet excited state mean that the lowest singlet excited state can be easily generated. Thus, the lowest singlet excited states of anthracene, tetracene, and benzo[a]anthracene can be easily generated, and therefore these compounds are likely to exhibit high TTA efficiency in a TTA process.

In particular, a tetracyclic aromatic hydrocarbon compound (e.g., benzo[a]anthracene), which is a tetracyclic aromatic hydrocarbon compound like tetracene and has a nonlinear structure with approximately as high singlet excited energy as that of anthracene, has high excited energy and is likely to exhibit high TTA efficiency. Thus, in the compound, the proportion of a delayed fluorescence component due to TTA can be increased.

When higher emission efficiency than that of a light-emitting element including an anthracene compound as a host material is desired, the proportion of a delayed fluorescence component due to TTA is preferably larger than that in the light-emitting element including an anthracene compound as a host material. Specifically, a delayed fluorescence component due to TTA preferably accounts for 20% or more of emissive components of the light-emitting element.

An emission spectrum of a light-emitting element preferably has a peak in the blue wavelength range, or more specifically, at least one peak at a wavelength greater than or equal to 400 nm and less than or equal to 550 nm.

Note that a factor of delayed fluorescence in a light-emitting element, which is other than TTA, may be thermally activated delayed fluorescence due to reverse intersystem crossing from the triplet excited state to the singlet excited state. To efficiently cause reverse intersystem crossing, an energy difference between the $S_1$ level and the $T_1$ level is preferably 0.2 eV or less. In other words, an energy difference greater than 0.2 eV between the $S_1$ level and the $T_1$ level hardly causes reverse intersystem crossing. Therefore, to efficiently cause TTA, an energy difference between the lowest singlet excited energy level and lowest triplet excited energy level of a compound in which TTA occurs is preferably greater than 0.2 eV, further preferably greater than or equal to 0.5 eV.

The lowest singlet excited energy level of an organic compound can be observed from an absorption spectrum at a transition from the singlet ground state to the lowest singlet excited state in the organic compound. Alternatively, the lowest singlet excited energy level may be estimated from a peak wavelength of a fluorescence spectrum of the organic compound. Furthermore, the lowest triplet excited energy level can be observed from an absorption spectrum at a transition from the singlet ground state to the lowest triplet excited state in the organic compound, but is difficult to observe in some cases because this transition is a forbidden transition. In such cases, the lowest triplet excited energy level may be estimated from a peak wavelength of a phosphorescence spectrum of the organic compound. Thus, a difference in equivalent energy value between the peak wavelengths of the fluorescence and phosphorescence spectra of the organic compound is preferably greater than 0.2 eV, further preferably greater than or equal to 0.5 eV.

<Materials>

Next, components of a light-emitting element of one embodiment of the present invention are described in detail.

<<Light-Emitting Layer>>

In the light-emitting layer 130, the weight percentage of the host material 131 is higher than that of at least the guest material 132, and the guest material 132 (fluorescent material) is dispersed in the host material 131. A material that can be used as the host material 131 in the light-emitting layer 130 is preferably an organic compound in which a delayed fluorescence component due to triplet-triplet annihilation (TTA) accounts for a large proportion of emitted light, or more specifically, an organic compound in which a delayed fluorescence component due to TTA accounts for 20% or more. In particular, a compound having a benzo[a]anthracene skeleton is preferred. In the light-emitting layer 130, the host material 131 may be composed of one kind of compound or a plurality of compounds.

In the light-emitting layer 130, the guest material 132 is preferably, but not particularly limited to, an anthracene derivative, a tetracene derivative, a chrysene derivative, a phenanthrene derivative, a pyrene derivative, a perylene derivative, a stilbene derivative, an acridone derivative, a coumarin derivative, a phenoxazine derivative, a phenothiazine derivative, or the like, and for example, any of the following materials can be used.

The examples include 5,6-bis[4-(10-phenyl-9-anthryl) phenyl]-2,2'-bipyridine (abbreviation: PAP2BPy), 5,6-bis [4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N"-(2-tert-butylanthracene-9,10-diyldi-4,1-phenylene)bis [N,N',N'-triphenyl-1,4-phenylenediamine] (abbreviation: DPABPA), N,9-diphenyl-N-[4-(9,10-diphenyl-2-anthryl) phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N', N",N"N"', N"''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 6, coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene) propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N', N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij] quinolizin-9-yl)ethenyl]-4H-pyran-4-yliden}propaned initrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis {2-[4-(dimethylamino)phenyl] ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl) ethenyl]-4H-pyran-4-ylidene}propanedinitrile (abbreviation: BisDCJTM), and 5,10,15,20-tetraphenylbisbenzo[5,6] indeno[1,2,3-cd:1',2',3'-lm]perylene.

The light-emitting layer 130 may include a material other than the host material 131 and the guest material 132.

Although there is no particular limitation on a material that can be used in the light-emitting layer 130, any of the following materials can be used, for example: metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato) beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyephenolato]zinc(II) (abbreviation: ZnPBO), and bis[2-(2-benzothiazolyl)phenolato]zinc (II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)-tris(1-phenyl-1H-benzimidazole) (abbreviation: TPBI), bathophenanthroline (abbreviation: BPhen), bathocuproine (abbreviation: BCP), and 9-[4-(5-phenyl-1,3,4-oxadiazol-2-yl) phenyl]-9H-carbazole (abbreviation: CO11); and aromatic amine compounds such as 4,4'-bis[N-(1-naphthyl)-N-phenylamino]biphenyl (abbreviation: NPB or α-NPD), N,N'-bis(3-methylphenyl)-N,N-diphenyl-[1,1'-biphenyl]-4,4'-diamine (abbreviation: TPD), and 4,4'-bis[N-(Spiro-9,9'-bifluoren-2-yl)-N-phenylamino]biphenyl (abbreviation: BSPB). In addition, condensed polycyclic aromatic compounds such as anthracene derivatives, phenanthrene derivatives, pyrene derivatives, chrysene derivatives, and dibenzo [g,p]chiysene derivatives can be used. Specific examples thereof include 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N,9-diphenyl-N-(9,10-diphenyl-2-anthryl)-9H-carbazol-3-amine (abbreviation: 2PCAPA), 6,12-dimethoxy-5,11-diphenylchrysene, N,N,N',N',N",N",N"',N"'-octaphenyldibenzo[g,p]chrysene-2,7,10,15-tetraamine (abbreviation:

DBC1), 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diphenanthrene (abbreviation: DPNS), 9,9'-(stilbene-4,4'-diyl)diphenanthrene (abbreviation: DPNS2), and 1,3,5-tri(1-pyrenyl)benzene (abbreviation: TPB3). A plurality of compounds each having a benzo[a]anthracene skeleton may be included. One or more substances having a wider energy gap than the guest material 132 is preferably selected from these substances and known substances.

The light-emitting layer 130 can have a structure in which two or more layers are stacked. For example, in the case where the light-emitting layer 130 is formed by stacking a first light-emitting layer and a second light-emitting layer in this order from the hole-transport layer side, the first light-emitting layer is formed using a substance having a hole-transport property as the host material and the second light-emitting layer is formed using a substance having an electron-transport property as the host material. Also in such a case, at least one light-emitting layer preferably includes a compound having a benzo[a]anthracene skeleton.

Next, details of other components of the light-emitting element 150 in FIG. 1A are described.

<<Pair of Electrodes>>

The electrode 101 and the electrode 102 have functions of injecting holes and electrons into the light-emitting layer 130. The electrodes 101 and 102 can be formed using a metal, an alloy, or a conductive compound, or a mixture or a stack thereof, for example. A typical example of the metal is aluminum, besides, a transition metal such as silver, tungsten, chromium, molybdenum, copper, or titanium, an alkali metal such as lithium or cesium, or a Group 2 metal such as calcium or magnesium can be used. As the transition metal, a rare earth metal such as ytterbium (Yb) may be used. An alloy containing any of the above metals can be used as the alloy, and MgAg and AlLi can be given as examples. As the conductive compound, a metal oxide such as indium oxide-tin oxide (indium tin oxide) can be given. It is also possible to use an inorganic carbon-based material such as graphene as the conductive compound. As described above, the electrode 101 and/or the electrode 102 may be formed by stacking two or more of these materials.

Light emitted from the light-emitting layer 130 is extracted through the electrode 101 and/or the electrode 102. Therefore, at least one of the electrodes 101 and 102 transmits visible light. In the case where the electrode through which light is extracted is formed using a material with low light transmittance, such as metal or alloy, the electrode 101 and/or the electrode 102 is formed to a thickness that is thin enough to transmit visible light (e.g., a thickness of 1 nm to 10 nm).

<<Hole-Injection Layer>>

The hole-injection layer 111 has a function of reducing a barrier for hole injection from one of the pair of electrodes (the electrode 101 or the electrode 102) to promote hole injection and is formed using a transition metal oxide, a phthalocyanine derivative, or an aromatic amine, for example. As the transition metal oxide, molybdenum oxide, vanadium oxide, ruthenium oxide, tungsten oxide, manganese oxide, or the like can be given. As the phthalocyanine derivative, phthalocyanine, metal phthalocyanine, or the like can be given. As the aromatic amine, a benzidine derivative, a phenylenediamine derivative, or the like can be given. It is also possible to use a high molecular compound such as polythiophene or polyaniline; a typical example thereof is poly(ethylenedioxythiophene)/poly(styrenesulfonic acid), which is self-doped polythiophene.

As the hole-injection layer 111, a layer containing a composite material of a hole-transport material and a material having a property of accepting electrons from the hole-transport material can also be used. Alternatively, a stack of a layer containing a material having an electron accepting property and a layer containing a hole-transport material may also be used. In a steady state or in the presence of an electric field, electric charge can be transferred between these materials. As examples of the material having an electron-accepting property, organic acceptors such as a quinodimethane derivative, a chloranil derivative, and a hexaazatriphenylene derivative can be given. A specific example is a compound having an electron-withdrawing group (a halogen group or a cyano group), such as 7,7,8,8-tetracyano-2,3,5,6-tetrafluoroquinodimethane (abbreviation: $F_4$-TCNQ), chloranil, or 2,3,6,7,10,11-hexacyano-1,4,5,8,9,12-hexaazatriphenylene (abbreviation: HAT-CN). Alternatively, a transition metal oxide such as an oxide of a metal from Group 4 to Group 8 can also be used. Specifically, vanadium oxide, niobium oxide, tantalum oxide, chromium oxide, molybdenum oxide, tungsten oxide, manganese oxide, rhenium oxide, or the like can be used. In particular, molybdenum oxide is preferable because it is stable in the air, has a low hygroscopic property, and is easily handled.

A material having a property of transporting more holes than electrons can be used as the hole-transport material, and a material having a hole mobility of $1 \times 10^{-6}$ $cm^2/Vs$ or higher is preferable. Specifically, an aromatic amine, a carbazole derivative, an aromatic hydrocarbon, a stilbene derivative, or the like can be used. Furthermore, the hole-transport material may be a high molecular compound.

Examples of the material having a high hole-transport property are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and the like.

Specific examples of the carbazole derivative are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl) amino]-9-phenylcarbazole (abbreviation: PCzPCN1), and the like.

Other examples of the carbazole derivative are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Examples of the aromatic hydrocarbon are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Other examples are pentacene, coronene, and the like. The aromatic hydrocarbon having a hole mobility of $1\times10^{-6}$ cm$^2$/Vs or more and having 14 to 42 carbon atoms is particularly preferable.

The aromatic hydrocarbon that can be used for the composite material may have a vinyl skeleton. Examples of the aromatic hydrocarbon having a vinyl group are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Other examples are high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: poly-TPD).

<<Hole-Transport Layer>>

The hole-transport layer 112 is a layer containing a hole-transport material and can be formed using any of the materials given as examples of the material of the hole-injection layer 111. In order that the hole-transport layer 112 has a function of transporting holes injected into the hole-injection layer 111 to the light-emitting layer 130, the highest occupied molecular orbital (HOMO) level of the hole-transport layer 112 is preferably equal or close to the HOMO level of the hole-injection layer 111.

In addition to the hole-transport materials given as the material of the hole-injection layer 111, examples of the substance having a hole-transport property are aromatic amine compounds such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), and the like. The substances described here are mainly substances having a hole mobility of $1\times10^{-6}$ cm$^2$/Vs or higher. Note that any substance other than the above substances may be used as long as the hole-transport property is higher than the electron-transport property. The layer including a substance having a high hole-transport property is not limited to a single layer, and two or more layers containing the aforementioned substances may be stacked.

The compound having a benzo[a]anthracene skeleton may also be used as a material contained in the hole-transport layer 112.

<<Electron-Transport Layer>>

The electron-transport layer 118 has a function of transporting, to the light-emitting layer 130, electrons injected from the other of the pair of electrodes (the electrode 101 or the electrode 102) through the electron-injection layer 119. A material having a property of transporting more electrons than holes can be used as an electron-transport material, and a material having an electron mobility of $1\times10^{-6}$ cm$^2$/Vs or higher is preferable. Specific examples include a metal complex having a quinoline ligand, a benzoquinoline ligand, an oxazole ligand, or a thiazole ligand; an oxadiazole derivative; a triazole derivative; a phenanthroline derivative; a pyridine derivative; a bipyridine derivative; a pyrimidine derivative.

For example, the electron-transport layer is formed using a metal complex having a quinoline skeleton or a benzoquinoline skeleton, such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryllium(III) (abbreviation: BeBq$_2$), or bis(2-methyl-8-quinolinolato)(4-phenylphenolato)aluminum(III) (abbreviation: BAlq), or the like. A metal complex having an oxazole-based or thiazole-based ligand, such as bis[2-(2-hydroxyphenyl)benzoxazolato]zinc(II) (abbreviation: Zn(BOX)$_2$) or bis[2-(2-hydroxyphenyl)benzothiazolato]zinc(II) (abbreviation: Zn(BTZ)$_2$), or the like can also be used. Other than the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances given here are mainly ones having an electron mobility of $10^{-6}$ cm$^2$/Vs or higher. A compound having a benzo[a]anthracene skeleton can also be suitably used. Note that any substance other than the above substances may be used for the electron-transport layer as long as the substance has an electron-transport property higher than a hole-transport property. Furthermore, the electron-transport layer 118 is not limited to a single layer and may be a stack of two or more layers including any of the above substances.

Between the electron-transport layer 118 and the light-emitting layer 130, a layer that controls transport of electron carriers may be provided. This is a layer formed by addition of a small amount of a substance having a high electron-trapping property to the aforementioned material having a high electron-transport property, and the layer is capable of adjusting carrier balance by retarding transport of electron carriers. Such a structure is very effective in preventing a problem (such as a reduction in element lifetime) caused when electrons pass through the light-emitting layer.

<<Electron-Injection Layer>>

The electron-injection layer 119 has a function of reducing a barrier for electron injection from the electrode 102 to promote electron injection and can be formed using a Group 1 metal or a Group 2 metal, or an oxide, a halide, or a carbonate of any of the metals, for example. Alternatively, a composite material containing an electron-transport material (described above) and a material having a property of donating electrons to the electron-transport material can also be used. As the material having an electron-donating property, a Group 1 metal, a Group 2 metal, an oxide of any of the metals, or the like can be given.

Note that the light-emitting layer, the hole-injection layer, the hole-transport layer, the electron-transport layer, and the electron-injection layer described above can each be formed by an evaporation method (including a vacuum evaporation method), an inkjet method, a coating method, a gravure printing method, or the like. Besides the above-mentioned materials, an inorganic compound or a high molecular compound (e.g., an oligomer, a dendrimer, or a polymer) may be used in the light-emitting layer, the hole-injection layer, the hole-transport layer, the electron-transport layer, and the electron-injection layer.

<<Substrate>>

The light-emitting element 150 is fabricated over a substrate of glass, plastic, or the like. As the way of stacking layers over the substrate, layers may be sequentially stacked from the electrode 101 side or sequentially stacked from the electrode 102 side.

Note that, for example, glass, quartz, plastic, or the like can be used for the substrate over which the light-emitting element 150 can be formed. Alternatively, a flexible substrate can be used. The flexible substrate is a substrate that can be bent, such as a plastic substrate made of polycarbonate or polyarylate, for example. A film, an inorganic film formed by evaporation, or the like can also be used. Note that materials other than these can be used as long as they can function as a support in a manufacturing process of the light-emitting element and an optical element or as long as they have a function of protecting the light-emitting element and the optical element.

The light-emitting element 150 can be formed using a variety of substrates, for example. The type of substrate is not limited to a certain type. As the substrate, a semiconductor substrate (e.g., a single crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, a base material film, or the like can be used, for example. Examples of the glass substrate include a barium borosilicate glass substrate, an aluminoborosilicate glass substrate, and a soda lime glass substrate. Examples of the flexible substrate, the attachment film, the base material film, and the like are substrates of plastics typified by polyethylene terephthalate (PET), polyethylene naphthalate (PEN), polyether sulfone (PES), and polytetrafluoroethylene (PTFE). Another example is a resin such as acrylic. Other examples are polypropylene, polyester, polyvinyl fluoride, polyvinyl chloride, and the like. Other examples are polyamide, polyimide, aramid, epoxy, an inorganic film formed by evaporation, paper, and the like.

Alternatively, a flexible substrate may be used as the substrate, and the light-emitting element may be provided directly on the flexible substrate. Alternatively, a separation layer may be provided between the substrate and the light-emitting element. The separation layer can be used when part or the whole of the light-emitting element formed over the separation layer is completed, separated from the substrate, and transferred to another substrate. In such a case, the light-emitting element can be transferred to a substrate having low heat resistance or a flexible substrate as well. For the above separation layer, a stack including inorganic films, which are a tungsten film and a silicon oxide film, or a resin film of polyimide or the like formed over a substrate can be used, for example.

In other words, after the light-emitting element is formed using a substrate, the light-emitting element may be transferred to another substrate. Examples of a substrate to which the light-emitting element is transferred include, in addition to the above-described substrates, a cellophane substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester, or the like), a leather substrate, and a rubber substrate. By using such a substrate, a light-emitting element with high durability, a light-emitting element with high heat resistance, a lightweight light-emitting element, or a thin light-emitting element can be obtained.

The light-emitting element 150 may be formed over an electrode electrically connected to a field-effect transistor (FET), for example, which is formed over the above-mentioned substrate, so that an active matrix display device in which the FET controls the drive of the light-emitting element 150 can be manufactured.

In Embodiment 1, one embodiment of the present invention is described. Other embodiments of the present invention are described in the other embodiments. Note that one embodiment of the present invention is not limited thereto. Although the case where a delayed fluorescence component due to triplet-triplet annihilation accounts for 20% or more of light emitted from the EL layer and the emitted light has an emission spectrum peak in the blue wavelength range is exemplified in one embodiment of the present invention, one embodiment of the present invention is not limited thereto. Depending on circumstances or conditions, in one embodiment of the present invention, a delayed fluorescence component need not account for 20% or more of light emitted from the EL layer. Alternatively, the emitted light need not have an emission spectrum peak in the blue wavelength range. Alternatively, the emitted light need not have any emission spectrum peak at a wavelength greater than or equal to 400 nm and less than or equal to 550 nm. Although the case where the EL layer includes an organic compound with an energy difference of 0.5 eV or more between the lowest singlet excited energy level and the lowest triplet excited energy level, a delayed fluorescence component accounts for 20% or more of light emitted from the EL layer, and the emitted light has an emission spectrum peak in the blue wavelength range is exemplified in one embodiment of the present invention, one embodiment of the present invention is not limited thereto. Depending on circumstances or conditions, in one embodiment of the present invention, the EL layer need not include an organic compound with an energy difference of 0.5 eV or more between the lowest singlet excited energy level and the lowest triplet excited energy level. Although the case where the EL layer includes a compound having a benzo[a]anthracene skeleton and a delayed fluorescence component accounts for 20% or more of light emitted from the EL layer is exemplified in one embodiment of the present invention, one embodiment of the present invention is not limited thereto. Depending on circumstances, the EL layer need not include a compound having a benzo[a]anthracene skeleton.

The structure described above in this embodiment can be combined with any of the structures described in the other embodiments as appropriate.

Embodiment 2

In this embodiment, a compound that can suitably be used in a light-emitting element of one embodiment of the present invention is described below.

A compound of this embodiment includes a carbazole derivative in which a carbazole skeleton is bonded to the 7-position of a benzo[a]anthracene skeleton via at least an arylene group. Since a delayed fluorescence component due to TTA accounts for a large proportion of emitted light in the benzo[a]anthracene compound, use of the benzo[a]anthracene compound in a light-emitting element achieves high emission efficiency. The wide band gap of the benzo[a]anthracene compound also leads to high emission efficiency of the light-emitting element using the benzo[a]anthracene compound. In particular, a light-emitting element with high emission efficiency which emits blue light can be fabricated. Furthermore, because of the excellent carrier-transport property of the benzo[a]anthracene compound, use of the benzo[a]anthracene compound in a light-emitting element enables the light-emitting element to be driven at a low voltage. In addition, since the benzo[a]anthracene compound is highly resistant to repetition of oxidation and reduction, use of the benzo[a]anthracene compound in a light-emitting element enables the long operating life of the light-emitting element. As described above, the use of the compound of this embodiment in a light-emitting element achieves a high-performance light-emitting element having excellent emission characteristics.

When the number of carbon atoms of the arylene group is 6 to 13, the benzo[a]anthracene compound is a low molecular compound with a relatively low molecular weight and accordingly has a structure suitable for vacuum evaporation (capable of being vacuum-evaporated at a relatively low temperature). In general, a lower molecular weight tends to diminish heat resistance after film formation. However, even with a low molecular weight, the benzo[a]anthracene compound has an advantage in that sufficient heat resistance can be ensured because of the effect of the rigid benzo[a]anthracene skeleton.

Since the carbazole skeleton is bonded to the 7-position of a benzo[a]anthracene skeleton via an arylene group, the carrier-transport property of the benzo[a]anthracene compound is improved. Accordingly, a light-emitting element using the benzo[a]anthracene compound can be driven at a low voltage.

The above benzo[a]anthracene compound can also be referred to as a benzo[a]anthracene compound in which an arylcarbazole derivative is bonded to a benzo[a]anthracene skeleton. The benzo[a]anthracene compound can be easily synthesized with high purity, so that deterioration due to impurities can be suppressed. The number of carbon atoms of the aryl group of the arylcarbazole derivative which is bonded to the benzo[a]anthracene skeleton is preferably 6 to 13 in terms of the stability and reliability of element characteristics. In this case, the benzo[a]anthracene compound can be vacuum-evaporated at a relatively low temperature as described above and accordingly is unlikely to deteriorate due to pyrolysis or the like at evaporation. In addition, the compound is excellent in not only reliability but also drive voltage. This is also because the benzo[a]anthracene compound has high electrochemical stability and a high carrier-transport property owing to the molecular structure in which a carbazole skeleton is bonded to the 7-position of a benzo[a]anthracene skeleton via an arylene group.

A benzo[a]anthracene compound in which a benzo[a]anthracene skeleton is bonded to the 9-position of a carbazole skeleton via an arylene group has a wide band gap, and therefore can suitably be used particularly in a light-emitting element that emits light with high energy such as blue light. Note that the carbazole skeleton and the benzo[a]anthracene skeleton are preferably bonded via an arylene group such as a phenylene group or a naphthylene group.

For the above reason, the benzo[a]anthracene compound in which the 9-position of a carbazole skeleton and the 7-position of a benzo[a]anthracene skeleton are bonded via an arylene group is preferred. In other words, a benzo[a]anthracene compound in which a (9-carbazolyl)aryl group is bonded to the 7-position of a benzo[a]anthracene skeleton is preferred. The number of carbon atoms of an aryl group of the (9-carbazolyl)aryl group which is bonded to the benzo[a]anthracene skeleton is preferably 6 to 13 in terms of the stability of the compound and the light-emitting element. Thus, the benzo[a]anthracene compound has a wide band gap which is a feature due to the effect of the skeleton of a 9-carbazolyl group, in addition to the high suitability for evaporation, electrochemical stability, and carrier-transport property described above. Hence, the benzo[a]anthracene compound is effective in a structure of a light-emitting element in which it is used as a host material of a light-emitting layer and a light-emitting material is added as a guest material to the light-emitting layer. This compound is suitably used as a host material particularly in a blue light-emitting element.

Example 1 of Compound

The above-described benzo[a]anthracene compound is the benzo[a]anthracene compound represented by the following general formula (G1).

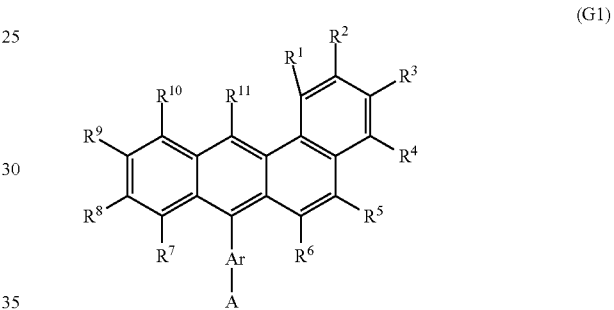

In the above general formula (G1), A represents a substituted or unsubstituted carbazolyl group. In the case where the carbazolyl group has a substituent, as the substituent, an alkyl group having 1 to 6 carbon atoms, a cycloalkyl group having 3 to 6 carbon atoms, or a substituted or unsubstituted aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 6 carbon atoms include a cyclopropyl group, a cyclobutyl group, a cyclopentyl group, a cyclohexyl group, and the like. Specific examples of the aryl group having 6 to 12 carbon atoms are a phenyl group, a naphthyl group, a biphenyl group, and the like.

Furthermore, $R^1$ to $R^{10}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms. Furthermore, $R^{11}$ represents any of hydrogen, an alkyl group having 1 to 6 carbon atoms, a cycloalkyl group having 3 to 6 carbon atoms, and a substituted or unsubstituted phenyl group. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 6 carbon atoms include a cyclopropyl group, a cyclobutyl group, a cyclopentyl group, a cyclohexyl group, and the like. Specific examples of the aryl group having 6 to 13 carbon atoms are a phenyl group, a naphthyl group, a biphenyl group, a fluorenyl group, and the like. The above aryl group or phenyl group may include one or more substituents, and the substituents may be bonded to each other to form a ring. As the substituent, an alkyl group having 1 to 6 carbon atoms, a cycloalkyl group having 3 to 6 carbon atoms, or an aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 6 carbon atoms include a cyclopropyl group, a cyclobutyl group, a cyclopentyl group, a cyclohexyl group, and the like. Specific examples of the aryl group having 6 to 12 carbon atoms include a phenyl group, a naphthyl group, a biphenyl group, and the like.

Furthermore, Ar represents an arylene group having 6 to 13 carbon atoms. The arylene group may include one or more substituents and the substituents may be bonded to each other to form a ring. For example, a carbon atom at the 9-position in a fluorenyl group has two phenyl groups as substituents and the phenyl groups are bonded to form a spirofluorene skeleton. Specific examples of the arylene group having 6 to 13 carbon atoms are a phenylene group, a naphthylene group, a biphenylene group, a fluorenediyl group, and the like. In the case where the arylene group has a substituent, as the substituent, an alkyl group having 1 to 6 carbon atoms, a cycloalkyl group having 3 to 6 carbon atoms, or an aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 6 carbon atoms include a cyclopropyl group, a cyclobutyl group, a cyclopentyl group, a cyclohexyl group, and the like. Specific examples of the aryl group having 6 to 12 carbon atoms are a phenyl group, a naphthyl group, a biphenyl group, and the like.

Example 2 of Compound

As a benzo[a]anthracene compound of this embodiment, a benzo[a]anthracene compound having a structure in which a benzo[a]anthracene skeleton is bonded to the 9-position of a carbazolyl group via an arylene group has a wide band gap, and therefore can suitably be used especially in a light-emitting element that emits light with high energy such as blue light, which is preferable. Because the benzo[a]anthracene compound has an excellent carrier-transport property, a light-emitting element including the compound can be driven at a low voltage, which is preferable. The above-described benzo[a]anthracene compound is the benzo[a]anthracene compound represented by the following general formula (G2).

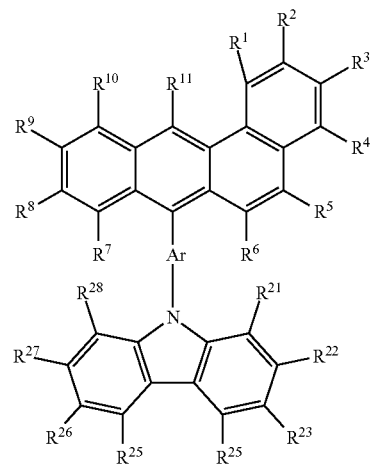

(G2)

In the above general formula (G2), $R^1$ to $R^{10}$ and $R^{21}$ to $R^{28}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms. Furthermore, $R^{11}$ represents any of hydrogen, an alkyl group having 1 to 6 carbon atoms, a cycloalkyl group having 3 to 6 carbon atoms, and a substituted or unsubstituted phenyl group. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 6 carbon atoms include a cyclopropyl group, a cyclobutyl group, a cyclopentyl group, a cyclohexyl group, and the like. Specific examples of the aryl group having 6 to 13 carbon atoms are a phenyl group, a naphthyl group, a biphenyl group, a fluorenyl group, and the like. The above aryl group or phenyl group may include one or more substituents, and the substituents may be bonded to each other to form a ring. As the substituent, an alkyl group having 1 to 6 carbon atoms, a cycloalkyl group having 3 to 6 carbon atoms, or an aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 6 carbon atoms include a cyclopropyl group, a cyclobutyl group, a cyclopentyl group, a cyclohexyl group, and the like. Specific examples of the aryl group having 6 to 12 carbon atoms include a phenyl group, a naphthyl group, a biphenyl group, and the like.

Furthermore, Ar represents an arylene group having 6 to 13 carbon atoms. The arylene group may include one or more substituents and the substituents may be bonded to each other to form a ring. For example, a carbon atom at the 9-position in a fluorenyl group has two phenyl groups as substituents and the phenyl groups are bonded to form a spirofluorene skeleton. Specific examples of the arylene group having 6 to 13 carbon atoms are a phenylene group, a naphthylene group, a biphenylene group, a fluorenediyl group, and the like. In the case where the arylene group has a substituent, as the substituent, an alkyl group having 1 to 6 carbon atoms, a cycloalkyl group having 3 to 6 carbon atoms, or an aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 6 carbon atoms include a cyclopropyl group, a cyclobutyl group, a cyclopentyl group, a cyclohexyl group, and the like. Specific examples of the aryl group having 6 to 12 carbon atoms are a phenyl group, a naphthyl group, a biphenyl group, and the like.

Example 3 of Compound

As a benzo[a]anthracene compound of this embodiment, a benzo[a]anthracene compound having a structure in which a benzo[a]anthracene skeleton is bonded to any of the 1- to 4-positions of a carbazolyl group via an arylene group has an excellent carrier-transport property, and therefore a light-emitting element including the compound can be driven at a low voltage, which is preferable. The above-described benzo[a]anthracene compound is the benzo[a]anthracene compound represented by the following general formula (G3).

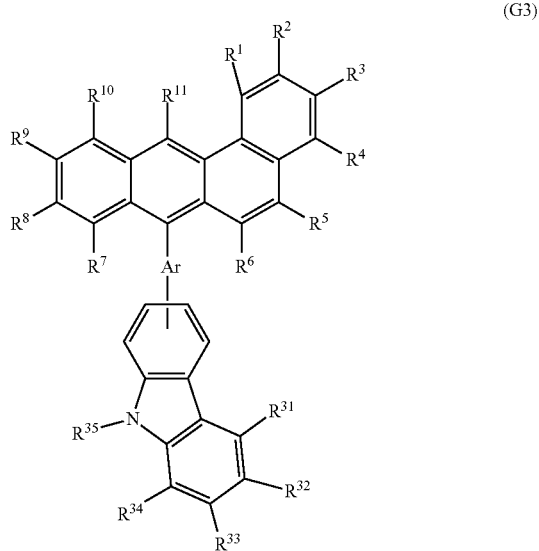

(G3)

In the above general formula (G3), $R^1$ to $R^{10}$ and $R^{31}$ to $R^{35}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms. Furthermore, $R^{11}$ represents any of hydrogen, an alkyl group having 1 to 6 carbon atoms, a cycloalkyl group having 3 to 6 carbon atoms, and a substituted or unsubstituted phenyl group. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 6 carbon atoms include a cyclopropyl group, a cyclobutyl group, a cyclopentyl group, a cyclohexyl group, and the like. Specific examples of the aryl group having 6 to 13 carbon atoms are a phenyl group, a naphthyl group, a biphenyl group, a fluorenyl group, and the like. The above aryl group or phenyl group may include one or more substituents, and the substituents may be bonded to each other to form a ring. As the substituent, an alkyl group having 1 to 6 carbon atoms, a cycloalkyl group having 3 to 6 carbon atoms, or an aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 6 carbon atoms include a cyclopropyl group, a cyclobutyl group, a cyclopentyl group, a cyclohexyl group, and the like. Specific examples of the aryl group having 6 to 12 carbon atoms include a phenyl group, a naphthyl group, a biphenyl group, and the like.

Furthermore, Ar represents an arylene group having 6 to 13 carbon atoms. The arylene group may include one or more substituents and the substituents may be bonded to each other to form a ring. For example, a carbon atom at the 9-position in a fluorenyl group has two phenyl groups as substituents and the phenyl groups are bonded to form a spirofluorene skeleton. Specific examples of the arylene group having 6 to 13 carbon atoms are a phenylene group, a naphthylene group, a biphenylene group, a fluorenediyl group, and the like. In the case where the amylene group has a substituent, as the substituent, an alkyl group having 1 to 6 carbon atoms, a cycloalkyl group having 3 to 6 carbon atoms, or an aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 6 carbon atoms include a cyclopropyl group, a cyclobutyl group, a cyclopentyl group, a cyclohexyl group, and the like. Specific examples of the aryl group having 6 to 12 carbon atoms are a phenyl group, a naphthyl group, a biphenyl group, and the like.

As a benzo[a]anthracene compound of this embodiment, a benzo[a]anthracene compound having a structure in which a carbazolyl group is bonded to a benzo[a]anthracene skeleton via a substituted or unsubstituted phenylene group or a substituted or unsubstituted biphenyldiyl group can have improved stability and be synthesized with higher purity, which is preferable. Because the benzo[a]anthracene compound has an excellent carrier-transport property, a light-emitting element including the compound can be driven at a low voltage, which is preferable.

As a benzo[a]anthracene compound of this embodiment, a benzo[a]anthracene compound having a structure in which a carbazolyl group is bonded to a benzo[a]anthracene skeleton via a substituted or unsubstituted m-phenylene group has a wide band gap, and therefore can suitably be used especially in a light-emitting element that emits light with high energy such as blue light, which is preferable.

Example 4 of Compound

In the benzo[a]anthracene compound of this embodiment, the carbazolyl group is preferably bonded to the benzo[a]anthracene via a substituted or unsubstituted p-phenylene group, in which case the benzo[a]anthracene compound can have improved stability and can be synthesized with higher purity. The above-described benzo[a]anthracene compound is the benzo[a]anthracene compound represented by the following general formula (G4) or (G5).

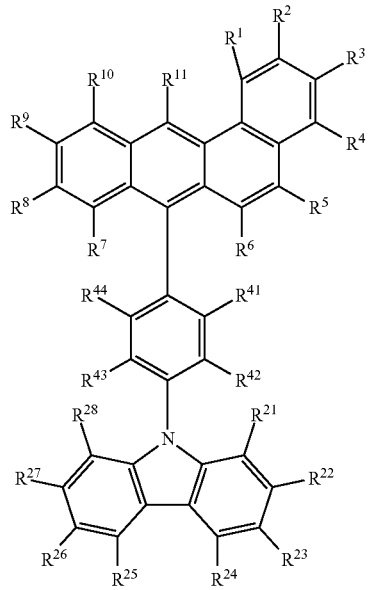

(G4)

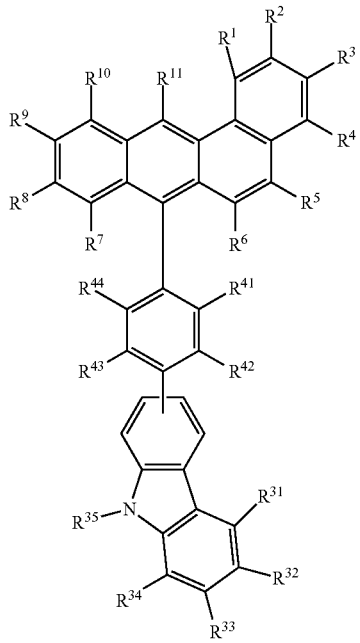

(G5)

In the above general formula (G4), $R^1$ to $R^{10}$, $R^{21}$ to $R^{28}$, and $R^{41}$ to $R^{44}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms. Furthermore, $R^{11}$ represents any of hydrogen, an alkyl group having 1 to 6 carbon atoms, a cycloalkyl group having 3 to 6 carbon atoms, and a substituted or unsubstituted phenyl group. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 6 carbon atoms include a cyclopropyl group, a cyclobutyl group, a cyclopentyl group, a cyclohexyl group, and the like. Specific examples of the aryl group having 6 to 13 carbon atoms are a phenyl group, a naphthyl group, a biphenyl group, a fluorenyl group, and the like. The above aryl group or phenyl group may include one or more substituents, and the substituents may be bonded to each other to form a ring. As the substituent, an alkyl group having 1 to 6 carbon atoms, a cycloalkyl group having 3 to 6 carbon atoms, or an aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 6 carbon atoms include a cyclopropyl group, a cyclobutyl group, a cyclopentyl group, a cyclohexyl group, and the like. Specific examples of the aryl group having 6 to 12 carbon atoms include a phenyl group, a naphthyl group, a biphenyl group, and the like. Note that $R^1$, $R^2$, $R^3$, $R^4$, $R^6$, $R^7$, $R^8$, $R^9$, and $R^{10}$ are each preferably hydrogen in that synthesis becomes easy and the advantage in material cost can be obtained.

In the above general formula (G5), $R^1$ to $R^{10}$, $R^{31}$ to $R^{35}$, and $R^{41}$ to $R^{44}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms. Furthermore, $R^{11}$ represents any of hydrogen, an alkyl group having 1 to 6 carbon atoms, a cycloalkyl group having 3 to 6 carbon atoms, and a substituted or unsubstituted phenyl group. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 6 carbon atoms include a cyclopropyl group, a cyclobutyl group, a cyclopentyl group, a cyclohexyl group, and the like. Specific examples of the aryl group having 6 to 13 carbon atoms are a phenyl group, a naphthyl group, a biphenyl group, a fluorenyl group, and the like. The above aryl group or phenyl group may include one or more substituents, and the substituents may be bonded to each other to form a ring. As the substituent, an alkyl group having 1 to 6 carbon atoms, a cycloalkyl group having 3 to 6 carbon atoms, or an aryl group having 6 to 12 carbon atoms can also be selected. Specific examples of the alkyl group having 1 to 6 carbon atoms include a methyl group, an ethyl group, a propyl group, an isopropyl group, a butyl group, an isobutyl group, a tert-butyl group, an n-hexyl group, and the like. Specific examples of a cycloalkyl group having 3 to 6 carbon atoms include a cyclopropyl group, a cyclobutyl group, a cyclopentyl group, a cyclohexyl group, and the like. Specific examples of the aryl group having 6 to 12 carbon atoms include a phenyl group, a naphthyl group, a biphenyl group, and the like. Note that $R^1$, $R^2$, $R^3$, $R^4$, $R^6$, $R^7$, $R^8$, $R^9$, and $R^{10}$ are each preferably hydrogen in that synthesis becomes easy and the advantage in material cost can be obtained.

Examples of Substituents

As the carbazolyl group represented by Ar in the general formula (G1), for example, groups represented by structure formulae (Cz-1) to (Cz-7) below can be used. Note that the group that can be used as A is not limited to these.
(Cz-1)
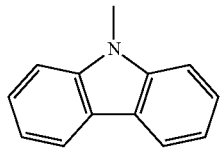
(Cz-2)
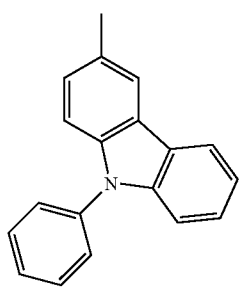
(Cz-3)
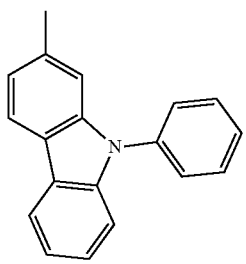
(Cz-4)
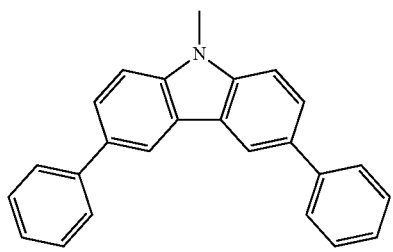
(Cz-5)
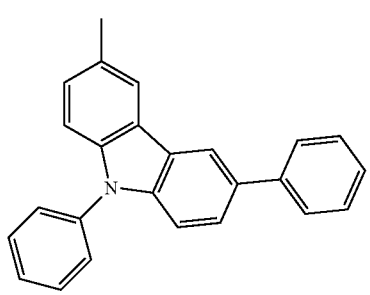
(Cz-6)
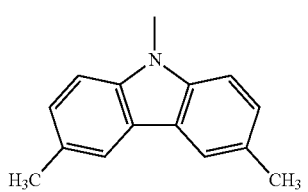
(Cz-7)
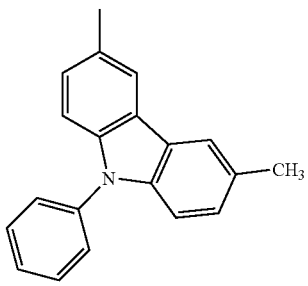
As the arylene group represented by Ar in the above general formulae (G1) to (G3), for example, groups represented by structure formulae (Ar-1) to (Ar-18) below can be used. Note that the group that can be used as Ar is not limited to these.
(Ar-1)
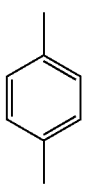
(Ar-2)
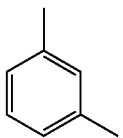
(Ar-3)
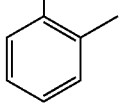
(Ar-4)
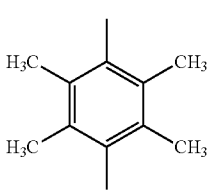
(Ar-5)
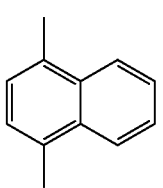
(Ar-6)

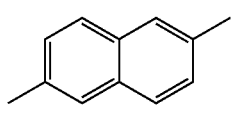
(Ar-7)
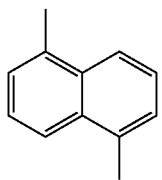
(Ar-8)
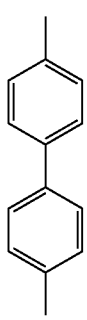
(Ar-9)
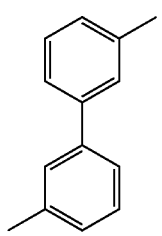
(Ar-10)
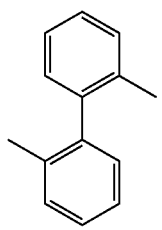
(Ar-11)
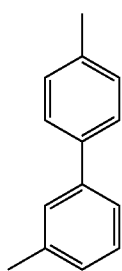
(Ar-12)
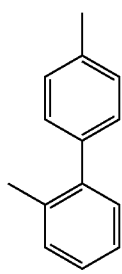
(Ar-13)
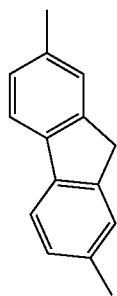
(Ar-14)
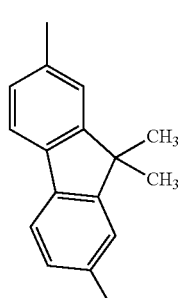
(Ar-15)
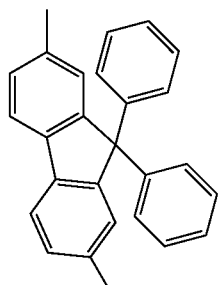
(Ar-16)
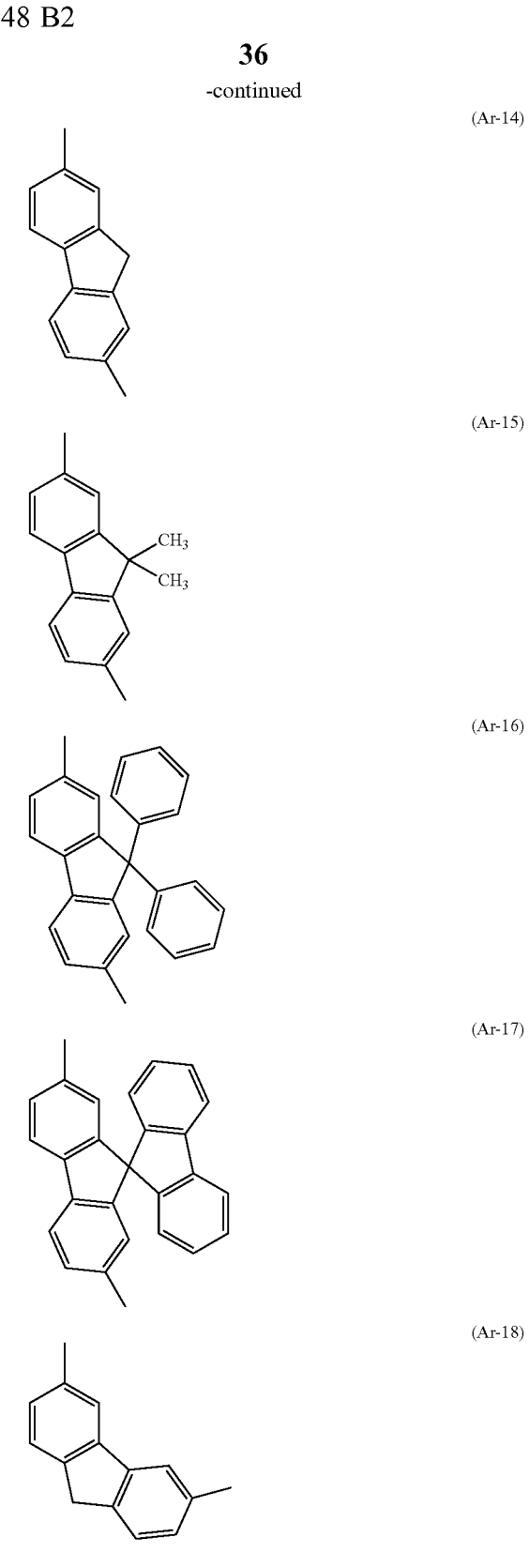
(Ar-17)
(Ar-18)
For example, groups represented by structure formulae (R-1) to (R-29) below can be used as the alkyl group or aryl group represented by any of $R^1$ to $R^{10}$ in the above general formulae (G1) to (G5), $R^{21}$ to $R^{28}$ in the above general formulae (G2) and (G4), $R^{31}$ to $R^{35}$ in the above general formulae (G3) and (G5), and $R^{41}$ to $R^{44}$ in the above general formulae (G4) and (G5). Note that the group which can be used as an alkyl group or an aryl group are not limited thereto.
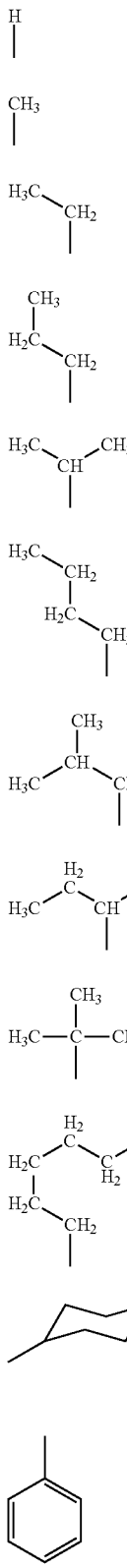
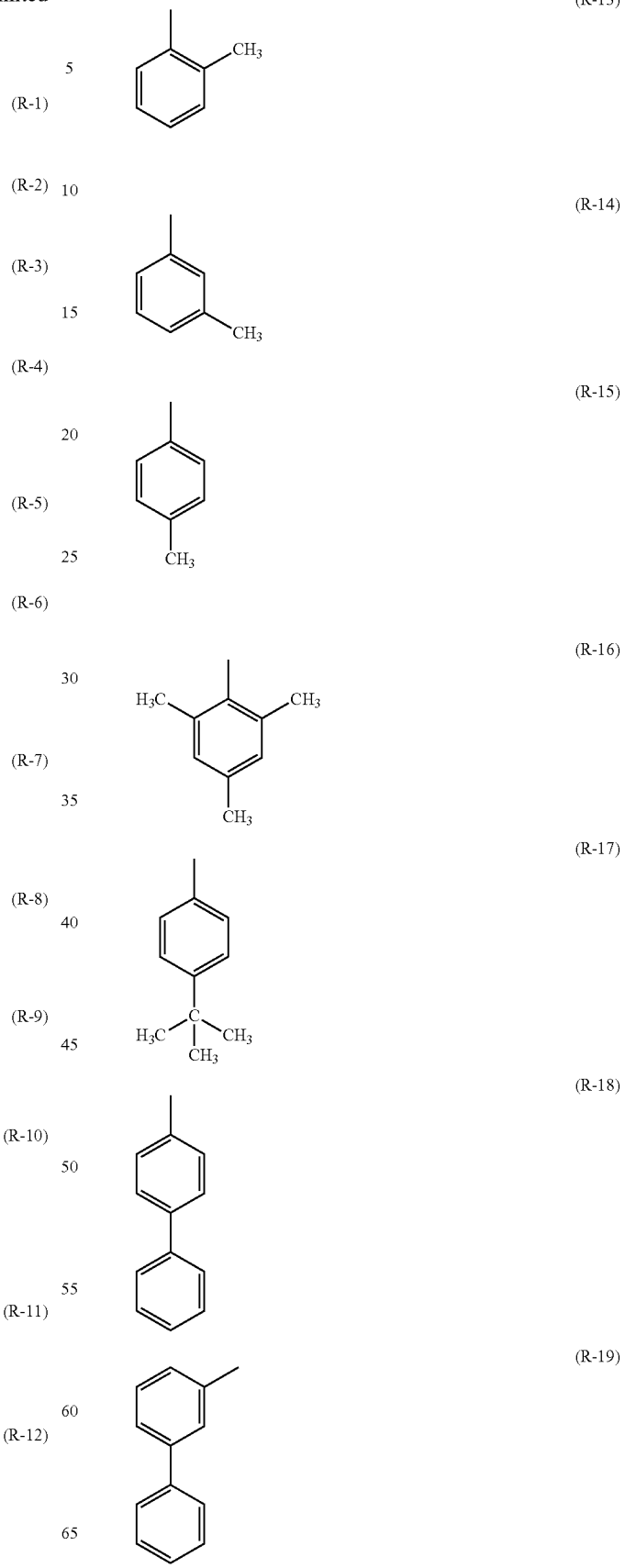

(R-20) 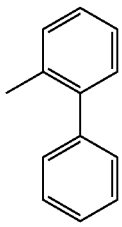

(R-21) 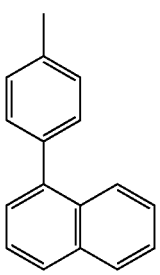

(R-22) 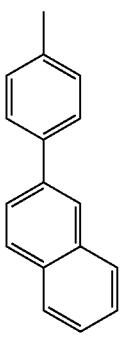

(R-23) 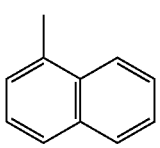

(R-24) 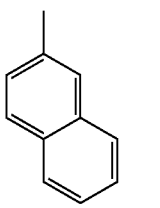

(R-25) 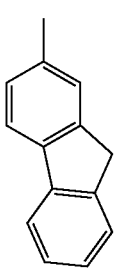

(R-26) 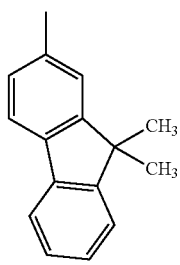

(R-27) 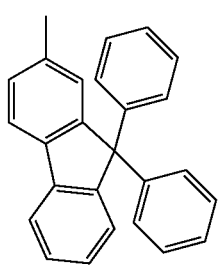

(R-28) 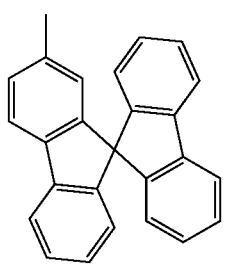

(R-29) 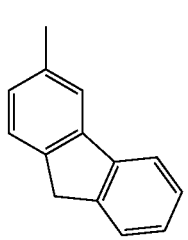

As the alkyl group or phenyl group represented by $R^{11}$ in the above general formulae (G1) to (G5), for example, groups represented by the above structure formulae (R-1) to (R-22) can be used. Note that groups which can be used as an alkyl group or a phenyl group are not limited thereto.

Specific Examples of Compounds

Specific examples of structures of the benzo[a]anthracene compounds represented by the above general formulae (G1) to (G5) are represented by structure formulae (100) to (125) below, and the like. Note that the benzo[a]anthracene compounds represented by the above general formulae (G1) to (G5) are not limited to the following examples.

-continued
(100)
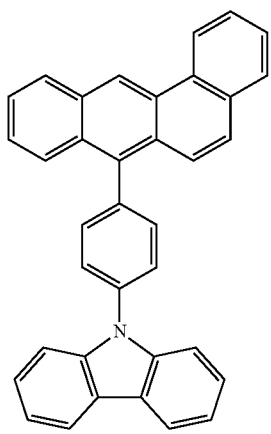
(101)
(102)
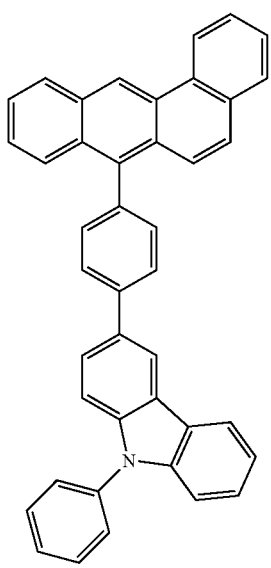
(103)
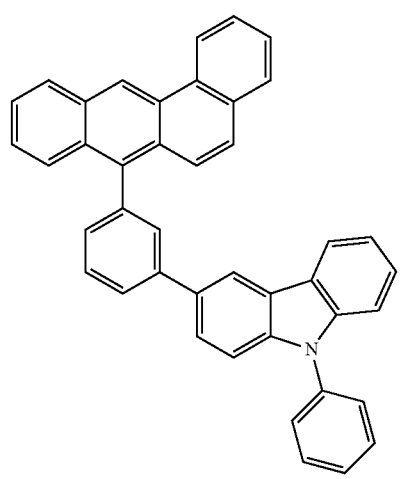
(104)
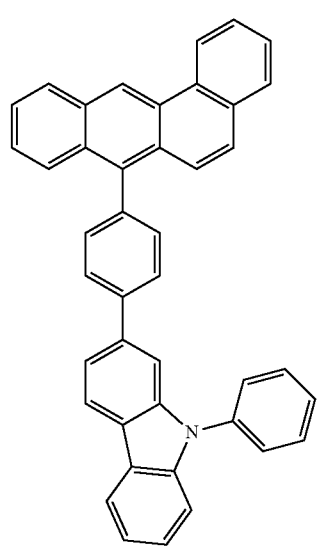
(105)
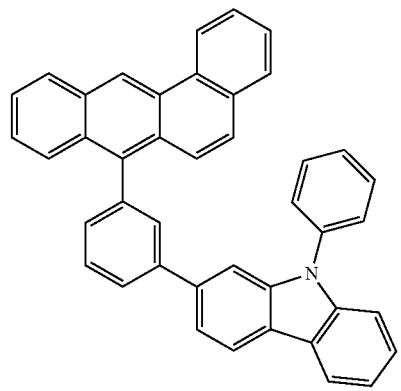

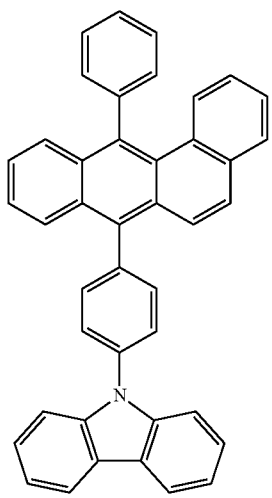
(106)
(107)
(108)
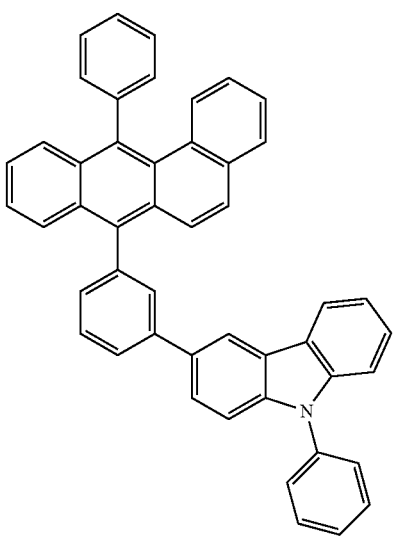
(109)
(110)
(111)

(112)
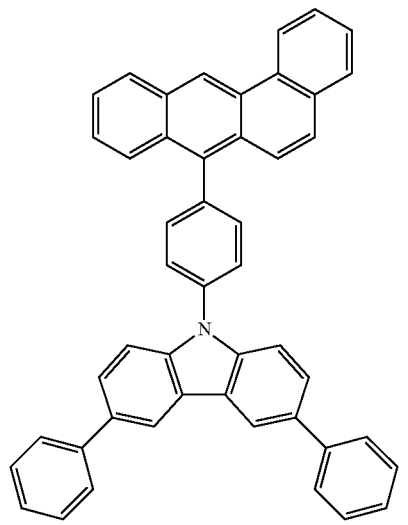
(113)
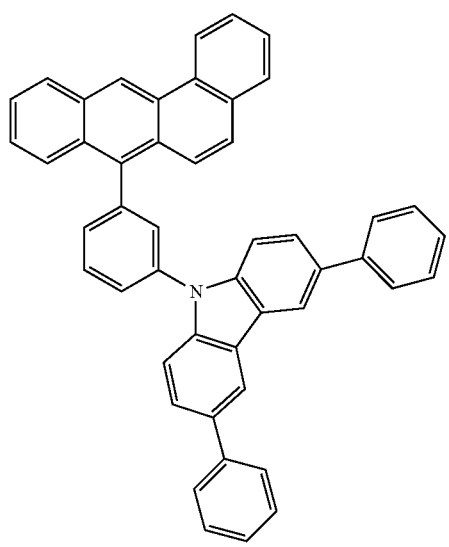
(114)
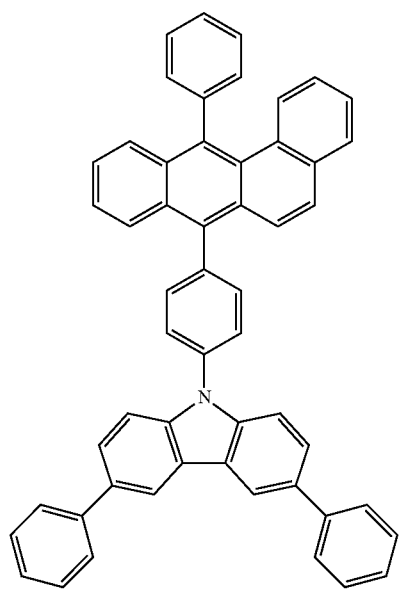
(115)
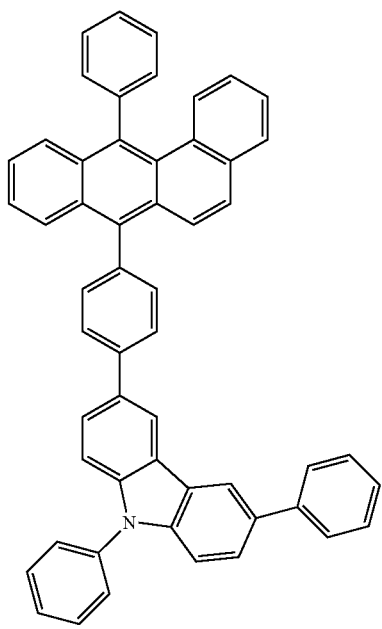
(116)
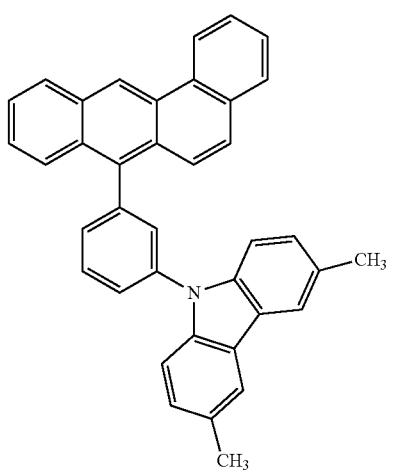
(117)
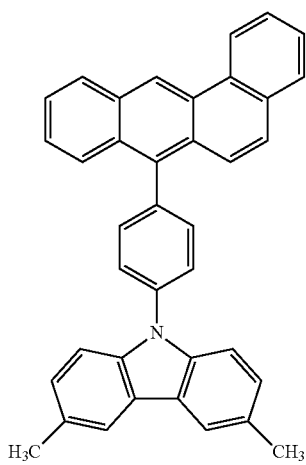

(118)
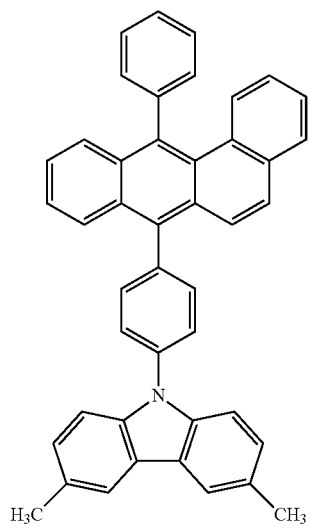
(119)
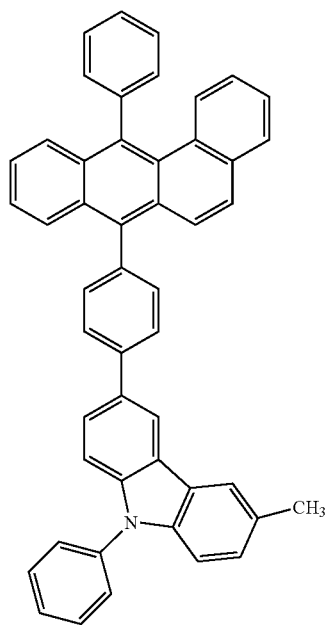
(120)
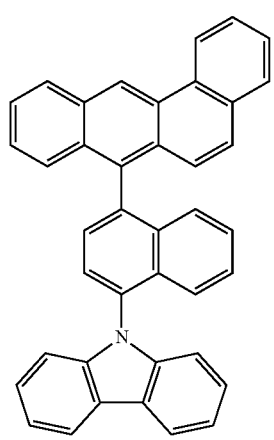
(121)
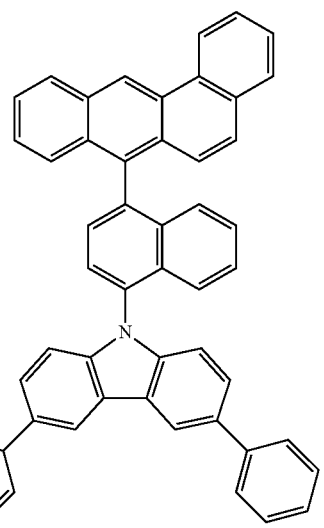
(122)
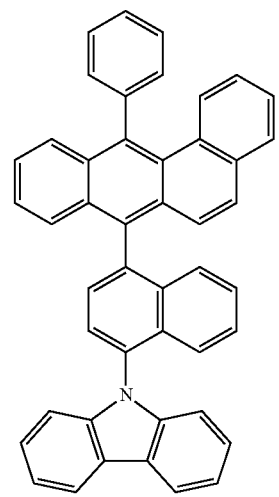
(123)
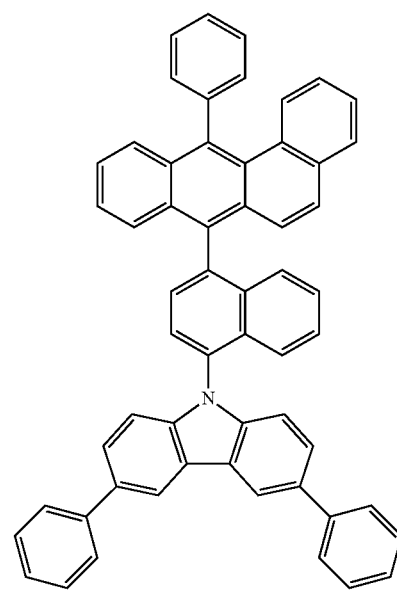

-continued

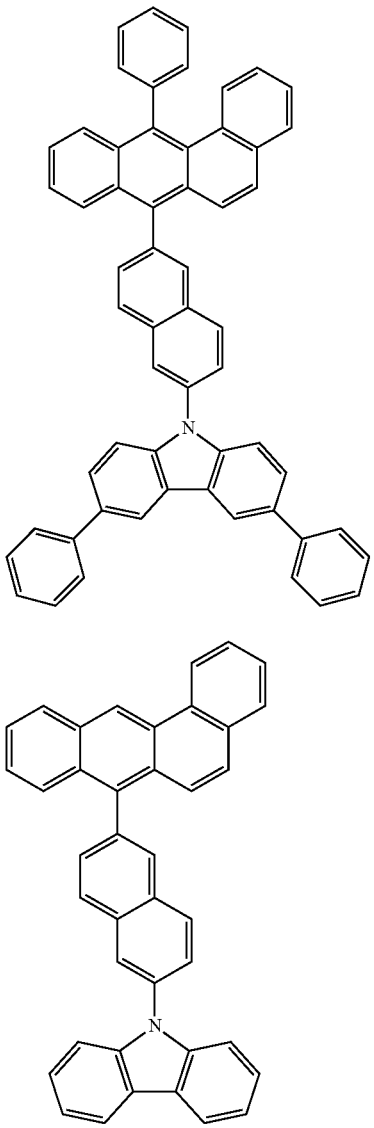

(124)

(125)

Since a delayed fluorescence component due to TTA accounts for a large proportion in a benzo[a]anthracene compound of this embodiment as described above, the benzo[a]anthracene compound can suitably be used as a host material in a light-emitting element; a light-emitting element with high emission efficiency can thus be fabricated. A benzo[a]anthracene compound of this embodiment has a wide band gap and can suitably be used as a host material or a carrier-transport material particularly in a blue light-emitting element; a blue light-emitting element with high emission efficiency can thus be fabricated. A benzo[a]anthracene compound of this embodiment has an excellent carrier-transport property and can suitably be used as a host material or a carrier-transport material in a light-emitting element; a light-emitting element that can be driven at a low voltage can thus be fabricated. In addition, since a benzo[a]anthracene compound of this embodiment is highly resistant to repetition of oxidation and reduction, use of the benzo[a]anthracene compound in a light-emitting element enables the long operating life of the light-emitting element. As described above, a benzo[a]anthracene compound of this embodiment is a material suitable for a light-emitting element.

A film of a benzo[a]anthracene compound of this embodiment can be formed by an evaporation method (including a vacuum evaporation method), an inkjet method, a coating method, gravure printing, or the like.

Note that the compound described in this embodiment can be used in combination with any of the structures described in the other embodiments as appropriate.

Embodiment 3

In this embodiment, a method of synthesizing the benzo[a]anthracene compound represented by the general formula (G1) is described. As the method of synthesizing the benzo[a]anthracene compound, a variety of reactions can be employed. For example, the benzo[a]anthracene compound represented by the general formula (G1) can be synthesized by a synthesis reaction shown below, for example. Note that the method of synthesizing the benzo[a]anthracene compound which is one embodiment of the present invention is not limited to the following synthesis method.

The compound represented by the general formula (G1) can be synthesized as in the synthesis scheme (A-1) below. Specifically, a benzo[a]anthracene compound (a1) and an aryl compound (a2) are coupled, whereby the compound represented by the general formula (G1) can be obtained.

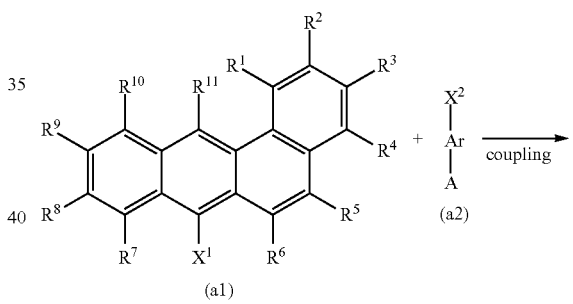

(A-1)

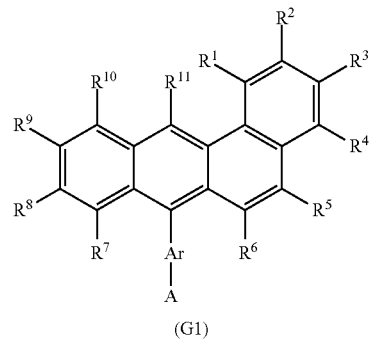

(G1)

In the synthesis scheme (A-1), A represents a substituted or unsubstituted carbazolyl group, and $X^1$ and $X^2$ each independently represent a halogen group, a trifluoromethanesulfonyl group, a boronic acid group, an organoboron group, a halogenated magnesium group, an organotin group, or the like. In the case where $X^1$ represents a halogen group or a trifluoromethanesulfonyl group, $X^2$ represents a boronic acid group, an organoboron group, a halogenated magnesium group, an organotin group, or the like. In the case where $X^1$ represents a boronic acid group, an organoboron group, a halogenated magnesium group, or an organotin group, $X^2$ represents a halogen group or a trifluoromethanesulfonyl group.

In the synthesis scheme (A-1), $R^1$ to $R^{10}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms, $R^{11}$ represents any of hydrogen, an alkyl group having 1 to 6 carbon atoms, a cycloalkyl group having 3 to 6 carbon atoms, and a substituted or unsubstituted phenyl group, and Ar represents an arylene group having 6 to 13 carbon atoms. The arylene group may include one or more substituents and the substituents may be bonded to each other to form a ring.

When a Suzuki-Miyaura coupling reaction using a palladium catalyst is performed in a synthesis scheme (A-1), $X^1$ and $X^2$ each independently represent a halogen group, a boronic acid group, an organoboron group, or a trifluoromethanesulfonyl group, and the halogen group is preferably, iodine, bromine, or chlorine. In the reaction, a palladium compound such as bis(dibenzylideneacetone)palladium(0), palladium(II) acetate, [1,1'-bis(diphenylphosphino)ferrocene]palladium(II) dichloride, or tetrakis(triphenylphosphine)palladium(0) and a ligand such as tri(tert-butyl)phosphine, tri(n-hexyl)phosphine, tricyclohexylphosphine, di(1-adamantyl)-n-butylphosphine, 2-dicyclohexylphosphino-2',6'-dimethoxybiphenyl, or tri(ortho-tolyl)phosphine can be used. In addition, in the reaction, an organic base such as sodium tert-butoxide, an inorganic base such as potassium carbonate, cesium carbonate, or sodium carbonate, or the like can be used. In the reaction, toluene, xylene, benzene, mesitylene, tetrahydrofuran, dioxane, ethanol, methanol, water, or the like can be used as a solvent. Reagents that can be used in the reaction are not limited thereto.

The reaction performed in the synthesis scheme (A-1) is not limited to a Suzuki-Miyaura coupling reaction, and a Migita-Kosugi-Stille coupling reaction using an organotin compound, a Kumada-Tamao-Corriu coupling reaction using a Grignard reagent, a Negishi coupling reaction using an organozinc compound, or the like can also be employed.

In the above-described manner, the benzo[a]anthracene compound represented by the general formula (G1) can be synthesized.

Note that this embodiment can be used in combination with any of the structures described in the other embodiments as appropriate.

Embodiment 4

In this embodiment, structure examples of a light-emitting element including the benzo[a]anthracene compound in Embodiment 2 are described below with reference to FIG. 3, FIG. 4, and FIGS. 5A and 5B.

Structure Example 1 of Light-Emitting Element

Figure 3:
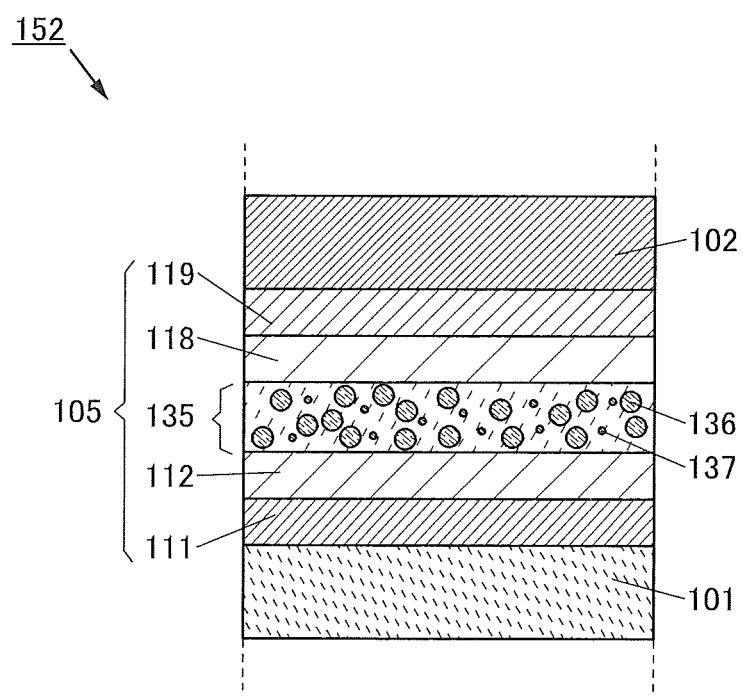
FIG. 3 is a schematic cross-sectional view of a light-emitting element according to one embodiment of the present invention.

In FIG. 3, a light-emitting element 152 includes an EL layer 105 between a pair of electrodes, and any of the layers in the EL layer 105 includes the benzo[a]anthracene compound described in Embodiment 2.

The EL layer 105 can include the hole-injection layer 111, the hole-transport layer 112, the electron-transport layer 118, and the electron-injection layer 119 which are described in Embodiment 1, in addition to a light-emitting layer 135. The stacked layer structure of the EL layer 105 is not limited thereto.

The materials described in Embodiment 1 can be used for the pair of electrodes (electrodes 101 and 102), the hole-injection layer 111, the hole-transport layer 112, the electron-transport layer 118, and the electron-injection layer 119 in this embodiment. As a guest material 137 in the light-emitting layer 135, the material for the guest material 132 which is described in Embodiment 1 can be used.

The benzo[a]anthracene compound described in Embodiment 2, in which a delayed fluorescence component due to TTA accounts for a large proportion of emitted light, is suitable particularly for the host material 136 in the light-emitting element 152. When the benzo[a]anthracene compound described in Embodiment 2 is used as the host material 136 in the light-emitting element 152, a light-emitting element with high emission efficiency can be fabricated. A light-emitting element including the benzo[a]anthracene compound in which a delayed fluorescence component accounts for 20% or more of light emitted from the EL layer 105 can be fabricated. Furthermore, the benzo[a]anthracene compound having a wide band gap is suitable for a host material or a carrier-transport material particularly in a blue light-emitting element. Thus, the structure of this embodiment can provide a light-emitting element with high emission efficiency and an emission spectrum peak in the blue wavelength range. Furthermore, the benzo[a]anthracene compound having an excellent carrier-transport property is suitable for a host material or a carrier-transport material in a light-emitting element. Thus, the structure of this embodiment can provide a light-emitting element that can be driven at a low voltage. The benzo[a]anthracene compound, which is highly resistant to repetition of oxidation and reduction, can provide a light-emitting element having a long operating life.

Structure Example 2 of Light-Emitting Element

Next, a structure example different from the light-emitting element illustrated in FIG. 3 is described below with reference to FIG. 4.

Figure 4:
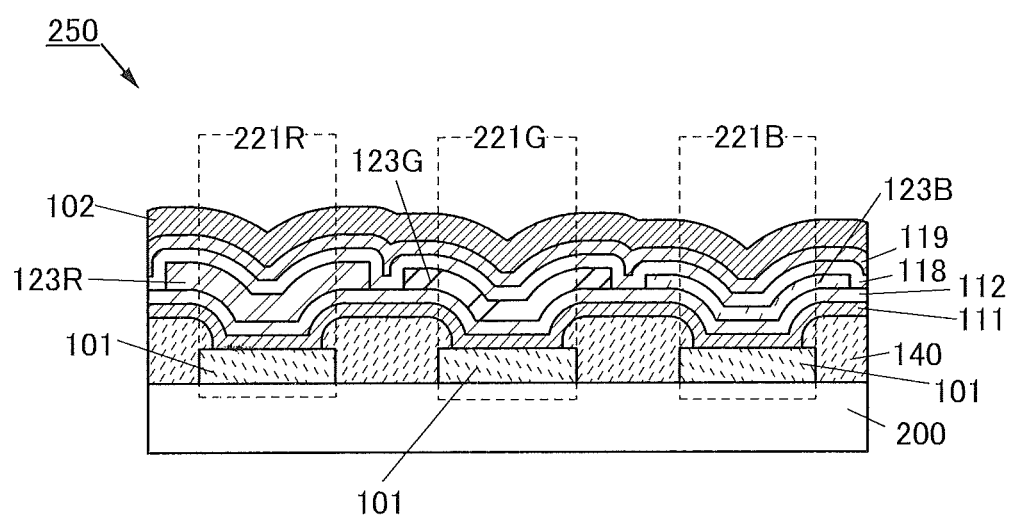
FIG. 4 is a schematic cross-sectional view of a light-emitting element according to one embodiment of the present invention.

FIG. 4 is a cross-sectional view illustrating a light-emitting element of one embodiment of the present invention. In FIG. 4, a portion having a function similar to that in FIG. 3 is represented by the same hatch pattern as in FIG. 3 and not especially denoted by a reference numeral in some cases. In addition, common reference numerals are used for portions having similar functions, and a detailed description of the portions is omitted in some cases.

A light-emitting element 250 in FIG. 4 has a bottom-emission structure in which light is extracted through the substrate 200. However, one embodiment of the present invention is not limited to this structure and may have a top-emission structure in which light emitted from the light-emitting element is extracted in the direction opposite to the substrate 200 or a dual-emission structure in which light emitted from the light-emitting element is extracted in both top and bottom directions of the substrate 200 over which the light-emitting element is formed.

The light-emitting element 250 includes the electrode 101 and the electrode 102 over the substrate 200. Between the electrodes 101 and 102, a light-emitting layer 123B, a light-emitting layer 123G, and a light-emitting layer 123R are provided. The hole-injection layer 111, the hole-transport layer 112, the electron-transport layer 118, and the electron-injection layer 119 are also provided.

In the case where the light-emitting element has a bottom emission structure, the electrode 101 preferably has a function of transmitting light and the electrode 102 preferably has a function of reflecting light.

In the light-emitting element 250 illustrated in FIG. 4, a partition 140 is present between a region 221B and a region 221G and between the region 221G and a region 221R, in each of which the components are interposed between the electrodes 101 and 102. The partition 140 has an insulating property. The partition 140 covers an end portion of the electrode 101 and has openings overlapping with the electrodes. With the partition 140, the electrode 101 in the regions over the substrate 200 can have the shape of separate islands.

The light-emitting layers 123B, 123G, and 123R preferably include light-emitting materials having functions of emitting light of different colors. For example, with the light-emitting layer 123B including a light-emitting material having a function of emitting blue light, the light-emitting layer 123G including a light-emitting material having a function of emitting green light, and the light-emitting layer 123R including a light-emitting material having a function of emitting red light, the light-emitting element 250 can be used in a display device capable of full-color display. The thicknesses of the light-emitting layers may be the same or different.

At least one of the light-emitting layers 123B, 123G, and 123R preferably includes the benzo[a]anthracene compound described in Embodiment 2, in which case a light-emitting element including a region in which the delayed fluorescence component accounts for 20% or more of light emitted from the light-emitting layers can be fabricated. The use of the benzo[a]anthracene compound described in Embodiment 2 especially in the light-emitting layer 123B enables a light-emitting element with high emission efficiency and an emission spectrum peak in the blue wavelength range.

One or more of the light-emitting layers 123B, 123G, and 123R may include two or more stacked layers.

When at least one light-emitting layer includes the benzo[a]anthracene compound described in Embodiment 2 as described above and the light-emitting element 250 including the light-emitting layer is used in each sub-pixel of pixels in a display device, the display device can have high emission efficiency. The display device including the light-emitting element 250 can thus have reduced power consumption.

Structure Examples 3 of Light-Emitting Element

Next, structure examples different from the light-emitting element illustrated in FIG. 3 and FIG. 4 are described below with reference to FIGS. 5A and 5B.

FIGS. 5A and 5B are cross-sectional views illustrating light-emitting elements of one embodiment of the present invention. In FIGS. 5A and 5B, a portion having a function similar to those in FIG. 3 and FIG. 4 is represented by the same hatch pattern as in FIG. 3 and FIG. 4 and not especially denoted by a reference numeral in some cases. In addition, common reference numerals are used for portions having similar functions, and a detailed description of the portions is omitted in some cases.

FIGS. 5A and 5B each illustrate a structure example of a tandem light-emitting element in which a plurality of light-emitting layers are stacked between a pair of electrodes with a charge-generation layer 115 provided between the light-emitting layers. A light-emitting element 252 illustrated in FIG. 5A has a top-emission structure in which light is extracted in a direction opposite to the substrate 200, and a light-emitting element 254 illustrated in FIG. 5B has a bottom-emission structure in which light is extracted to the substrate 200 side. However, one embodiment of the present invention is not limited to these structures and may have a dual-emission structure in which light emitted from the light-emitting element is extracted in both top and bottom directions of the substrate 200 over which the light-emitting element is formed.

The light-emitting elements 252 and 254 each include the electrode 101, the electrode 102, an electrode 103, and an electrode 104 over the substrate 200. A light-emitting layer 160, the charge-generation layer 115, and a light-emitting layer 170 are provided between the electrode 101 and the electrode 102, between the electrode 102 and the electrode 103, and between the electrode 102 and the electrode 104. The hole-injection layer 111, the hole-transport layer 112, the electron-transport layer 113, the electron-injection layer 114, the hole-injection layer 116, the hole-transport layer 117, the electron-transport layer 118, and the electron-injection layer 119 are further provided.

The electrode 101 includes a conductive layer 101a and a conductive layer 101b on and in contact with the conductive layer 101a. The electrode 103 includes a conductive layer 103a and a conductive layer 103b on and in contact with the conductive layer 103a. The electrode 104 includes a conductive layer 104a and a conductive layer 104b on and in contact with the conductive layer 104a.

In the light-emitting element 252 illustrated in FIG. 5A and the light-emitting element 254 illustrated in FIG. 5B, the partition 140 is present between a region 222B in which the components are interposed between the electrodes 101 and 102 and a region 222G in which the components are interposed between the electrodes 102 and 103. The partition 140 is present also between the region 222G and a region 222R in which the components are interposed between the electrodes 102 and 104. The partition 140 has an insulating property. The partition 140 covers end portions of the electrodes 101, 103, and 104 and has openings overlapping with the electrodes. With the partition 140, the electrodes in the regions over the substrate 200 can have the shape of separate islands.

The light-emitting elements 252 and 254 each include a substrate 220 provided with an optical element 224B, an optical element 224G, and an optical element 224R in the direction in which light emitted from the region 222B, light emitted from the region 222G, and light emitted from the region 222R are extracted. The light emitted from each region is emitted outside the light-emitting element through each optical element. In other words, the light from the region 222B, the light from the region 222G, and the light from the region 222R are emitted through the optical element 224B, the optical element 224G, and the optical element 224R, respectively.

The optical elements 224B, 224G, and 224R each have a function of selectively transmitting light of a particular color out of incident light. For example, the light emitted from the region 222B through the optical element 224B is blue light, the light emitted from the region 222G through the optical element 224G is green light, and the light emitted from the region 222R through the optical element 224R is red light.

Note that in FIGS. 5A and 5B, blue light (B), green light (G), and red light (R) emitted from the regions through the optical elements are schematically illustrated by the arrows of dashed lines.

A light-blocking layer 223 is provided between the optical elements. The light-blocking layer 223 has a function of blocking light emitted from the adjacent regions. Note that a structure without the light-blocking layer 223 may also be employed.

<<Microcavity>>

Furthermore, the light-emitting elements 252 and 254 each have a microcavity structure.

Light emitted from the light-emitting layers 160 and 170 resonates between a pair of electrodes (e.g., the lower electrode 101 and the upper electrode 102). In each of the light-emitting elements 252 and 254, the thicknesses of the conductive layers (the conductive layer 101b, the conductive layer 103b, and the conductive layer 104b) in each region are adjusted so that the wavelength of light emitted from the light-emitting layers 160 and 170 can be intensified. Note that the thickness of at least one of the hole-injection layer 111 and the hole-transport layer 112 may differ between the regions so that the wavelength of light emitted from the light-emitting layers 160 and 170 is intensified.

For example, in the case where the refractive index of the conductive material having a function of reflecting light in the electrodes 101 to 104 is lower than the refractive index of the light-emitting layer 160 or 170, the thickness of the conductive layer 101b of the electrode 101 is adjusted so that the optical path length between the electrode 101 and the electrode 102 is $m_B \lambda_B/2$ ($m_B$ is a natural number and 4 is a wavelength of light which is intensified in the region 222B). Similarly, the thickness of the conductive layer 103b of the electrode 103 is adjusted so that the optical path length between the electrode 103 and the electrode 102 is $m_G \lambda_G/2$ ($m_G$ is a natural number and $\lambda_G$ is a wavelength of light which is intensified in the region 222G). Furthermore, the thickness of the conductive layer 104b of the electrode 104 is adjusted so that the optical path length between the electrode 104 and the electrode 102 is $m_R \lambda_R/2$ ($m_R$ is a natural number and $\lambda_R$ is a wavelength of light which is intensified in the region 222R).

In the above manner, with the microcavity structure, in which the optical path length between the pair of electrodes in the respective regions is adjusted, scattering and absorption of light in the vicinity of the electrodes can be suppressed, resulting in high light extraction efficiency. In the above structure, each of the conductive layers 101b, 103b, and 104b preferably has a function of transmitting light. The materials of the conductive layers 101b, 103b, and 104b may be the same or different. The conductive layers 101b, 103b, and 104b may each have two or more stacked layers.

Note that since the light-emitting element 252 illustrated in FIG. 5A has a top-emission structure, it is preferable that the conductive layer 101a of the electrode 101, the conductive layer 103a of the electrode 103, and the conductive layer 104a of the electrode 104 have a function of reflecting light. In addition, it is preferable that the electrode 102 have functions of transmitting light and reflecting light.

Since the light-emitting element 254 illustrated in FIG. 5B has a bottom-emission structure, it is preferable that the conductive layer 101a of the electrode 101, the conductive layer 103a of the electrode 103, and the conductive layer 104a of the electrode 104 have functions of transmitting light and reflecting light. In addition, it is preferable that the electrode 102 have a function of reflecting light.

Materials used for the conductive layers 101a, 103a, and 104a may be the same or different in each of the light-emitting elements 252 and 254. When the conductive layers 101a, 103a, and 104a are formed using the same materials, manufacturing cost of the light-emitting elements 252 and 254 can be reduced. The conductive layers 101a, 103a, and 104a may each have two or more stacked layers.

At least one of the light-emitting layers 160 and 170 preferably includes the benzo[a]anthracene compound described in Embodiment 2, in which case a light-emitting element including a region in which the delayed fluorescence component accounts for 20% or more of light emitted from the light-emitting layers can be fabricated. Particularly in the region 222B, the light-emitting element can have high emission efficiency and an emission spectrum peak in the blue wavelength range.

The light-emitting layers 160 and 170 can each have a stacked-layer structure of two layers, for example, a light-emitting layer 170a and a light-emitting layer 170b. Two kinds of light-emitting materials (a first compound and a second compound) having functions of emitting light of different colors are used in the two light-emitting layers, so that light of a plurality of emission colors can be obtained at the same time. It is particularly preferable to select light-emitting materials so that white light can be obtained by combining light emission from the light-emitting layers 160 and 170.

The light-emitting layer 160 or 170 may have a structure in which three or more layers are stacked or may include a layer containing no light-emitting material.

When at least one light-emitting layer includes the benzo[a]anthracene compound described in Embodiment 2 as described above and the light-emitting element 252 or 254 including the light-emitting layer is used in each of pixels in a display device, the display device can have high emission efficiency. The display device including the light-emitting element 252 or 254 can thus have reduced power consumption.

Note that the structure described in this embodiment can be combined as appropriate with any of the structures described in the other embodiments.

Embodiment 5

In this embodiment, light-emitting elements having structures different from those described in Embodiments 1 and 4 and emission mechanisms of the light-emitting elements are described below with reference to FIGS. 6A and 6B and FIGS. 7A and 7B.

Structure Example 1 of Light-Emitting Element

Figure 6A:
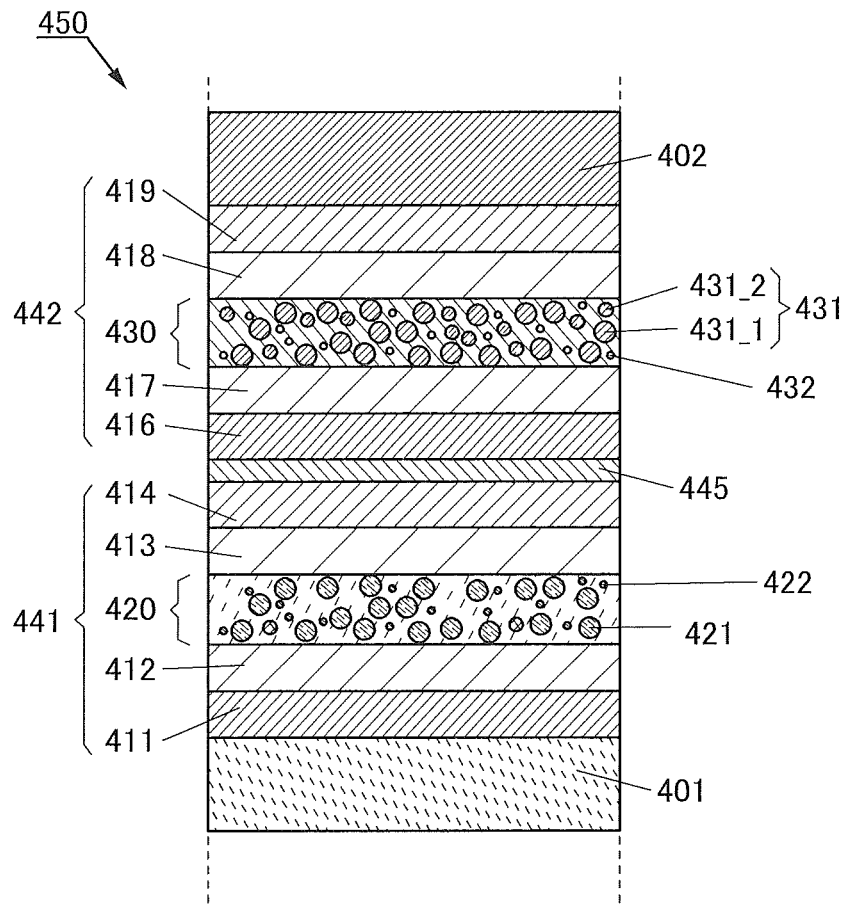
FIGS. 6A and 6B are a schematic cross-sectional view of a light-emitting element according to one embodiment of the present invention and a schematic diagram illustrating the correlation of energy levels.

FIG. 6A is a schematic cross-sectional view of a light-emitting element 450.

The light-emitting element 450 illustrated in FIG. 6A includes a plurality of light-emitting units (a light-emitting unit 441 and a light-emitting unit 442 in FIG. 6A) between a pair of electrodes (an electrode 401 and an electrode 402). One light-emitting unit has the same structure as the EL layer 100 illustrated in FIG. 1A or the EL layer 105 illustrated in FIG. 3. That is, the light-emitting element 150 in FIG. 1A and the light-emitting element 152 illustrated in FIG. 3 each include one light-emitting unit, while the light-emitting element 450 includes a plurality of light-emitting units. Note that the electrode 401 functions as an anode and the electrode 402 functions as a cathode in the following description of the light-emitting element 450; however, the functions may be interchanged in the light-emitting element 450.

In the light-emitting element 450 illustrated in FIG. 6A, the light-emitting unit 441 and the light-emitting unit 442 are stacked, and a charge-generation layer 445 is provided between the light-emitting unit 441 and the light-emitting unit 442. Note that the light-emitting unit 441 and the light-emitting unit 442 may have the same structure or different structures. For example, it is preferable that the EL layer 100 illustrated in FIG. 1A or the EL layer 105 illustrated in FIG. 3 be used in the light-emitting unit 441 and that a light-emitting layer containing a phosphorescent material as a light-emitting material be used in the light-emitting unit 442.

That is, the light-emitting element 450 includes a light-emitting layer 420 and a light-emitting layer 430. The light-emitting unit 441 includes a hole-injection layer 411, a hole-transport layer 412, an electron-transport layer 413, and an electron-injection layer 414 in addition to the light-emitting layer 420. The light-emitting unit 442 includes a hole-injection layer 416, a hole-transport layer 417, an electron-transport layer 418, and an electron-injection layer 419 in addition to the light-emitting layer 430.

The charge-generation layer 445 contains a composite material of an organic compound and an acceptor substance. For the composite material, the composite material that can be used for the hole-injection layer 111 described in Embodiment 1 may be used. As the organic compound, a variety of compounds such as an aromatic amine compound, a carbazole compound, an aromatic hydrocarbon, and a high molecular compound (such as an oligomer, a dendrimer, or a polymer) can be used. An organic compound having a hole mobility of $1 \times 10^{-6}$ cm$^2$/Vs or higher is preferably used. Note that any other material may be used as long as it has a property of transporting more holes than electrons. Since the composite material of an organic compound and an acceptor substance has excellent carrier-injection and carrier-transport properties, low-voltage driving or low-current driving can be realized. Note that when a surface of a light-emitting unit on the anode side is in contact with the charge-generation layer 445 as that of the light-emitting unit 442, the charge-generation layer 445 can also serve as a hole-injection layer or a hole-transport layer of the light-emitting unit; thus, a hole-injection layer or a hole-transport layer does need not be included in the light-emitting unit.

The charge-generation layer 445 may have a stacked-layer structure of a layer containing the composite material of an organic compound and an acceptor substance and a layer containing another material. For example, the charge-generation layer 445 may be formed using a combination of a layer containing the composite material of an organic compound and an acceptor substance with a layer containing one material selected from among materials having an electron donating property and a material having a high electron-transport property. Furthermore, the charge-generation layer 445 may be formed using a combination of a layer containing the composite material of an organic compound and an acceptor substance with a layer including a transparent conductive film.

The charge-generation layer 445 provided between the light-emitting unit 441 and the light-emitting unit 442 may have any structure as long as electrons can be injected to the light-emitting unit on one side and holes can be injected into the light-emitting unit on the other side when a voltage is applied between the electrode 401 and the electrode 402. For example, in FIG. 6A, the charge-generation layer 445 injects electrons into the light-emitting unit 441 and holes into the light-emitting unit 442 when a voltage is applied such that the potential of the electrode 401 is higher than that of the electrode 402.

The light-emitting element having two light-emitting units is described with reference to FIG. 6A; however, a similar structure can be applied to a light-emitting element in which three or more light-emitting units are stacked. With a plurality of light-emitting units partitioned by the charge-generation layer between a pair of electrodes as in the light-emitting element 450, it is possible to provide a light-emitting element which can emit light with high luminance with the current density kept low and has a long lifetime. A light-emitting element with low power consumption can be provided.

When the structure of the EL layer 100 or the EL layer 105 is applied to at least one of the plurality of units, a light-emitting element with high emission efficiency can be provided. In particular, use of a benzo[a]anthracene compound in at least one light-emitting layer can provide a light-emitting element with high emission efficiency.

The light-emitting layer 420 includes a host material 421 and a guest material 422. The light-emitting layer 430 includes a host material 431 and a guest material 432. The host material 431 includes an organic compound 431_1 and an organic compound 431_2.

In this embodiment, the light-emitting layer 420 has a structure similar to that of the light-emitting layer 130 in FIG. 1A or the light-emitting layer 135 illustrated in FIG. 3. That is, in the light-emitting layer 420, the host material 421 and the guest material 422 correspond to the host material 131 and the guest material 132, respectively, in the light-emitting layer 130, or alternatively correspond to the host material 136 and the guest material 137, respectively, in the light-emitting layer 135. In the following description, the guest material 432 included in the light-emitting layer 430 is a phosphorescent material. Note that the electrode 401, the electrode 402, the hole-injection layers 411 and 416, the hole-transport layers 412 and 417, the electron-transport layers 413 and 418, and the electron-injection layers 414 and 419 have functions similar to those of the electrode 101, the electrode 102, the hole-injection layer 111, the hole-transport layer 112, the electron-transport layer 118, and the electron-injection layer 119 in Embodiment 1, respectively. Therefore, detailed description thereof is omitted in this embodiment.

<Emission Mechanism of Light-Emitting Layer 420>

An emission mechanism of the light-emitting layer 420 is similar to that of the light-emitting layer 130 in FIG. 1A or the EL layer 135 in FIG. 3.

<Emission Mechanism of Light-Emitting Layer 430>

Next, an emission mechanism of the light-emitting layer 430 is described.

The organic compound 431_1 and the organic compound 431_2 which are included in the light-emitting layer 430 form an exciplex. The organic compound 431_1 serves as a host material and the organic compound 431_2 serves as an assist material in the description here.

Although it is acceptable as long as the combination of the organic compound 431_1 and the organic compound 431_2 can form an exciplex in the light-emitting layer 430, it is preferred that one organic compound be a material having a hole-transport property and the other organic compound be a material having an electron-transport property.

Figure 6B:
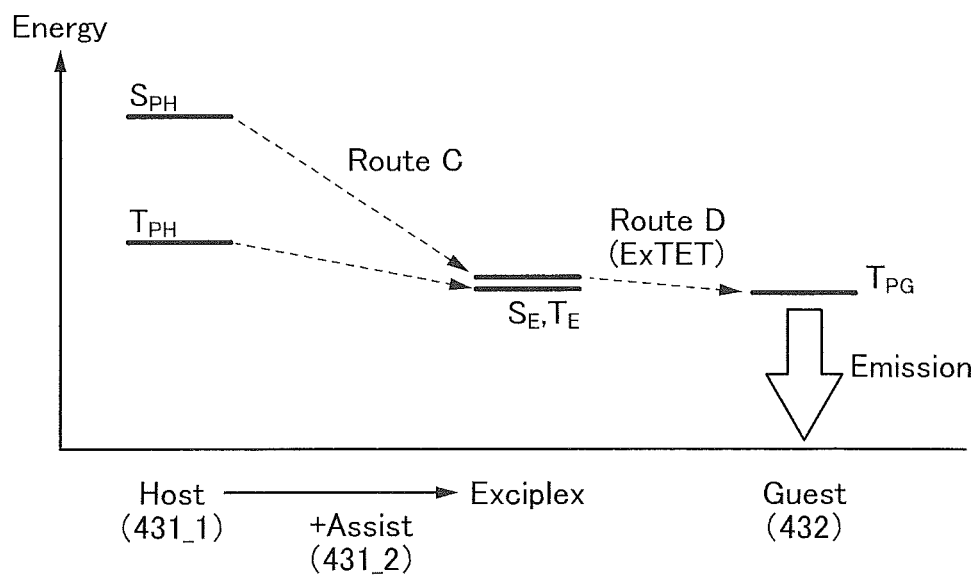

FIG. 6B illustrates the correlation of energy levels of the organic compound 431_1, the organic compound 431_2, and the guest material 432 in the light-emitting layer 430. What terms and signs in FIG. 6B are listed below.

Host (431_1): the organic compound 431_1 (host material)

Assist (431_2): the organic compound 431_2 (assist material)

Guest (432): the guest material 432 (phosphorescent material)

Exciplex: exciplex $S_{PH}$: the level of the lowest singlet excited state of the organic compound 431_1

$T_{PH}$: the level of the lowest triplet excited state of the organic compound 431_1

$T_{PG}$: the level of the lowest triplet excited state of the guest material 432 (phosphorescent material)

$S_E$: the level of the lowest singlet excited state of the exciplex $T_E$: the level of the lowest triplet excited state of the exciplex The level ($S_E$) of the lowest singlet excited state of the exciplex formed by the organic compounds 431_1 and 431_2 and the level ($T_E$) of the lowest triplet excited state of the exciplex are close to each other (see Route C in FIG. 6B).

Both energies of $S_E$ and $T_E$ of the exciplex are then transferred to the level of the lowest triplet excited state of the guest material 432 (phosphorescent material); thus, light emission is obtained (see Route D in FIG. 6B).

The above-described processes through Route C and Route D may be referred to as exciplex-triplet energy transfer (ExTET) in this specification and the like.

When one of the organic compounds 431_1 and 431_2 receiving holes and the other receiving electrons come close to each other, the exciplex is formed at once. Alternatively, when one compound is brought into an excited state, the one immediately interacts with the other compound to form the exciplex. Therefore, most excitons in the light-emitting layer 430 exist as exciplexes. The band gap of the exciplex is narrower than that of each of the organic compounds 431_1 and 431_2; therefore, the drive voltage can be lowered when the exciplex is formed by recombination of a hole and an electron.

When the light-emitting layer 430 has the above structure, light emission from the guest material 432 (phosphorescent material) of the light-emitting layer 430 can be efficiently obtained.

Note that light emitted from the light-emitting layer 420 preferably has a peak on the shorter wavelength side than light emitted from the light-emitting layer 430. Since the luminance of a light-emitting element using a phosphorescent material emitting light with a short wavelength tends to be degraded quickly, fluorescence with a short wavelength is employed so that a light-emitting element with less degradation of luminance can be provided.

Furthermore, the light-emitting layer 420 and the light-emitting layer 430 may be made to emit light with different emission wavelengths, so that the light-emitting element can be a multicolor light-emitting element. In that case, the emission spectrum of the light-emitting element is formed by combining light having different emission peaks, and thus has at least two peaks.

The above structure is also suitable for obtaining white light emission. When the light-emitting layer 420 and the light-emitting layer 430 emit light of complementary colors, white light emission can be obtained.

In addition, white light emission with a high color rendering property that is formed of three primary colors or four or more colors can be obtained by using a plurality of light-emitting materials emitting light with different wavelengths for one of the light-emitting layers 420 and 430 or both. In that case, one of the light-emitting layers 420 and 430 or both may be divided into layers and each of the divided layers may contain a light-emitting material different from the others.

<Material that can be Used in Light-Emitting Layers>

Next, materials that can be used in the light-emitting layers 420 and 430 are described.

<<<Material that can be Used in Light-Emitting Layer 420>

As a material that can be used in the light-emitting layer 420, a material that can be used in the light-emitting layer 130 in Embodiment 1 or the light-emitting layer 135 in Embodiment 4 may be used.

<<Material that can be Used in Light-Emitting Layer 430>>

In the light-emitting layer 430, the organic compound 431_1 (host material) exists in the highest proportion in weight ratio, and the guest material 432 (phosphorescent material) is dispersed in the organic compound 431_1 (host material).

Examples of the organic compound 431_1 (host material) include a zinc- or aluminum-based metal complex, an oxadiazole derivative, a triazole derivative, a benzimidazole derivative, a quinoxaline derivative, a dibenzoquinoxaline derivative, a dibenzothiophene derivative, a dibenzofuran derivative, a pyrimidine derivative, a triazine derivative, a pyridine derivative, a bipyridine derivative, a phenanthroline derivative, and the like. Other examples are an aromatic amine, a carbazole derivative, and the like.

As the guest material 432 (phosphorescent material), an iridium-, rhodium-, or platinum-based organometallic complex or metal complex can be used; in particular, an organoiridium complex such as an iridium-based ortho-metalated complex is preferable. As an ortho-metalated ligand, a 4H-triazole ligand, a 1H-triazole ligand, an imidazole ligand, a pyridine ligand, a pyrimidine ligand, a pyrazine ligand, an isoquinoline ligand, and the like can be given. As the metal complex, a platinum complex having a porphyrin ligand and the like can be given.

As the organic compound 431_2 (assist material), a substance which can form an exciplex together with the organic compound 431_1 is used. In that case, it is preferable that the organic compound 431_1, the organic compound 431_2, and the guest material 432 (phosphorescent material) be selected such that the emission peak of the exciplex overlaps with an adsorption band, specifically an adsorption band on the longest wavelength side, of a triplet metal to ligand charge transfer (MLCT) transition of the guest material 432 (phosphorescent material). This makes it possible to provide a light-emitting element with drastically improved emission efficiency. Note that in the case where a thermally activated delayed fluorescent material is used instead of the phosphorescent material, it is preferable that the adsorption band on the longest wavelength side be a singlet absorption band.

As the light-emitting material contained in the light-emitting layer 430, any material can be used as long as the material can convert triplet excited energy into light emission. As an example of the material that can convert triplet excited energy into light emission, a thermally activated delayed fluorescent (TADF) material can be given in addition to the phosphorescent material. Therefore, the term "phosphorescent material" in the description can be replaced with the term "thermally activated delayed fluorescent material". Note that the thermally activated delayed fluorescent material is a material that can up-convert a triplet excited state into a singlet excited state (i.e., reverse intersystem crossing is possible) using a little thermal energy and efficiently exhibits light emission (fluorescence) from the singlet excited state. Thermally activated delayed fluorescence is efficiently obtained under the condition where the difference between the triplet excited energy level and the singlet excited energy level is preferably larger than 0 eV and smaller than or equal to 0.2 eV, further preferably larger than 0 eV and smaller than or equal to 0.1 eV.

The material that emits thermally activated delayed fluorescence may be a material that can form a singlet excited state by itself from a triplet excited state by reverse intersystem crossing or may be a combination of two kinds of materials which form an exciplex.

There is no limitation on the emission colors of the light-emitting material included in the light-emitting layer 420 and the light-emitting material included in the light-emitting layer 430, and they may be the same or different. Light emitted from the light-emitting materials is mixed and extracted out of the element; therefore, for example, in the case where their emission colors are complementary colors, the light-emitting element can emit white light. In consideration of the reliability of the light-emitting element, the emission peak wavelength of the light-emitting material included in the light-emitting layer 420 is preferably shorter than that of the light-emitting material included in the light-emitting layer 430.

Structure Example 2 of Light-Emitting Element

Next, a structure example different from the light-emitting element illustrated in FIGS. 6A and 6B is described below with reference to FIGS. 7A and 7B.

Figure 7A:
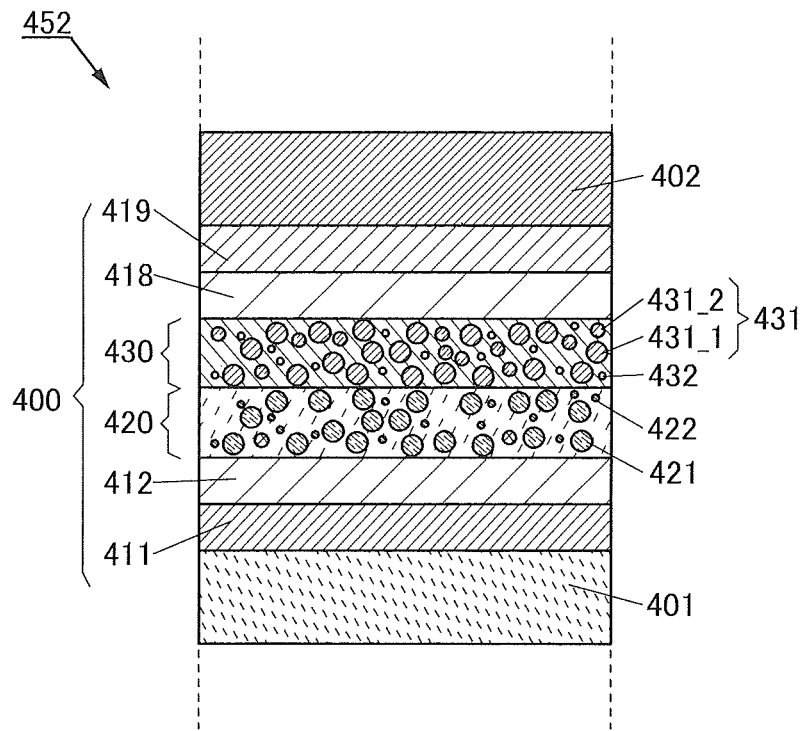
FIGS. 7A and 7B are a schematic cross-sectional view of a light-emitting element according to one embodiment of the present invention and a schematic diagram illustrating the correlation of energy levels.

FIG. 7A is a schematic cross-sectional view of a light-emitting element 452.

In the light-emitting element 452 illustrated in FIG. 7A, an EL layer 400 is provided between a pair of electrodes (an electrode 401 and an electrode 402). Note that in the light-emitting element 452, the electrode 401 functions as an anode, and the electrode 402 functions as a cathode.

The EL layer 400 includes the light-emitting layers 420 and 430. As the EL layer 400 in the light-emitting element 452, the light-emitting layers 420 and 430, the hole-injection layer 411, the hole-transport layer 412, the electron-transport layer 418, and the electron-injection layer 419 are illustrated. However, this stacked-layer structure is an example, and the structure of the EL layer 400 in the light-emitting element 452 is not limited thereto. For example, the stacking order of the above layers of the EL layer 400 may be changed. Alternatively, in the EL layer 400, another functional layer other than the above layers may be provided. The functional layer may have a function of injecting a carrier (an electron or a hole), a function of transporting a carrier, a function of inhibiting a carrier, or a function of generating a carrier, for example.

The light-emitting layer 420 includes the host material 421 and the guest material 422. The light-emitting layer 430 includes the host material 431 and the guest material 432. The host material 431 includes the organic compound 431_1 and the organic compound 431_2. In the following description, the guest material 422 is a fluorescent material and the guest material 432 is a phosphorescent material.

<<Emission Mechanism of Light-Emitting Layer 420>>

The emission mechanism of the light-emitting layer 420 is similar to that of the light-emitting layer 130 in FIG. 1A or the EL layer 135 in FIG. 3.

<<Emission Mechanism of Light-Emitting Layer 430>>

The emission mechanism of the light-emitting layer 430 is similar to that of the light-emitting layer 430 in FIG. 6A.

<Emission Mechanism of Light-Emitting Layers 420 and 430>

Each emission mechanism of the light-emitting layers 420 and 430 is described above. As in the light-emitting element 452, in the case where the light-emitting layers 420 and 430 are in contact with each other, even when energy is transferred from the exciplex to the host material 421 of the light-emitting layer 420 (in particular, when energy of the triplet excited level is transferred) at an interface between the light-emitting layer 420 and the light-emitting layer 430, triplet excited energy can be converted into light emission in the light-emitting layer 420.

The $T_1$ level of the host material 421 of the light-emitting layer 420 is preferably lower than $T_1$ levels of the organic compounds 431_1 and 431_2 in the light-emitting layer 430. In the light-emitting layer 420, the $S_1$ level of the host material 421 is preferably higher than the $S_1$ level of the guest material 422 (fluorescent material) while the $T_1$ level of the host material 421 is preferably lower than the $T_1$ level of the guest material 422 (fluorescent material).

Figure 7B:
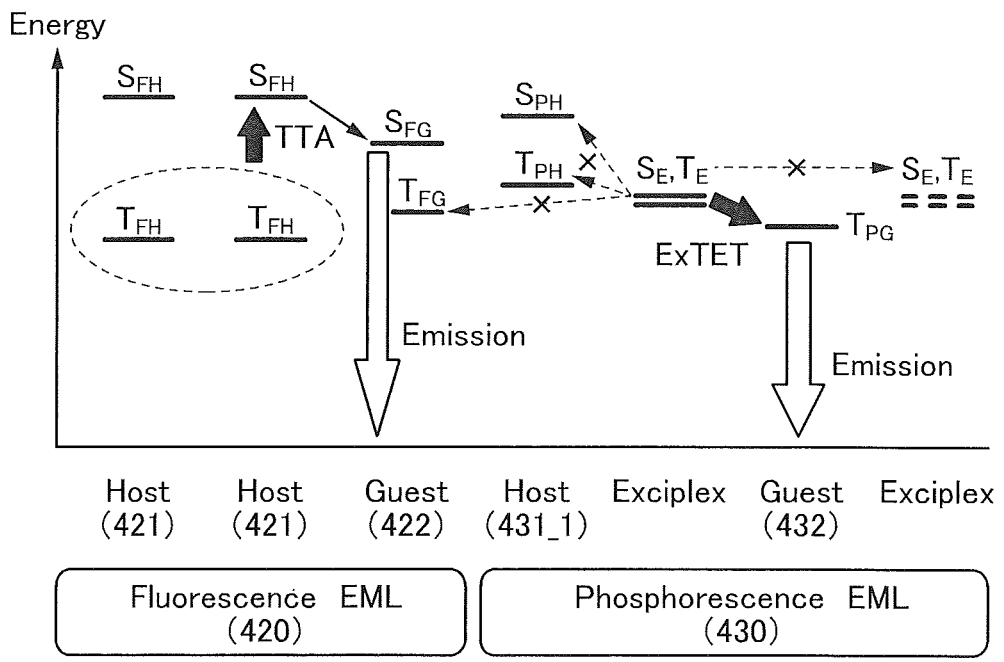

FIG. 7B shows the correlation of energy levels in the case where TTA is utilized in the light-emitting layer 420 and ExTET is utilized in the light-emitting layer 430. What terms and signs in FIG. 7B are listed below.

Fluorescence EML (420): the fluorescent light-emitting layer (light-emitting layer 420)

Phosphorescence EML (430): the phosphorescent light-emitting layer (light-emitting layer 430)

$S_{FH0}$: the level of the lowest singlet excited state of the host material 421

$T_{FH}$: the level of the lowest triplet excited state of the host material 421

$S_{FG}$: the level of the lowest singlet excited state of the guest material 422 (fluorescent material)

$T_{FG}$: the level of the lowest triplet excited state of the guest material 422 (fluorescent material)

$S_{PH}$: the level of the lowest singlet excited state of the host material (organic compound 431_1)

$T_{PH}$: the level of the lowest triplet excited state of the host material (organic compound 431_1)

$T_{PG}$: the level of the lowest triplet excited state of the guest material 432 (phosphorescent material)

$S_E$: the level of the lowest singlet excited state of the exciplex $T_E$: the level of the lowest triplet excited state of the exciplex As shown in FIG. 7B, the exciplex exists only in an excited state; thus, exciton diffusion between the exciplexes is less likely to occur. In addition, because the excited levels ($S_E$ and $T_E$) of the exciplex are lower than the excited levels ($S_{PH}$ and $T_{PH}$) of the organic compound 431_1 (the host material of the phosphorescent material) of the light-emitting layer 430, energy diffusion from the exciplex to the organic compound 431_1 does not occur. Similarly, energy diffusion from the exciplex to the organic compound 431_2 does not occur. That is, emission efficiency of the phosphorescent light-emitting layer (light-emitting layer 430) can be maintained because an exciton diffusion distance of the exciplex is short in the phosphorescent light-emitting layer (light-emitting layer 430). In addition, even when part of the triplet excited energy of the exciplex of the phosphorescent light-emitting layer (light-emitting layer 430) diffuses into the fluorescent light-emitting layer (light-emitting layer 420) through the interface between the fluorescent light-emitting layer (light-emitting layer 420) and the phosphorescent light-emitting layer (light-emitting layer 430), energy loss can be reduced because the triplet excited energy in the fluorescent light-emitting layer (light-emitting layer 420) caused by the diffusion is used for light emission through TTA.

The light-emitting element 452 can have high emission efficiency because ExTET is utilized in the light-emitting layer 430 and TTA is utilized in the light-emitting layer 420 as described above so that energy loss is reduced. As in the light-emitting element 452, in the case where the light-emitting layer 420 and the light-emitting layer 430 are in contact with each other, the number of EL layers 400 as well as the energy loss can be reduced. Therefore, a light-emitting element with low manufacturing cost can be obtained.

Note that the light-emitting layer 420 and the light-emitting layer 430 need not be in contact with each other. In that case, it is possible to prevent energy transfer by the Dexter mechanism (particularly triplet energy transfer) from the organic compound 431_1 or 431_2 in an excited state or the guest material 432 (phosphorescent material) in an excited state which is generated in the light-emitting layer 430 to the host material 421 or the guest material 422 (fluorescent material) in the light-emitting layer 420. Therefore, the thickness of a layer provided between the light-emitting layer 420 and the light-emitting layer 430 may be several nanometers.

The layer provided between the light-emitting layer 420 and the light-emitting layer 430 may contain a single material or both a hole-transport material and an electron-transport material. In the case of a single material, a bipolar material may be used. The bipolar material here refers to a material in which the ratio between the electron mobility and the hole mobility is 100 or less. Alternatively, the hole-transport material, the electron-transport material, or the like may be used. At least one of materials included in the layer may be the same as the host material (organic compound 431_1 or 431_2) of the light-emitting layer 430. This facilitates the manufacture of the light-emitting element and reduces the drive voltage. Furthermore, the hole-transport material and the electron-transport material may form an exciplex, which effectively prevents exciton diffusion. Specifically, it is possible to prevent energy transfer from the host material (organic compound 431_1 or 431_2) in an excited state or the guest material 432 (phosphorescent material) in an excited state of the light-emitting layer 430 to the host material 421 or the guest material 422 (fluorescent material) in the light-emitting layer 420.

Note that in the light-emitting element 452, a carrier recombination region is preferably distributed to some extent. Therefore, it is preferable that the light-emitting layer 420 or 430 have an appropriate degree of carrier-trapping property. It is particularly preferable that the guest material 432 (phosphorescent material) in the light-emitting layer 430 have an electron-trapping property. Alternatively, the guest material 422 (fluorescent material) in the light-emitting layer 420 preferably has a hole-trapping property.

Note that light emitted from the light-emitting layer 420 preferably has a peak on the shorter wavelength side than light emitted from the light-emitting layer 430. Since the luminance of a light-emitting element using a phosphorescent material emitting light with a short wavelength tends to be degraded quickly, fluorescence with a short wavelength is employed so that a light-emitting element with less degradation of luminance can be provided.

Furthermore, the light-emitting layers 420 and 430 are made to emit light with different emission wavelengths, so that the light-emitting element can be a multicolor light-emitting element. In that case, the emission spectrum is formed by combining light having different emission peaks, and thus has at least two peaks.

The above-described structure is suitable for obtaining white light emission. When the light-emitting layers 420 and 430 emit light of complementary colors, white light emission can be obtained.

In addition, white light emission with a high color rendering property that is formed of three primary colors or four or more colors can be obtained by using a plurality of light-emitting materials emitting light with different wavelengths for the light-emitting layer 420. In that case, the light-emitting layer 420 may be divided into layers and each of the divided layers may contain a light-emitting material different from the others.

<Material that can be Used in Light-Emitting Layers>

Next, materials that can be used in the light-emitting layers 420 and 430 are described.

<<Material that can be Used in Light-Emitting Layer 420>>

In the light-emitting layer 420, the host material 421 is present in the highest proportion by weight, and the guest material 422 (fluorescent material) is dispersed in the host material 421. The $S_1$ level of the host material 421 is preferably higher than the $S_1$ level of the guest material 422 (fluorescent material) while the $T_1$ level of the host material 421 is preferably lower than the $T_1$ level of the guest material 422 (fluorescent material).

As the host material 421, a benzo[a]anthracene compound is preferably used to fabricate a light-emitting element with high emission efficiency in which delayed fluorescence accounts for a large proportion of emitted light. Specifically, the compound described in Embodiment 1 or 2 can be used.

<Materials that can be Used in Light-Emitting Layer 430>

In the light-emitting layer 430, the host material (organic compound 431_1 or 431_2) is present in the highest proportion in mass ratio, and the guest material 432 (phosphorescent material) is dispersed in the host materials (organic compounds 431_1 and 431_2). The $T_1$ levels of the host materials (organic compounds 431_1 and 431_2) of the light-emitting layer 430 is preferably higher than the $T_1$ level of the guest material 422 (fluorescent material) of the light-emitting layer 420.

As the host materials (organic compounds 431_1 and 431_2) and the guest material 432 (phosphorescent material), those in the light-emitting element 450 described with reference to FIGS. 6A and 6B can be used Note that the light-emitting layers 420 and 430 can be formed by an evaporation method (including a vacuum evaporation method), an inkjet method, a coating method, gravure printing, or the like.

Note that the structure described in this embodiment can be combined as appropriate with any of the structures described in the other embodiments.

Embodiment 6

In this embodiment is described an example of a mode where a benzo[a]anthracene compound described in Embodiment 2 is used in an active layer of a vertical transistor (static induction transistor: SIT), which is a kind of an organic semiconductor element.

Figure 8:
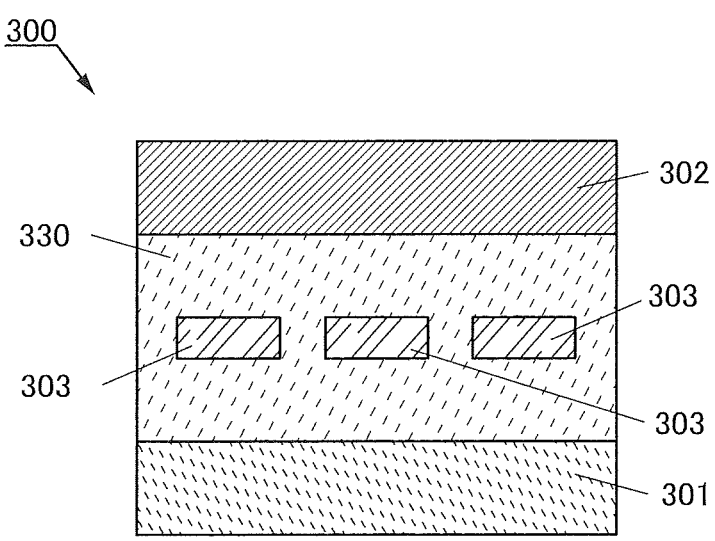
FIG. 8 is a schematic cross-sectional view of a semiconductor element according to one embodiment of the present invention.

The element has a structure in which a thin-film active layer 330 including the benzo[a]anthracene compound described in Embodiment 2 is provided between a source electrode 301 and a drain electrode 302, and gate electrodes 303 are embedded in the active layer 330, as illustrated in FIG. 8. The gate electrode 303 is electrically connected to a means for applying a gate voltage, and the source electrode 301 and the drain electrode 302 are electrically connected to a means for controlling a voltage between the source electrode and the drain electrode.

In such an element structure, when a voltage is applied between the source electrode and the drain electrode without applying a voltage to the gate electrode 303, a current flows (on state). Then, by application of a voltage to the gate electrode 303 in that state, a depletion layer is formed in the periphery of the gate electrode 303, and the current ceases flowing (off state). With such a mechanism, an organic semiconductor element 300 operates as a transistor.

Like a light-emitting element, a vertical transistor should contain a material that can achieve both a high carrier-transport property and high film quality for an active layer; the benzo[a]anthracene compound described in Embodiment 2 meets such a requirement and therefore can be suitably used.

Note that the structure described in this embodiment can be combined as appropriate with any of the structures described in the other embodiments.

Embodiment 7

In this embodiment, a display device including a light-emitting device of one embodiment of the present invention is described with reference to FIGS. 9A and 9B.

Figure 9A:
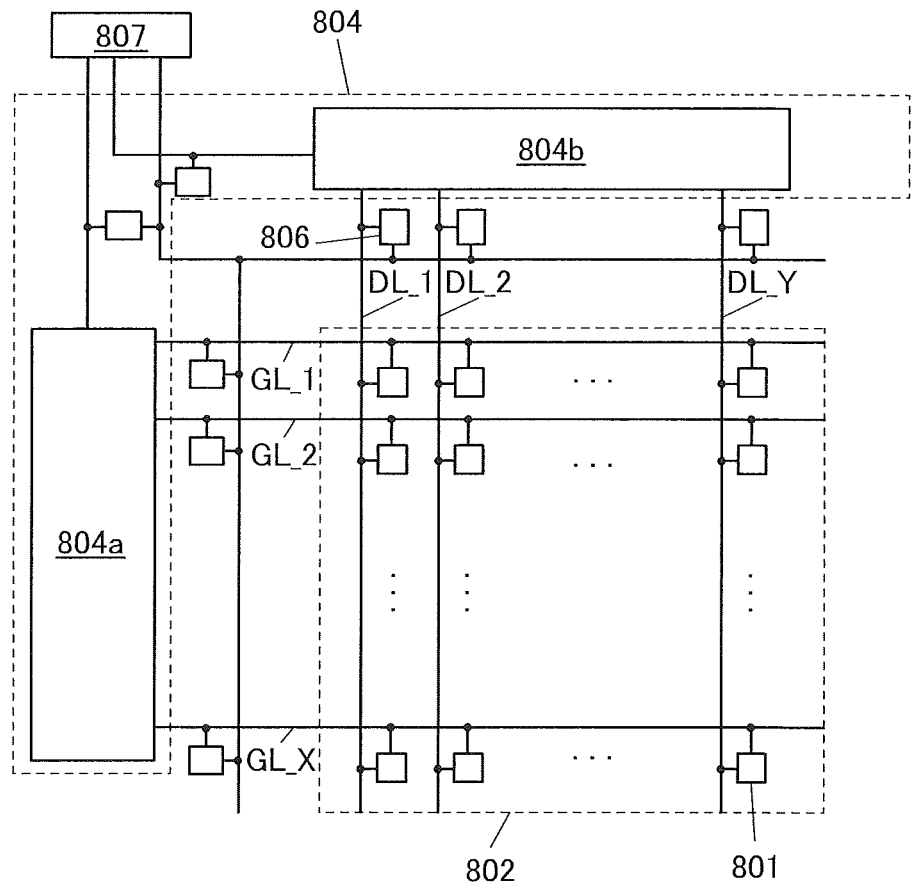
FIGS. 9A and 9B are a block diagram and a circuit diagram showing a display device according to one embodiment of the present invention.
Figure 9B:
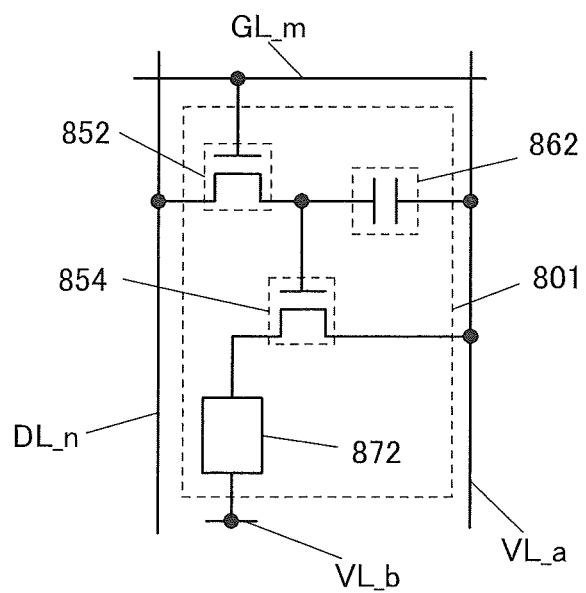

FIG. 9A is a block diagram illustrating the display device of one embodiment of the present invention, and FIG. 9B is a circuit diagram illustrating a pixel circuit of the display device of one embodiment of the present invention.
<Display Device>

The display device illustrated in FIG. 9A includes a region including pixels of display elements (hereinafter the region is referred to as a pixel portion 802), a circuit portion provided outside the pixel portion 802 and including a circuit for driving the pixels (hereinafter the portion is referred to as a driver circuit portion 804), circuits having a function of protecting elements (hereinafter the circuits are referred to as protection circuits 806), and a terminal portion 807. Note that the protection circuits 806 are not necessarily provided.

A part or the whole of the driver circuit portion 804 is preferably formed over a substrate over which the pixel portion 802 is formed. Thus, the number of components and the number of terminals can be reduced. When a part or the whole of the driver circuit portion 804 is not formed over the substrate over which the pixel portion 802 is formed, the part or the whole of the driver circuit portion 804 can be mounted by COG or tape automated bonding (TAB).

The pixel portion 802 includes circuits for driving a plurality of display elements arranged in X rows (X is a natural number of 2 or more) and Y columns (Y is a natural number of 2 or more) (hereinafter, such circuits are referred to as pixel circuits 801). The driver circuit portion 804 includes driver circuits such as a circuit for supplying a signal (scan signal) to select a pixel (hereinafter the circuit is referred to as a scan line driver circuit 804a) and a circuit for supplying a signal (data signal) to drive a display element in a pixel (hereinafter, the circuit is referred to as a signal line driver circuit 804b).

The scan line driver circuit 804a includes a shift register or the like. The scan line driver circuit 804a receives a signal for driving the shift register through the terminal portion 807 and outputs a signal. For example, the scan line driver circuit 804a receives a start pulse signal, a clock signal, or the like and outputs a pulse signal. The scan line driver circuit 804a has a function of controlling the potentials of wirings supplied with scan signals (hereinafter, such wirings are referred to as scan lines GL_1 to GL_X). Note that a plurality of scan line driver circuits 804a may be provided to control the scan lines GL_1 to GL_X separately. Alternatively, the scan line driver circuit 804a has a function of supplying an initialization signal. Not limited thereto, the scan line driver circuit 804a can supply another signal.

The signal line driver circuit 804b includes a shift register or the like. The signal line driver circuit 804b receives a signal (video signal) from which a data signal is derived, as well as a signal for driving the shift register, through the terminal portion 807. The signal line driver circuit 804b has a function of generating a data signal to be written in the pixel circuits 801 based on the video signal. In addition, the signal line driver circuit 804b has a function of controlling output of a data signal in response to a pulse signal produced by input of a start pulse signal, a clock signal, or the like. Furthermore, the signal line driver circuit 804b has a function of controlling the potentials of wirings supplied with data signals (hereinafter, such wirings are referred to as data lines DL_1 to DL_Y). Alternatively, the signal line driver circuit 804b has a function of supplying an initialization signal. Not limited thereto, the signal line driver circuit 804b can supply another signal.

Alternatively, the signal line driver circuit 804b is formed using a plurality of analog switches or the like, for example. The signal line driver circuit 804b can output, as the data signals, signals obtained by time-dividing the video signal by sequentially turning on the plurality of analog switches. The signal line driver circuit 804b may include a shift register or the like.

A pulse signal and a data signal are input, through one of the plurality of scan lines GL supplied with scan signals and one of the plurality of data lines DL supplied with data signals, respectively, to each of the plurality of the pixel circuits 801. Writing and holding of the data signal in each of the plurality of pixel circuits 801 are controlled by the scan line driver circuit 804a. For example, to the pixel circuit 801 in the m-th row and the n-th column an is a natural number of less than or equal to X, and n is a natural number of less than or equal to 1% a pulse signal is input from the scan line driver circuit 804a through the scan line GL_m, and a data signal is input from the signal line driver circuit 804b through the data line DL_n in accordance with the potential of the scan line GL_m.

The protection circuit 806 shown in FIG. 9A is connected to, for example, the scan line GL between the scan line driver circuit 804a and the pixel circuits 801. Alternatively, the protection circuit 806 is connected to the data line DL between the signal line driver circuit 804b and the pixel circuit 801. Alternatively, the protection circuit 806 can be connected to a wiring between the scan line driver circuit 804a and the terminal portion 807. Alternatively, the protection circuit 806 can be electrically connected to a wiring between the signal line driver circuit 804b and the terminal portion 807. Note that the terminal portion 807 means a portion having terminals for inputting power, control signals, and video signals to the display device from external circuits.

The protection circuit 806 is a circuit which electrically conducts a wiring connected to the protection circuit to another wiring when a potential out of a certain range is supplied to the wiring connected to the protection circuit.

As illustrated in FIG. 9A, the protection circuits 806 are provided for the pixel portion 802 and the driver circuit portion 804, so that the resistance of the display device to overcurrent generated by electrostatic discharge (ESD) or the like can be improved. Note that the configuration of the protection circuits 806 is not limited to that, and for example, the protection circuit 806 may be configured to be connected to the scan line driver circuit 804a or the protection circuit 806 may be configured to be connected to the signal line driver circuit 804*b*. Alternatively, the protection circuit 806 may be configured to be connected to the terminal portion 807.

In FIG. 9A, an example in which the driver circuit portion 804 includes the scan line driver circuit 804*a* and the signal line driver circuit 804*b* is shown; however, the structure is not limited thereto. For example, only the scan line driver circuit 804*a* may be formed and a separately prepared substrate where a signal line driver circuit is formed (e.g., a driver circuit substrate formed with a single crystal semiconductor film or a polycrystalline semiconductor film) may be mounted.

Structure Example of Pixel Circuit

Each of the plurality of pixel circuits 801 in FIG. 9A can have the structure illustrated in FIG. 9B, for example.

The pixel circuit 801 shown in FIG. 9B includes transistors 852 and 854, a capacitor 862, and a light-emitting element 872.

One of a source electrode and a drain electrode of the transistor 852 is electrically connected to a wiring to which a data signal is supplied (a data line DL_n). A gate electrode of the transistor 852 is electrically connected to a wiring to which a gate signal is supplied (a scan line GL_m).

The transistor 852 has a function of controlling whether to write a data signal.

One of a pair of electrodes of the capacitor 862 is electrically connected to a wiring to which a potential is supplied (hereinafter referred to as a potential supply line VL_a), and the other is electrically connected to the other of the source electrode and the drain electrode of the transistor 852.

The capacitor 862 functions as a storage capacitor for storing written data.

One of a source electrode and a drain electrode of the transistor 854 is electrically connected to the potential supply line VL_a. Furthermore, a gate electrode of the transistor 854 is electrically connected to the other of the source electrode and the drain electrode of the transistor 852.

One of an anode and a cathode of the light-emitting element 872 is electrically connected to a potential supply line VL_b, and the other is electrically connected to the other of the source electrode and the drain electrode of the transistor 854.

As the light-emitting element 872, any of the light-emitting elements described in Embodiments 1 to 5 can be used.

A high power supply potential VDD is supplied to one of the potential supply line VL_a and the potential supply line VL_b, and a low power supply potential VSS is supplied to the other.

For example, in the display device including the pixel circuit 801 in FIG. 9B, the pixel circuits 801 are sequentially selected row by row by the scan line driver circuit 804*a* illustrated in FIG. 9A, whereby the transistor 852 is turned on and a data signal is written.

When the transistor 852 is turned off, the pixel circuits 801 in which the data has been written are brought into a holding state. Furthermore, the amount of current flowing between the source electrode and the drain electrode of the transistor 854 is controlled in accordance with the potential of the written data signal. The light-emitting element 872 emits light with a luminance corresponding to the amount of flowing current. This operation is sequentially performed row by row; thus, an image is displayed.

A light-emitting element of one embodiment of the present invention can be used for an active matrix method in which an active element is included in a pixel of a display device or a passive matrix method in which an active element is not included in a pixel of a display device.

In the active matrix method, as an active element (a non-linear element), not only a transistor but also various active elements (non-linear elements) can be used. For example, a metal insulator metal (MIM) or a thin film diode (TFD) can also be used. Since these elements can be formed with a smaller number of manufacturing steps, manufacturing costs can be reduced or yield can be improved. Alternatively, since the size of the element is small, the aperture ratio can be improved, leading to lower power consumption or higher luminance.

As a method other than the active matrix method, the passive matrix method in which an active element (a non-linear element) is not used can also be used. Since an active element (a non-linear element) is not used, the number of manufacturing steps is small, so that manufacturing costs can be reduced or yield can be improved. Alternatively, since an active element (a non-linear element) is not used, the aperture ratio can be improved, leading to lower power consumption, higher luminance, or the like.

The structure described in this embodiment can be used in appropriate combination with the structure described in any of the other embodiments.

Embodiment 8

In this embodiment, a display device including a light-emitting element of one embodiment of the present invention and an electronic device in which the display device is provided with an input device are described with reference to FIGS. 10A and 10B, FIGS. 11A to 11C, FIGS. 12A and 12B, FIGS. 13A and 13B, and FIG. 14.

<Description 1 of Touch Panel>

In this embodiment, a touch panel 2000 including a display device and an input device is described as an example of an electronic device. In addition, an example in which a touch sensor is used as an input device is described.

Figure 10A:
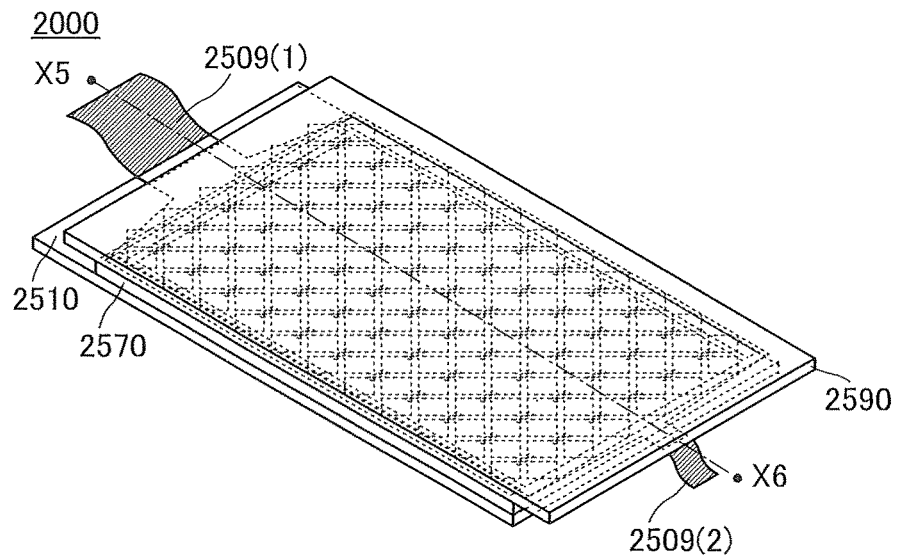
FIGS. 10A and 10B are perspective views of an example of a touch panel according to one embodiment of the present invention.
Figure 10B:
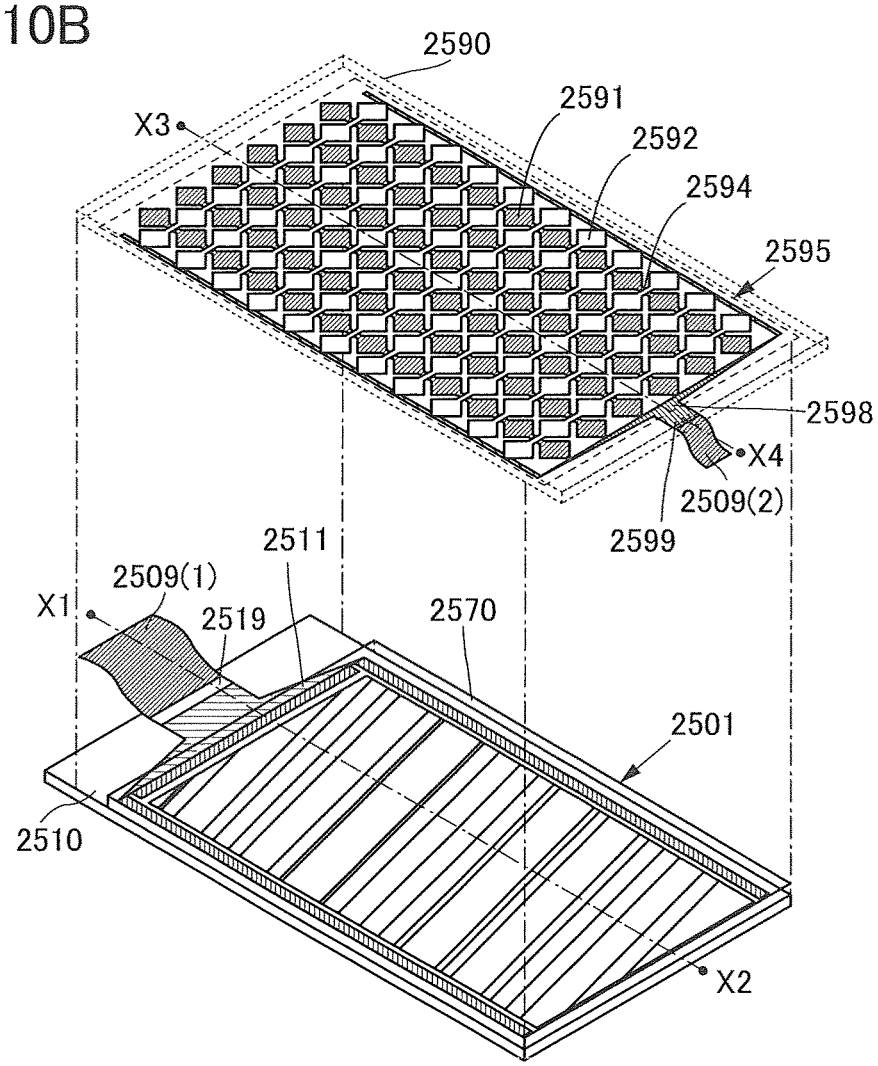

FIGS. 10A and 10B are perspective views of the touch panel 2000. Note that FIGS. 10A and 10B illustrate only main components of the touch panel 2000 for simplicity.

The touch panel 2000 includes a display device 2501 and a touch sensor 2595 (see FIG. 10B). The touch panel 2000 also includes a substrate 2510, a substrate 2570, and a substrate 2590. The substrate 2510, the substrate 2570, and the substrate 2590 each have flexibility. Note that one or all of the substrates 2510, 2570, and 2590 may be inflexible.

The display device 2501 includes a plurality of pixels over the substrate 2510 and a plurality of wirings 2511 through which signals are supplied to the pixels. The plurality of wirings 2511 are led to a peripheral portion of the substrate 2510, and parts of the plurality of wirings 2511 form a terminal 2519. The terminal 2519 is electrically connected to an FPC 2509(1).

The substrate 2590 includes the touch sensor 2595 and a plurality of wirings 2598 electrically connected to the touch sensor 2595. The plurality of wirings 2598 are led to a peripheral portion of the substrate 2590, and parts of the plurality of wirings 2598 form a terminal. The terminal is electrically connected to an FPC 2509(2). Note that in FIG. 10B, electrodes, wirings, and the like of the touch sensor 2595 provided on the back side of the substrate 2590 (the side facing the substrate 2510) are indicated by solid lines for clarity.

As the touch sensor 2595, a capacitive touch sensor can be used. Examples of the capacitive touch sensor are a surface capacitive touch sensor and a projected capacitive touch sensor.

Examples of the projected capacitive touch sensor are a self-capacitive touch sensor and a mutual capacitive touch sensor, which differ mainly in the driving method. The use of a mutual capacitive type is preferable because multiple points can be sensed simultaneously.

Note that the touch sensor 2595 illustrated in FIG. 10B is an example of using a projected capacitive touch sensor.

Note that a variety of sensors that can sense proximity or touch of a sensing target such as a finger can be used as the touch sensor 2595.

The projected capacitive touch sensor 2595 includes electrodes 2591 and electrodes 2592. The electrodes 2591 are electrically connected to any of the plurality of wirings 2598, and the electrodes 2592 are electrically connected to any of the other wirings 2598.

The electrodes 2592 each have a shape of a plurality of quadrangles arranged in one direction with one corner of a quadrangle connected to one corner of another quadrangle as illustrated in FIGS. 10A and 10B.

The electrodes 2591 each have a quadrangular shape and are arranged in a direction intersecting with the direction in which the electrodes 2592 extend.

A wiring 2594 electrically connects two electrodes 2591 between which the electrode 2592 is positioned. The intersecting area of the electrode 2592 and the wiring 2594 is preferably as small as possible. Such a structure allows a reduction in the area of a region where the electrodes are not provided, reducing variation in transmittance. As a result, variation in luminance of light passing through the touch sensor 2595 can be reduced.

Note that the shapes of the electrodes 2591 and the electrodes 2592 are not limited thereto and can be any of a variety of shapes. For example, a structure may be employed in which the plurality of electrodes 2591 are arranged so that gaps between the electrodes 2591 are reduced as much as possible, and the electrodes 2592 are spaced apart from the electrodes 2591 with an insulating layer interposed therebetween to have regions not overlapping with the electrodes 2591. In this case, it is preferable to provide, between two adjacent electrodes 2592, a dummy electrode electrically insulated from these electrodes because the area of regions having different transmittances can be reduced.

<Display Panel>

Figure 11A:
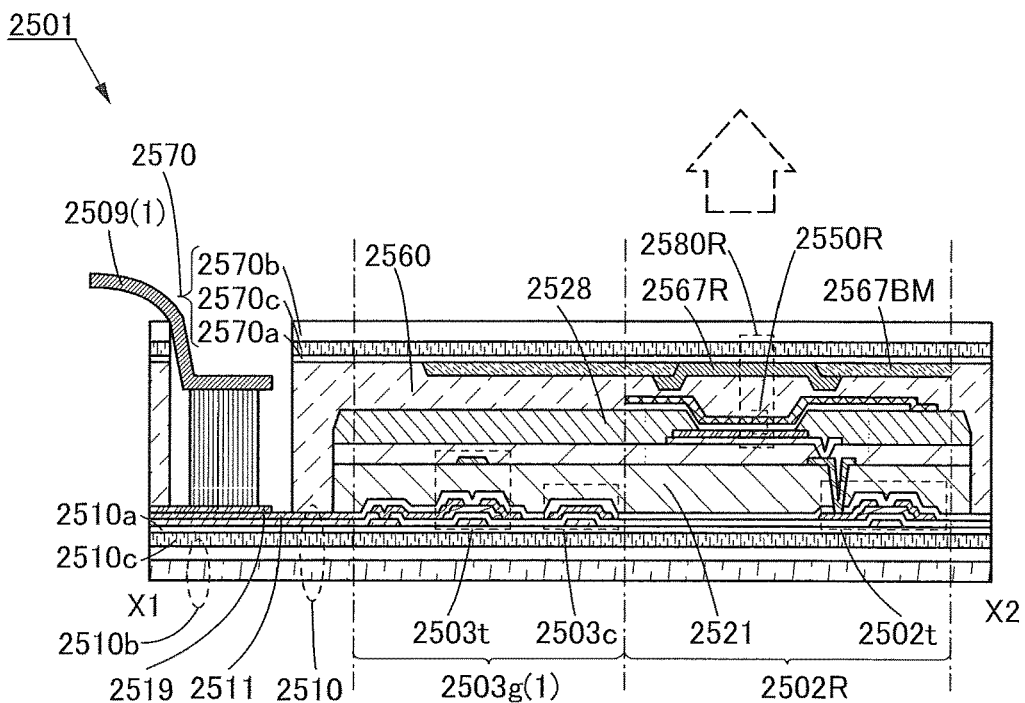
FIGS. 11A to 11C are cross-sectional views of examples of the display device and the touch sensor according to one embodiment of the present invention.

Next, the display device 2501 is described in detail with reference to FIG. 11A. FIG. 11A corresponds to a cross-sectional view taken along dashed-dotted line X1-X2 in FIG. 10B.

The display device 2501 includes a plurality of pixels arranged in a matrix. Each of the pixels includes a display element and a pixel circuit for driving the display element.

In the following description, an example of using a light-emitting element that emits white light as a display element will be described; however, the display element is not limited to such an element. For example, light-emitting elements that emit light of different colors may be included so that the light of different colors can be emitted from adjacent pixels.

For the substrate 2510 and the substrate 2570, for example, a flexible material with a vapor permeability lower than or equal to $1\times10^{-5}$ g·m$^{-2}$·day$^{-1}$, preferably lower than or equal to $1\times10^{-6}$ g·m$^{-2}$·day$^{-1}$ can be favorably used. Alternatively, materials whose thermal expansion coefficients are substantially equal to each other are preferably used for the substrate 2510 and the substrate 2570. For example, the coefficients of linear expansion of the materials are preferably lower than or equal to $1\times10^{-3}$/K, further preferably lower than or equal to $5\times10^{-5}$/K, and still further preferably lower than or equal to $1\times10^{-5}$/K.

Note that the substrate 2510 is a stacked body including an insulating layer 2510a for preventing impurity diffusion into the light-emitting element, a flexible substrate 2510b, and an adhesive layer 2510c for attaching the insulating layer 2510a and the flexible substrate 2510b to each other. The substrate 2570 is a stacked body including an insulating layer 2570a for preventing impurity diffusion into the light-emitting element, a flexible substrate 2570b, and an adhesive layer 2570c for attaching the insulating layer 2570a and the flexible substrate 2570b to each other.

For the adhesive layer 2510c and the adhesive layer 2570c, for example, polyester, polyolefin, polyamide (e.g., nylon, aramid), polyimide, polycarbonate, or an acrylic resin, polyurethane, or an epoxy resin, or a material which includes a resin having a siloxane bond such as silicone can be used.

A sealing layer 2560 is provided between the substrate 2510 and the substrate 2570. The sealing layer 2560 preferably has a refractive index higher than that of air. In the case where light is extracted to the sealing layer 2560 side as illustrated in FIG. 11A, the sealing layer 2560 can also serve as an optical adhesive layer.

A sealant may be formed in the peripheral portion of the sealing layer 2560. With the use of the sealant, a light-emitting element 2550R can be provided in a region surrounded by the substrate 2510, the substrate 2570, the sealing layer 2560, and the sealant. Note that an inert gas (such as nitrogen or argon) may be used instead of the sealing layer 2560. A drying agent may be provided in the inert gas so as to adsorb moisture or the like. An ultraviolet curable resin or a heat curable resin may be used; for example, a polyvinyl chloride (PVC) based resin, an acrylic resin, a polyimide-based resin, an epoxy-based resin, a silicone-based resin, a polyvinyl butyral (PVB) based resin, or an ethylene vinyl acetate (EVA) based resin can be used. For example, an epoxy-based resin or a glass frit is preferably used as the sealant. As a material used for the sealant, a material which is impermeable to moisture or oxygen is preferably used.

The display device 2501 includes a pixel 2502R. The pixel 2502R includes a light-emitting module 2580R.

The pixel 2502R includes the light-emitting element 2550R and a transistor 2502t that can supply electric power to the light-emitting element 2550R. Note that the transistor 2502t functions as part of the pixel circuit. The light-emitting module 2580R includes the light-emitting element 2550R and a coloring layer 2567R.

The light-emitting element 2550R includes a lower electrode, an upper electrode, and an EL layer between the lower electrode and the upper electrode. As the light-emitting element 2550R, any of the light-emitting elements described in Embodiments 1 to 5 can be used, for example.

A microcavity structure may be employed between the lower electrode and the upper electrode so as to increase the intensity of light having a specific wavelength.

In the case where the sealing layer 2560 is provided on the light extraction side, the sealing layer 2560 is in contact with the light-emitting element 2550R and the coloring layer 2567R.

The coloring layer 2567R is positioned in a region overlapping with the light-emitting element 2550R. Accordingly, part of light emitted from the light-emitting element 2550R passes through the coloring layer 2567R and is emitted to the outside of the light-emitting module 2580R as indicated by an arrow in the figure.

The display device 2501 includes a light-blocking layer 2567BM on the light extraction side. The light-blocking layer 2567BM is provided so as to surround the coloring layer 2567R.

The coloring layer 2567R is a coloring layer having a function of transmitting light in a particular wavelength region. For example, a color filter for transmitting light in a red wavelength range, a color filter for transmitting light in a green wavelength range, a color filter for transmitting light in a blue wavelength range, a color filter for transmitting light in a yellow wavelength range, or the like can be used. Each color filter can be formed with any of various materials by a printing method, an inkjet method, an etching method using a photolithography technique, or the like.

An insulating layer 2521 is provided in the display device 2501. The insulating layer 2521 covers the transistor 2502t. Note that the insulating layer 2521 has a function of covering unevenness caused by the pixel circuit. The insulating layer 2521 may have a function of suppressing impurity diffusion. This can prevent the reliability of the transistor 2502t or the like from being lowered by impurity diffusion.

The light-emitting element 2550R is formed over the insulating layer 2521. A partition 2528 is provided so as to overlap with an end portion of the lower electrode of the light-emitting element 2550R. Note that a spacer for controlling the distance between the substrate 2510 and the substrate 2570 may be formed over the partition 2528.

A scan line driver circuit 2503g(1) includes a transistor 2503t and a capacitor 2503c. Note that the driver circuit can be formed in the same process and over the same substrate as those of the pixel circuits.

The wirings 2511 through which signals can be supplied are provided over the substrate 2510. The terminal 2519 is provided over the wirings 2511. The FPC 2509(1) is electrically connected to the terminal 2519. The FPC 2509(1) has a function of supplying a video signal, a clock signal, a start signal, a reset signal, or the like. Note that the FPC 2509(1) may be provided with a printed wiring board (PWB).

Figure 11B:
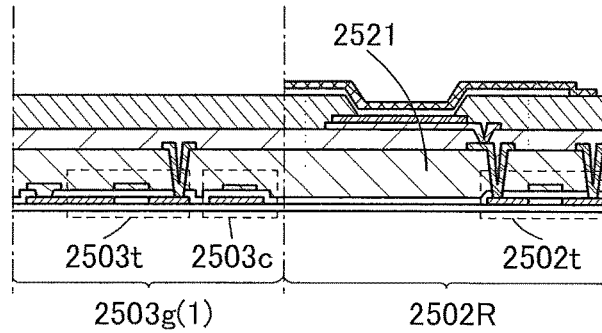

In the display device 2501, transistors with any of a variety of structures can be used. FIG. 11A illustrates an example of using bottom-gate transistors; however, the present invention is not limited to this example, and top-gate transistors may be used in the display device 2501 as illustrated in FIG. 11B.

In addition, there is no particular limitation on the polarity of the transistor 2502t and the transistor 2503t. For these transistors, n-channel and p-channel transistors may be used, or either n-channel transistors or p-channel transistors may be used, for example. Furthermore, there is no particular limitation on the crystallinity of a semiconductor film used for the transistors 2502t and 2503t. For example, an amorphous semiconductor film or a crystalline semiconductor film may be used. Examples of semiconductor materials include Group 13 semiconductors (e.g., a semiconductor including gallium), Group 14 semiconductors (e.g., a semiconductor including silicon), compound semiconductors (including oxide semiconductors), organic semiconductors, and the like. An oxide semiconductor that has an energy gap of 2 eV or more, preferably 2.5 eV or more, further preferably 3 eV or more is preferably used for one of the transistors 2502t and 2503t or both, so that the off-state current of the transistors can be reduced. Examples of the oxide semiconductors include an In—Ga oxide, an In-M-Zn oxide (M represents aluminum (Al), gallium (Ga), yttrium (Y), zirconium (Zr), lanthanum (La), cerium (Ce), tin (Sn), hafnium (Hf), or neodymium (Nd)), and the like.

<Touch Sensor>

Figure 11C:
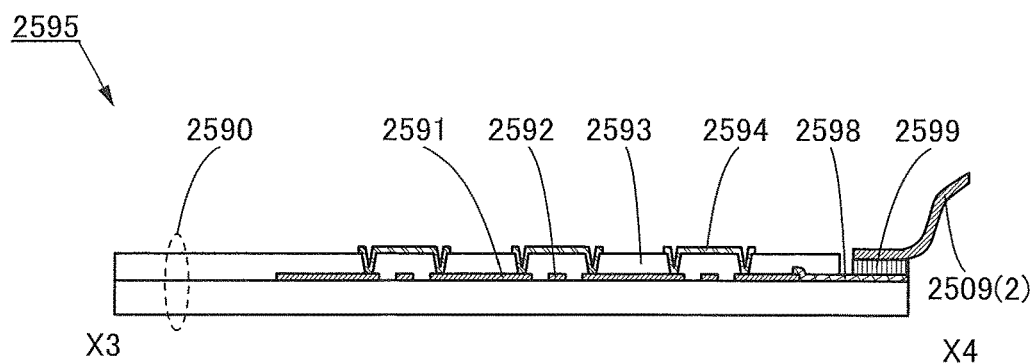

Next, the touch sensor 2595 is described in detail with reference to FIG. 11C. FIG. 11C corresponds to a cross-sectional view taken along dashed-dotted line X3-X4 in FIG. 10B.

The touch sensor 2595 includes the electrodes 2591 and 2592 provided in a staggered arrangement on the substrate 2590, an insulating layer 2593 covering the electrodes 2591 and 2592, and the wiring 2594 that electrically connects the adjacent electrodes 2591 to each other.

The electrodes 2591 and 2592 are formed using a light-transmitting conductive material. As a light-transmitting conductive material, a conductive oxide such as indium oxide, indium tin oxide, indium zinc oxide, zinc oxide, or zinc oxide to which gallium is added can be used. Note that a film including graphene may be used as well. The film including graphene can be formed, for example, by reducing a film including graphene oxide. As a reducing method, a method with application of heat or the like can be employed.

The electrodes 2591 and 2592 may be formed by, for example, depositing a light-transmitting conductive material on the substrate 2590 by a sputtering method and then removing an unnecessary portion by any of various pattern forming techniques such as photolithography.

Examples of a material for the insulating layer 2593 are a resin such as an acrylic resin or an epoxy resin, a resin having a siloxane bond, and an inorganic insulating material such as silicon oxide, silicon oxynitride, or aluminum oxide.

Openings reaching the electrodes 2591 are formed in the insulating layer 2593, and the wiring 2594 electrically connects the adjacent electrodes 2591. A light-transmitting conductive material can be favorably used as the wiring 2594 because the aperture ratio of the touch panel can be increased. Moreover, a material with higher conductivity than the conductivities of the electrodes 2591 and 2592 can be favorably used for the wiring 2594 because electric resistance can be reduced.

One electrode 2592 extends in one direction, and a plurality of electrodes 2592 are provided in the form of stripes. The wiring 2594 intersects with the electrode 2592.

Adjacent electrodes 2591 are provided with one electrode 2592 provided therebetween. The wiring 2594 electrically connects the adjacent electrodes 2591.

Note that the plurality of electrodes 2591 are not necessarily arranged in the direction orthogonal to one electrode 2592 and may be arranged to intersect with one electrode 2592 at an angle greater than 0 degrees and less than 90 degrees.

The wiring 2598 is electrically connected to any of the electrodes 2591 and 2592. Part of the wiring 2598 functions as a terminal. For the wiring 2598, a metal material such as aluminum, gold, platinum, silver, nickel, titanium, tungsten, chromium, molybdenum, iron, cobalt, copper, or palladium or an alloy material containing any of these metal materials can be used.

Note that an insulating layer that covers the insulating layer 2593 and the wiring 2594 may be provided to protect the touch sensor 2595.

A connection layer 2599 electrically connects the wiring 2598 to the FPC 2509(2).

As the connection layer 2599, any of various anisotropic conductive films (ACF), anisotropic conductive pastes (ACP), or the like can be used.

<Description 2 of Touch Panel>

Figure 12A:
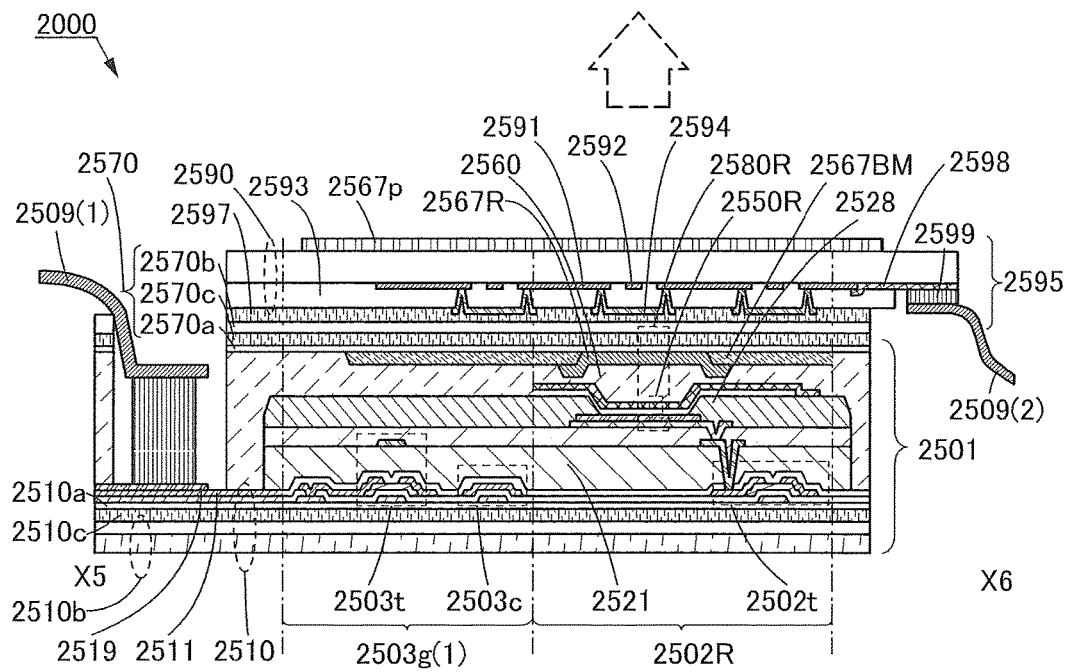
FIGS. 12A and 12B are cross-sectional views of examples of a touch panel according to one embodiment of the present invention.

Next, the touch panel 2000 is described in detail with reference to FIG. 12A. FIG. 12A corresponds to a cross-sectional view taken along dashed-dotted line X5-X6 in FIG. 10A.

In the touch panel 2000 illustrated in FIG. 12A, the display device 2501 described with reference to FIG. 11A and the touch sensor 2595 described with reference to FIG. 11C are attached to each other.

The touch panel 2000 illustrated in FIG. 12A includes an adhesive layer 2597 and an anti-reflective layer 2567p in addition to the components described with reference to FIGS. 11A and 11C.

The adhesive layer 2597 is provided in contact with the wiring 2594. Note that the adhesive layer 2597 attaches the substrate 2590 to the substrate 2570 so that the touch sensor 2595 overlaps with the display device 2501. The adhesive layer 2597 preferably has a light-transmitting property. A heat curable resin or an ultraviolet curable resin can be used for the adhesive layer 2597. For example, an acrylic resin, an urethane-based resin, an epoxy-based resin, or a siloxane-based resin can be used.

The anti-reflective layer 2567p is positioned in a region overlapping with pixels. As the anti-reflective layer 2567p, a circularly polarizing plate can be used, for example.

Next, a touch panel having a structure different from that illustrated in FIG. 12A is described with reference to FIG. 12B.

Figure 12B:
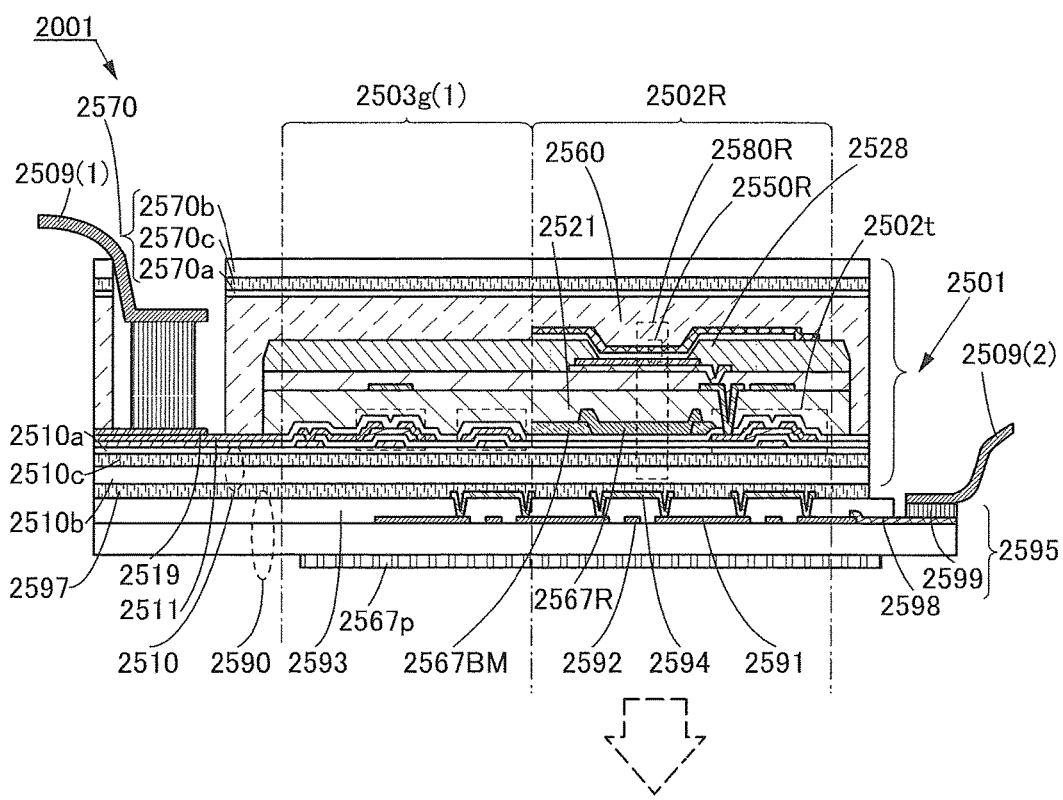

FIG. 12B is a cross-sectional view of a touch panel 2001. The touch panel 2001 illustrated in FIG. 12B differs from the touch panel 2000 illustrated in FIG. 12A in the position of the touch sensor 2595 relative to the display device 2501. Different parts are described in detail below, and the above description of the touch panel 2000 is referred to for the other similar parts.

The coloring layer 2567R is positioned in a region overlapping with the light-emitting element 2550R. The light-emitting element 2550R illustrated in FIG. 12B emits light to the side where the transistor 2502t is provided. Accordingly, part of light emitted from the light-emitting element 2550R passes through the coloring layer 2567R and is emitted to the outside of the light-emitting module 2580R as indicated by the arrow in the figure.

The touch sensor 2595 is provided on the substrate 2510 side of the display device 2501.

The adhesive layer 2597 is provided between the substrate 2510 and the substrate 2590 and attaches the touch sensor 2595 to the display device 2501.

As illustrated in FIG. 12A or 12B, light may be emitted from the light-emitting element to one of upper and lower sides, or both, of the substrate.

<Method of Driving Touch Panel>

Next, an example of a method of driving a touch panel is described with reference to FIGS. 13A and 13B.

Figure 13A:
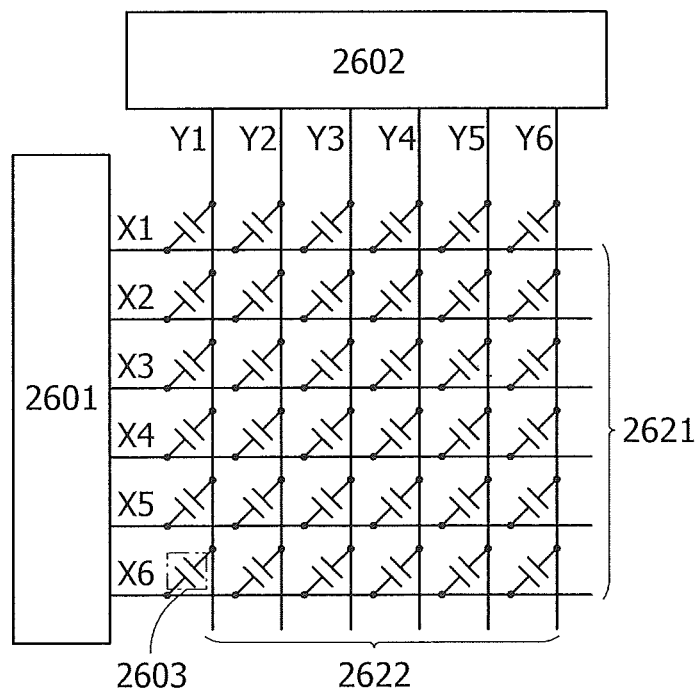
FIGS. 13A and 13B are a block diagram and a timing chart of a touch sensor according to one embodiment of the present invention.

FIG. 13A is a block diagram illustrating the structure of a mutual capacitive touch sensor. FIG. 13A illustrates a pulse voltage output circuit 2601 and a current sensing circuit 2602. Note that in FIG. 13A, six wirings X1 to X6 represent the electrodes 2621 to which a pulse voltage is applied, and six wirings Y1 to Y6 represent the electrodes 2622 that detect changes in current. FIG. 13A also illustrates capacitors 2603 that are each formed in a region in which the electrodes 2621 and 2622 overlap with each other. Note that functional replacement between the electrodes 2621 and the electrodes 2622 is possible.

The pulse voltage output circuit 2601 is a circuit for sequentially applying a pulse voltage to the wirings X1 to X6. By application of a pulse voltage to the wirings X1 to X6, an electric field is generated between the electrodes 2621 and the electrodes 2622 of the capacitor 2603. When the electric field between the electrodes is shielded, for example, a change occurs in the capacitor 2603 (mutual capacitance). The approach or contact of a sensing target can be sensed by utilizing this change.

The current sensing circuit 2602 is a circuit for detecting changes in current flowing through the wirings Y1 to Y6 that are caused by the change in mutual capacitance in the capacitor 2603. No change in current value is detected in the wirings Y1 to Y6 when there is no approach or contact of a sensing target, whereas a decrease in current value is detected when mutual capacitance is decreased owing to the approach or contact of a sensing target. Note that an integrator circuit or the like is used for sensing of current values.

Figure 13B:
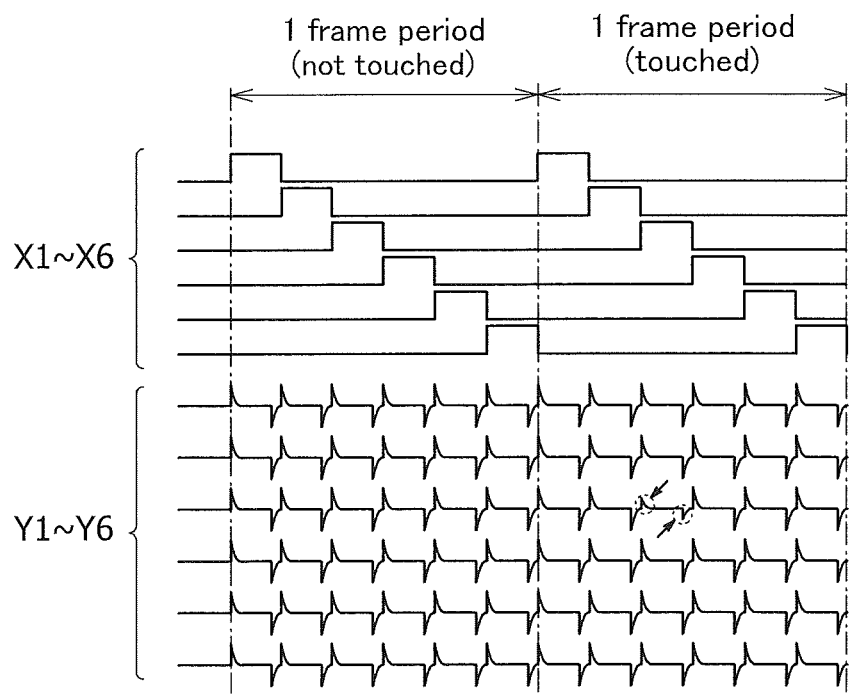

FIG. 13B is a timing chart showing input and output waveforms in the mutual capacitive touch sensor illustrated in FIG. 13A. In FIG. 13B, sensing of a sensing target is performed in all the rows and columns in one frame period. FIG. 13B shows a period when a sensing target is not sensed (not touched) and a period when a sensing target is sensed (touched). Sensed current values of the wirings Y1 to Y6 are shown as the waveforms of voltage values.

A pulse voltage is sequentially applied to the wirings X1 to X6, and the waveforms of the wirings Y1 to Y6 change in accordance with the pulse voltage. When there is no approach or contact of a sensing target, the waveforms of the wirings Y1 to Y6 change in accordance with changes in the voltages of the wirings X1 to X6. The current value is decreased at the point of approach or contact of a sensing target and accordingly the waveform of the voltage value changes.

By detecting a change in mutual capacitance in this manner, the approach or contact of a sensing target can be sensed.

<Sensor Circuit>

Figure 14:
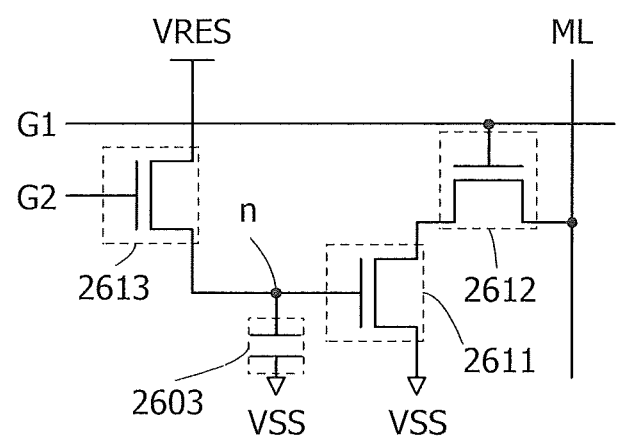
FIG. 14 is a circuit diagram of a touch sensor according to one embodiment of the present invention.

Although FIG. 13A illustrates a passive matrix touch sensor in which only the capacitor 2603 is provided at the intersection of wirings as a touch sensor, an active matrix touch sensor including a transistor and a capacitor may be used. FIG. 14 illustrates an example of a sensor circuit included in an active matrix touch sensor.

The sensor circuit in FIG. 14 includes the capacitor 2603 and a transistor 2611, a transistor 2612, and a transistor 2613.

A signal G2 is input to a gate of the transistor 2613. A voltage VRES is applied to one of a source and a drain of the transistor 2613, and one electrode of the capacitor 2603 and a gate of the transistor 2611 are electrically connected to the other of the source and the drain of the transistor 2613. One of a source and a drain of the transistor 2611 is electrically connected to one of a source and a drain of the transistor 2612, and a voltage VSS is applied to the other of the source and the drain of the transistor 2611. A signal G1 is input to a gate of the transistor 2612, and a wiring ML is electrically connected to the other of the source and the drain of the transistor 2612. The voltage VSS is applied to the other electrode of the capacitor 2603.

Next, the operation of the sensor circuit in FIG. 14 is described. First, a potential for turning on the transistor 2613 is supplied as the signal G2, and a potential with respect to the voltage VRES is thus applied to the node n connected to the gate of the transistor 2611. Then, a potential for turning off the transistor 2613 is applied as the signal G2, whereby the potential of the node n is maintained.

Then, mutual capacitance of the capacitor 2603 changes owing to the approach or contact of a sensing target such as a finger, and accordingly the potential of the node n is changed from VRES.

In reading operation, a potential for turning on the transistor 2612 is supplied as the signal G1. A current flowing through the transistor 2611, that is, a current flowing through the wiring ML is changed in accordance with the potential of the node n. By sensing this current, the approach or contact of a sensing target can be sensed.

In each of the transistors 2611, 2612, and 2613, an oxide semiconductor layer is preferably used as a semiconductor layer in which a channel region is formed. In particular, such a transistor is preferably used as the transistor 2613 so that the potential of the node n can be held for a long time and the frequency of operation of resupplying VRES to the node n (refresh operation) can be reduced.

Note that the structure described in this embodiment can be combined as appropriate with any of the structures described in the other embodiments.

Embodiment 9

In this embodiment, a display module and electronic devices including a light-emitting element of one embodiment of the present invention are described with reference to FIG. 15 and FIGS. 16A to 16G.

<Display Module>

Figure 15:
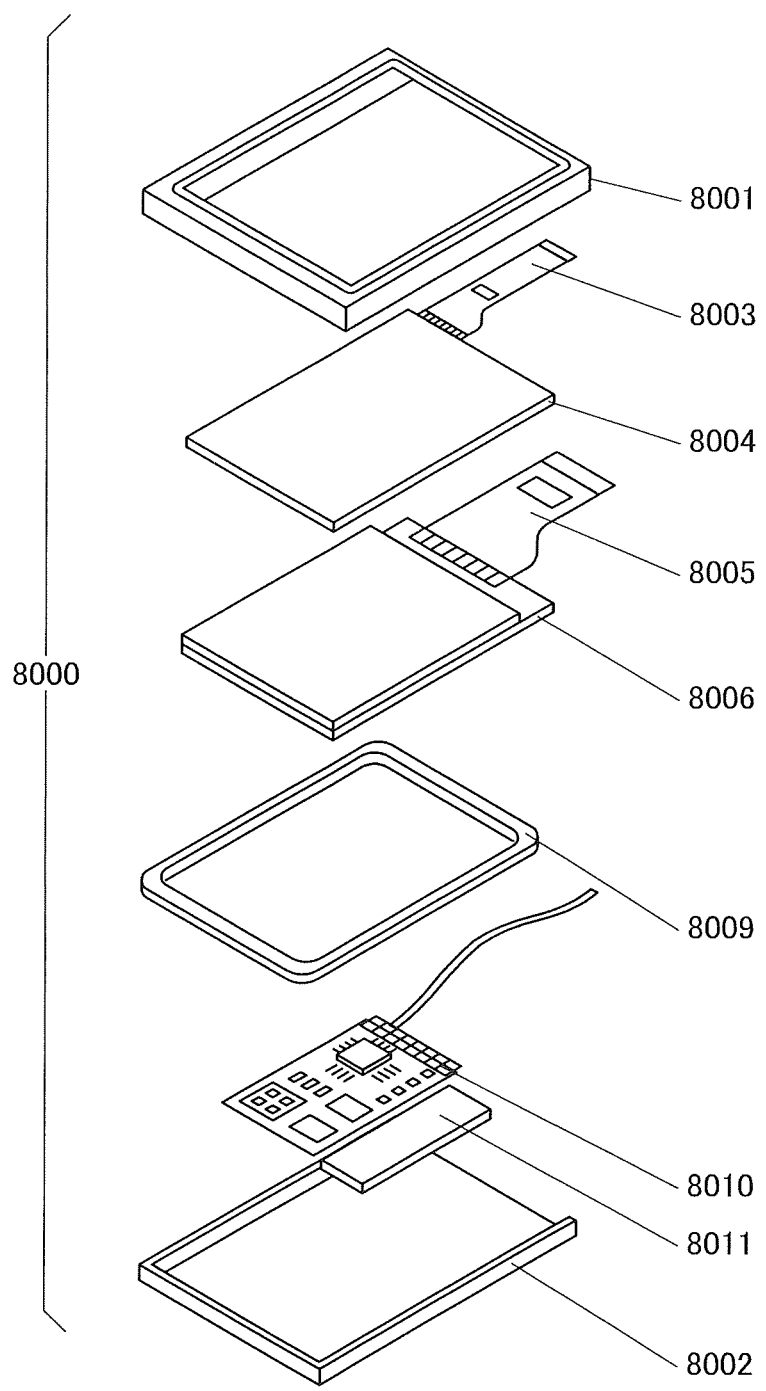
FIG. 15 is a perspective view of a display module according to one embodiment of the present invention.

In a display module 8000 in FIG. 15, a touch sensor 8004 connected to an FPC 8003, a display device 8006 connected to an FPC 8005, a frame 8009, a printed board 8010, and a battery 8011 are provided between an upper cover 8001 and a lower cover 8002.

The light-emitting element of one embodiment of the present invention can be used for the display device 8006, for example.

The shapes and sizes of the upper cover 8001 and the lower cover 8002 can be changed as appropriate in accordance with the sizes of the touch sensor 8004 and the display device 8006.

The touch sensor 8004 can be a resistive touch sensor or a capacitive touch sensor and may be formed to overlap with the display device 8006. A counter substrate (sealing substrate) of the display device 8006 can have a touch sensor function. A photosensor may be provided in each pixel of the display device 8006 so that an optical touch sensor is obtained.

The frame 8009 protects the display device 8006 and also functions as an electromagnetic shield for blocking electromagnetic waves generated by the operation of the printed board 8010. The frame 8009 may function as a radiator plate.

The printed board 8010 has a power supply circuit and a signal processing circuit for outputting a video signal and a clock signal. As a power source for supplying power to the power supply circuit, an external commercial power source or the battery 8011 provided separately may be used. The battery 8011 can be omitted in the case of using a commercial power source.

The display module 8000 can be additionally provided with a member such as a polarizing plate, a retardation plate, or a prism sheet.

<Electronic Devices>

FIGS. 16A to 16G illustrate electronic devices. These electronic devices can include a housing 9000, a display portion 9001, a speaker 9003, operation keys 9005 (including a power switch or an operation switch), a connection terminal 9006, a sensor 9007 (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 9008, and the like.

The electronic devices illustrated in FIGS. 16A to 16G can have a variety of functions, for example, a function of displaying a variety of data (a still image, a moving image, a text image, and the like) on the display portion, a touch sensor function, a function of displaying a calendar, date, time, and the like, a function of controlling a process with a variety of software (programs), a wireless communication function, a function of being connected to a variety of computer networks with a wireless communication function, a function of transmitting and receiving a variety of data with a wireless communication function, a function of reading a program or data stored in a memory medium and displaying the program or data on the display portion, and the like. Note that functions that can be provided for the electronic devices illustrated in FIGS. 16A to 16G are not limited to those described above, and the electronic devices can have a variety of functions. Although not illustrated in FIGS. 16A to 16G, the electronic devices may include a plurality of display portions. The electronic devices may have a camera or the like and a function of taking a still image, a function of taking a moving image, a function of storing the taken image in a memory medium (an external memory medium or a memory medium incorporated in the camera), a function of displaying the taken image on the display portion, or the like.

The electronic devices illustrated in FIGS. 16A to 16G is described in detail below.

Figure 16A:
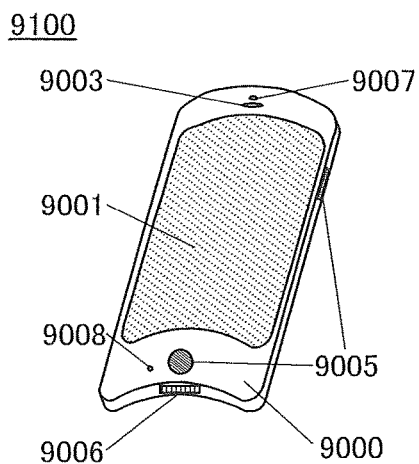
FIGS. 16A to 16G illustrate electronic devices according to one embodiment of the present invention.

FIG. 16A is a perspective view of a portable information terminal 9100. The display portion 9001 of the portable information terminal 9100 is flexible. Therefore, the display portion 9001 can be incorporated along a bent surface of a bent housing 9000. In addition, the display portion 9001 includes a touch sensor, and operation can be performed by touching the screen with a finger, a stylus, or the like. For example, when an icon displayed on the display portion 9001 is touched, an application can be started.

Figure 16D:
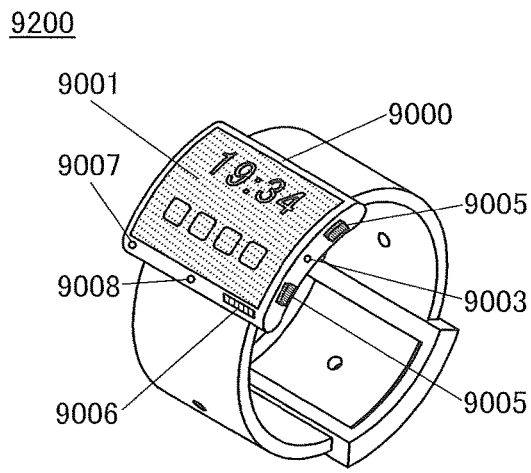
Figure 16B:
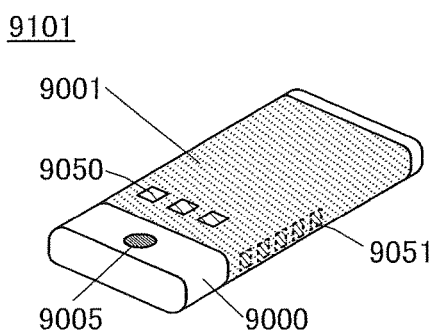

FIG. 16B is a perspective view of a portable information terminal 9101. The portable information terminal 9101 functions as, for example, one or more of a telephone set, a notebook, and an information browsing system. Specifically, the portable information terminal can be used as a smartphone. Note that the speaker 9003, the connection terminal 9006, the sensor 9007, and the like, which are not illustrated in FIG. 16B, can be positioned in the portable information terminal 9101 as in the portable information terminal 9100 illustrated in FIG. 16A. The portable information terminal 9101 can display characters and image information on its plurality of surfaces. For example, three operation buttons 9050 (also referred to as operation icons, or simply, icons) can be displayed on one surface of the display portion 9001. Furthermore, information 9051 indicated by dashed rectangles can be displayed on another surface of the display portion 9001. Examples of the information 9051 include display indicating reception of an incoming email, social networking service (SNS) message, call, and the like; the title and sender of an email and SNS message; the date; the time; remaining battery; and the reception strength of an antenna. Instead of the information 9051, the operation buttons 9050 or the like may be displayed on the position where the information 9051 is displayed.

Figure 16E:
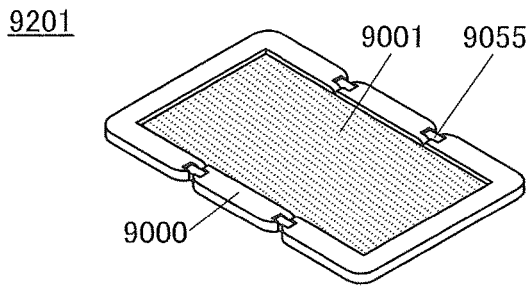
Figure 16C:
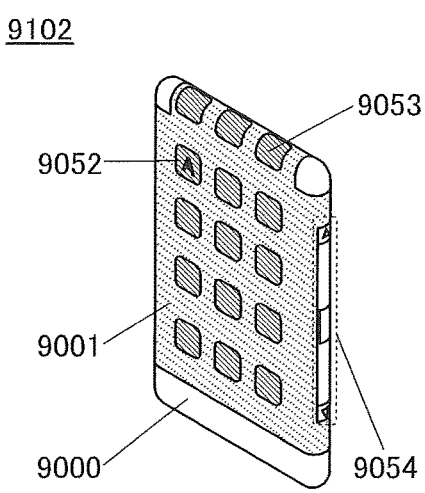

FIG. 16C is a perspective view of a portable information terminal 9102. The portable information terminal 9102 has a function of displaying information on three or more surfaces of the display portion 9001. Here, information 9052, information 9053, and information 9054 are displayed on different surfaces. For example, a user of the portable information terminal 9102 can see the display (here, the information 9053) with the portable information terminal 9102 put in a breast pocket of his/her clothes. Specifically, a caller's phone number, name, or the like of an incoming call is displayed in a position that can be seen from above the portable information terminal 9102. Thus, the user can see the display without taking out the portable information terminal 9102 from the pocket and decide whether to answer the call.

FIG. 16D is a perspective view of a watch-type portable information terminal 9200. The portable information terminal 9200 is capable of executing a variety of applications such as mobile phone calls, e-mailing, viewing and editing texts, music reproduction, Internet communication, and computer games. The display surface of the display portion 9001 is bent, and images can be displayed on the bent display surface. The portable information terminal 9200 can employ near field communication that is a communication method based on an existing communication standard. In that case, for example, mutual communication between the portable information terminal 9200 and a headset capable of wireless communication can be performed, and thus hands-free calling is possible. The portable information terminal 9200 includes the connection terminal 9006, and data can be directly transmitted to and received from another information terminal via a connector. Power charging through the connection terminal 9006 is possible. Note that the charging operation may be performed by wireless power feeding without using the connection terminal 9006.

Figure 16F:
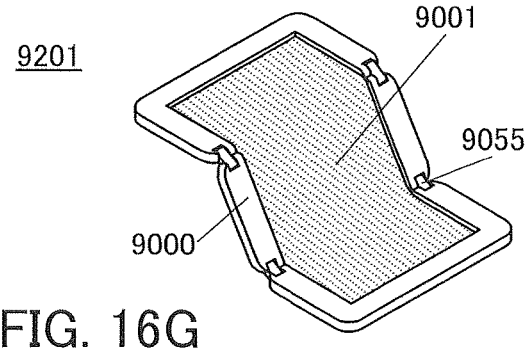
Figure 16G:
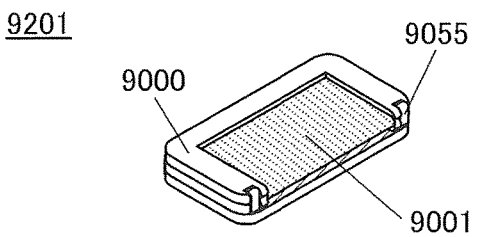

FIGS. 16E, 16F, and 16G are perspective views of a foldable portable information terminal 9201. FIG. 16E is a perspective view illustrating the portable information terminal 9201 that is opened. FIG. 16F is a perspective view illustrating the portable information terminal 9201 that is being opened or being folded. FIG. 16G is a perspective view illustrating the portable information terminal 9201 that is folded. The portable information terminal 9201 is highly portable when folded. When the portable information terminal 9201 is opened, a seamless large display region is highly browsable. The display portion 9001 of the portable information terminal 9201 is supported by three housings 9000 joined together by hinges 9055. By folding the portable information terminal 9201 at a connection portion between two housings 9000 with the hinges 9055, the portable information terminal 9201 can be reversibly changed in shape from an opened state to a folded state. For example, the portable information terminal 9201 can be bent with a radius of curvature of greater than or equal to 1 mm and less than or equal to 150 mm.

The electronic devices described in this embodiment each include the display portion for displaying some sort of data. Note that the light-emitting element of one embodiment of the present invention can also be used for an electronic device which does not have a display portion. The structure in which the display portion of the electronic device described in this embodiment is flexible and display can be performed on the bent display surface or the structure in which the display portion of the electronic device is foldable is described as an example; however, the structure is not limited thereto and a structure in which the display portion of the electronic device is not flexible and display is performed on a plane portion may be employed.

Note that the structure described in this embodiment can be combined as appropriate with any of the structures described in the other embodiments.

Embodiment 10

In this embodiment, examples of lighting devices in which the light-emitting element of one embodiment of the present invention is used are described with reference to FIG. 17.

Figure 17:
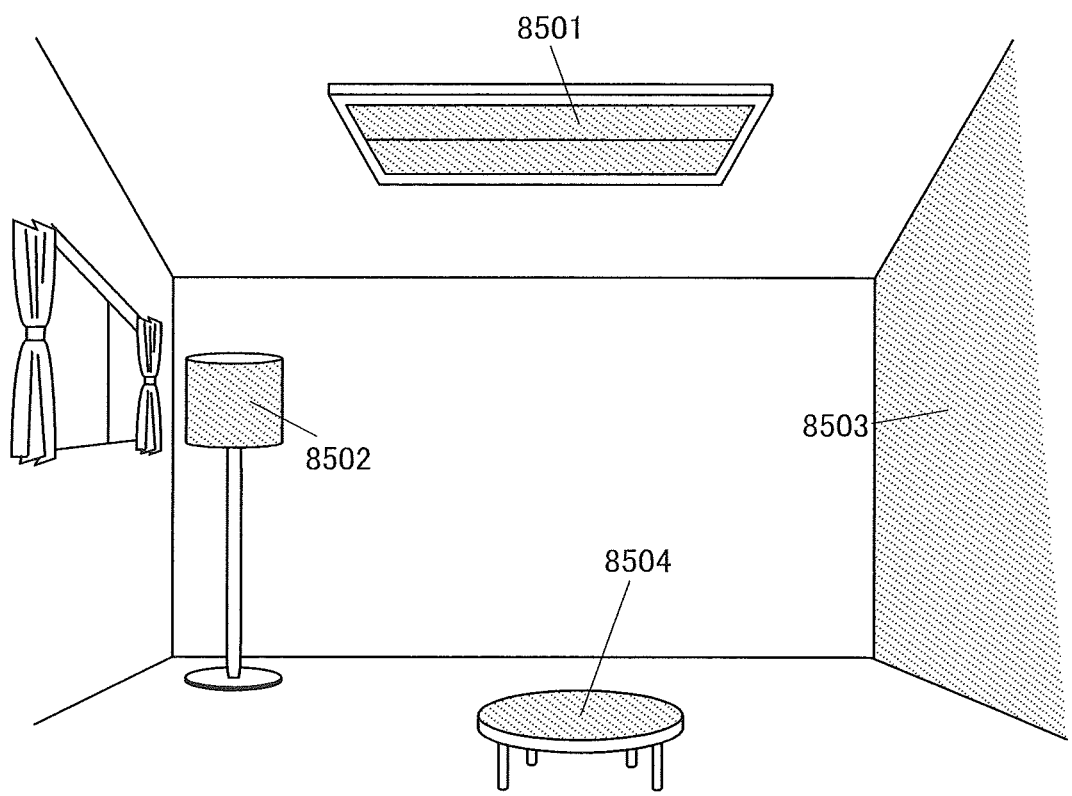
FIG. 17 illustrates lighting devices according to one embodiment of the present invention.

FIG. 17 illustrates an example in which the light-emitting element is used for an indoor lighting device 8501. Since the light-emitting element can have a larger area, a lighting device having a large area can also be formed. In addition, a lighting device 8502 in which a light-emitting region has a curved surface can also be formed with the use of a housing with a curved surface. A light-emitting element described in this embodiment is in the form of a thin film, which allows the housing to be designed more freely. Therefore, the lighting device can be elaborately designed in a variety of ways. Furthermore, a wall of the room may be provided with a large-sized lighting device 8503. Touch sensors may be provided in the lighting devices 8501, 8502, and 8503 to control the power on/off of the lighting devices.

Moreover, when the light-emitting element is used on the surface side of a table, a lighting device 8504 which has a function as a table can be obtained. When the light-emitting element is used as part of other furniture, a lighting device which has a function as the furniture can be obtained.

In this manner, a variety of lighting devices to which the light-emitting element is applied can be obtained. Note that such lighting devices are also embodiments of the present invention.

Note that the structure described in this embodiment can be combined as appropriate with any of the structures described in the other embodiments.

Example 1

In this example, a method of synthesizing an example of the benzo[a]anthracene compound which is described in Embodiment 2 and represented by the general formula (G1), i.e., 9-[4-(7-benzo[a]anthracene)phenyl]-9H-carbazole (abbreviation: 7CzPaBA, structure formula (100)), is described in detail.

<Synthesis of 7CzPaBA>

In a 200-mL three-neck flask were put 3.0 g (9.7 mmol) of 7-bromobenzo[a]anthracene, 4.4 g (15.4 mmol) of 4-(9H-carbazol-9-yl)phenylboronic acid, and 1.1 g (10.5 mmol) of sodium carbonate, and the air in the flask was replaced with nitrogen. To this mixture were added 35.0 mL of toluene, 12.5 mL of ethanol, and 9.7 mL of water, and the mixture was stirred to be degassed while the pressure in the flask was reduced. After that, 0.1 g (0.1 mmol) of tetrakis(triphenylphosphine)palladium was added, and the mixture was stirred at 90° C. for 3.0 hours. Then, this mixture was suction filtered, and a residue and a filtrate were separated. The obtained residue was dissolved in toluene, and the mixture was suction filtered through Florisil, Celite, and alumina to give a filtrate. The obtained filtrate was concentrated to give a solid. The obtained solid was washed with toluene, so that 1.8 g of the object of the synthesis was obtained in a yield of 39%. This reaction scheme is shown below.

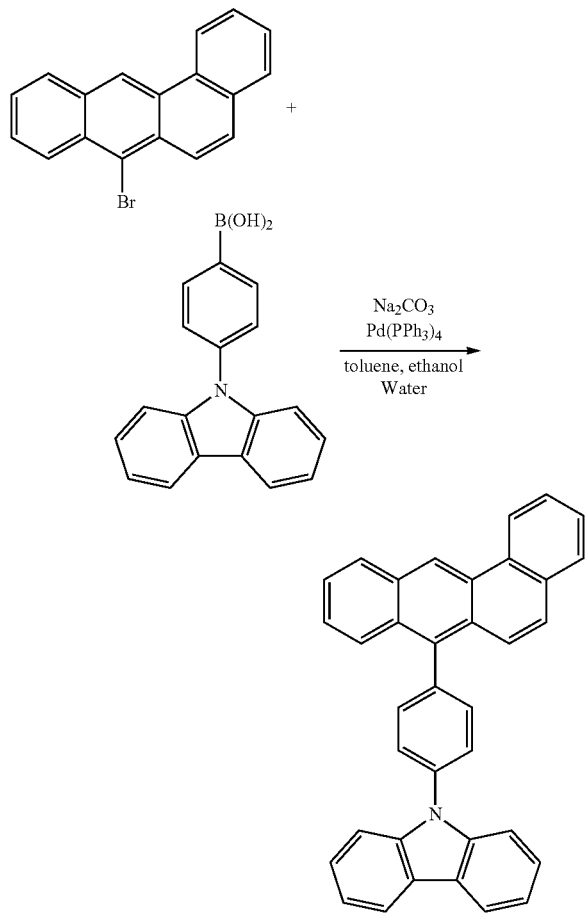

Using a train sublimation method, 1.8 g of the obtained solid was purified by sublimation. In the purification, the solid was heated at 240° C. under a pressure of 3.2 Pa with a flow rate of argon gas of 5.0 mL/min. After the sublimation purification, 1.7 g of the object of the synthesis solid was obtained at a collection rate of 94%.

Figure 18A:
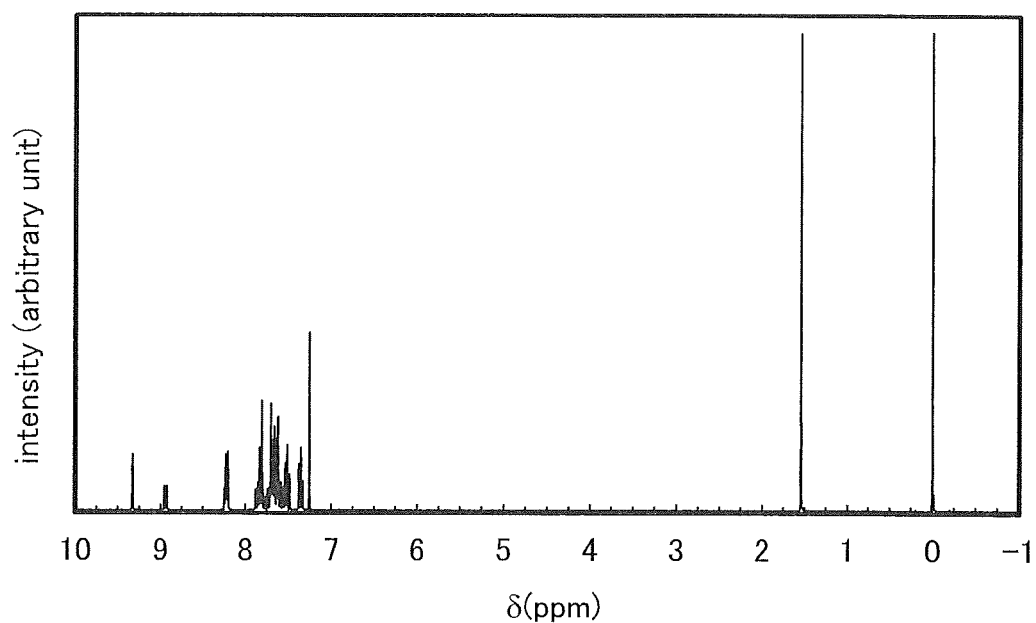
FIGS. 18A and 18B show NMR charts of compounds according to Example 1.
Figure 18B:
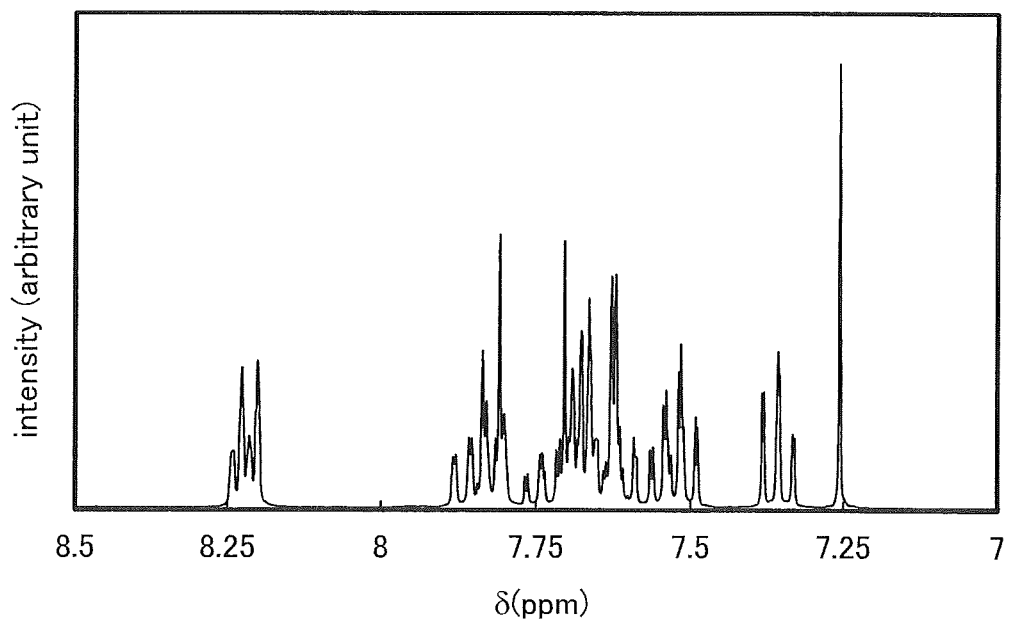

Nuclear magnetic resonance ($^1$H NMR) spectroscopy identified this compound as 7CzPaBA, which was the object of the synthesis. The $^1$H NMR data of the obtained substance is given below. In addition, $^1$H NMR charts of the obtained substance are shown in FIGS. 18A and 18B.

$^1$H NMR (CDCl$_3$, 300 MHz): δ=7.36 (ddd, J=7.7, 7.7, 0.9 Hz, 2H), 7.49-7.88 (m, 16H), 8.20-8.24 (m, 3H), 8.94 (d, J=7.8 Hz, 1H), 9.33 (s, 1H).

<Characteristics of 7CzPaBA>

Thermogravimetry-differential thermal analysis (TG-DTA) of obtained 7CzPaBA was performed. A high vacuum differential type differential thermal balance (TG/DTA 2410SA, manufactured by Bruker AXS K.K.) was used for the measurement. The measurement was carried out under a nitrogen stream (a flow rate of 200 mL/min) and a normal pressure at a temperature rising rate of 10° C./min. From the relationship between weight and temperature (thermogravimetry), it was understood that the 5% weight loss temperature was 369° C., which is indicative of high heat resistance.

Figure 19A:
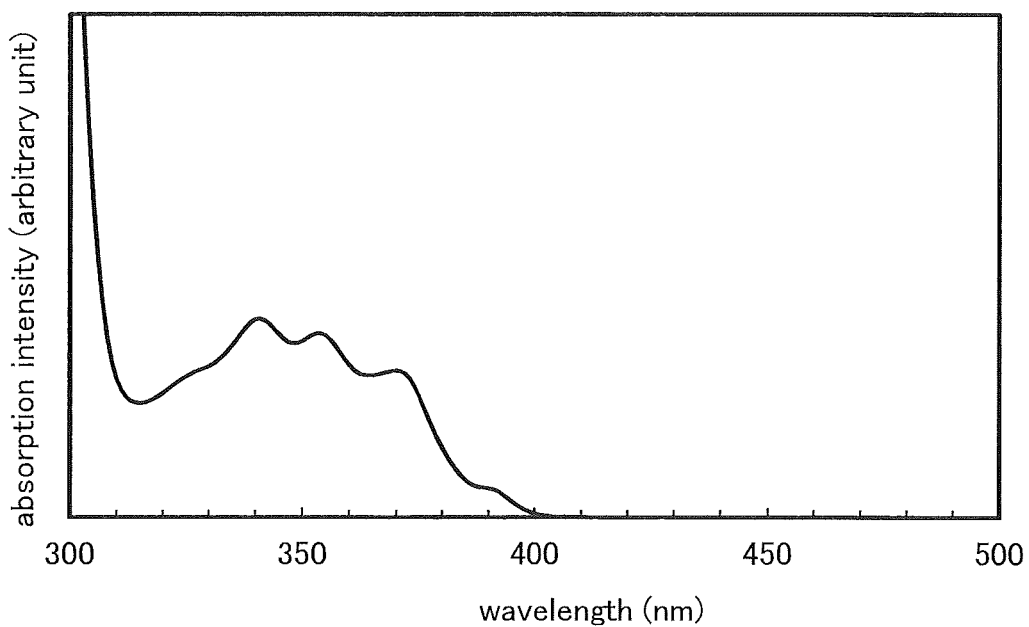
FIGS. 19A and 19B show absorption and emission spectra of the compound according to Example 1.
Figure 19B:
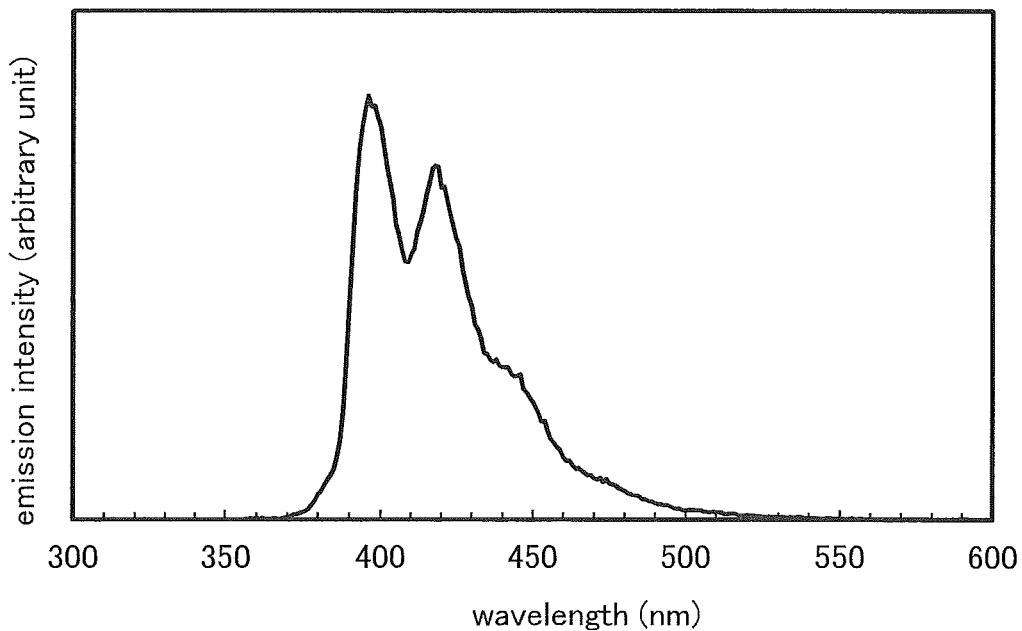
Figure 20A:
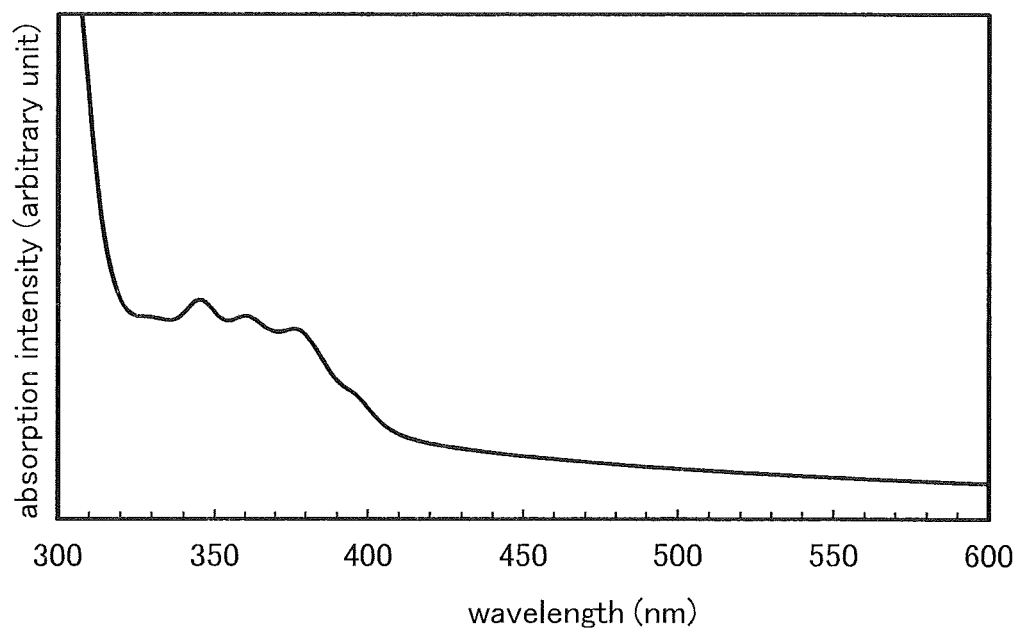
FIGS. 20A and 20B show absorption and emission spectra of the compound according to Example 1.
Figure 20B:
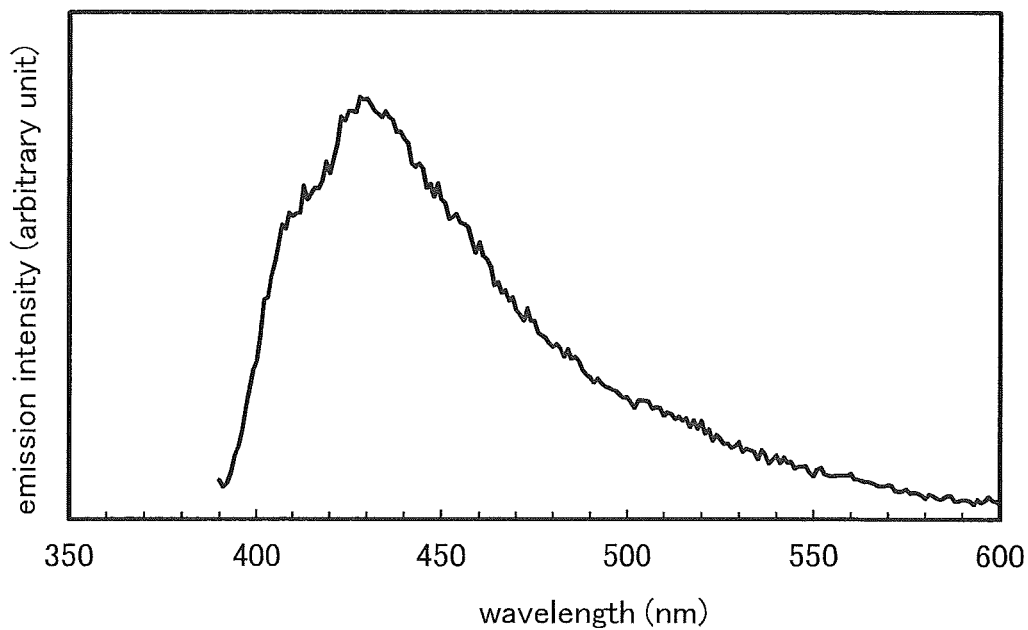

Absorption and emission spectra of 7CzPaBA in a toluene solution of 7CzPaBA are shown in FIGS. 19A and 19B, and absorption and emission spectra of a thin film of 7CzPaBA are shown in FIGS. 20A and 20B.

The absorption spectra were measured using an ultraviolet-visible spectrophotometer (V-550 type manufactured by JASCO Corporation). The absorption spectrum of 7CzPaBA in the toluene solution was obtained by subtraction of absorption spectra of toluene and a quartz cell from absorption spectra of the toluene solution of 7CzPaBA put in the quartz cell, and is shown in the figure. The absorption spectrum of the thin film was obtained by subtraction of an absorption spectrum of quartz from absorption spectra of a sample formed by evaporation of 7CzPaBA on a quartz substrate, and is shown in the figure. The emission spectra were measured with a PL-EL measurement apparatus (manufactured by Hamamatsu Photonics K.K.). The emission spectrum of 7CzPaBA in the toluene solution was measured with the toluene solution of 7CzPaBA put in a quartz cell. The emission spectrum of the thin film was measured with a sample formed by evaporation of 7CzPaBA on a quartz substrate. The thin film whose absorption and emission spectra were measured was formed over a quartz substrate by a vacuum evaporation method. The thickness of the thin film was 50 nm.

The maximum absorption wavelengths of 7CzPaBA in the toluene solution were around 392 nm, around 370 nm, around 355 nm, and around 341 nm. The maximum emission wavelengths thereof were around 396 nm and around 418 nm (an excitation wavelength of 342 nm). Furthermore, the maximum absorption wavelengths of the thin film were around 395 nm, around 376 nm, around 360 nm, around 345 nm, around 331 inn, and around 301 nm. The longest maximum emission wavelength thereof was around 429 nm (an excitation wavelength of 378 nm).

The ionization potential of the thin film of 7CzPaBA was measured in the air with a photoelectron spectrometer (AC-3, produced by Riken Keiki, Co., Ltd.). The obtained value of the ionization potential was converted into a negative value, and the HOMO level of 7CzPaBA was −6.02 eV. From the data of the absorption spectrum of the thin film in FIG. 20A, the absorption edge of 7CzPaBA −02, which was obtained from Tauc plot with an assumption of direct transition, was 2.98 eV. Thus, the optical energy gap of 7CzPaBA in the solid state was estimated at 2.98 eV; from the values of the HOMO level obtained above and this energy gap, the lowest unoccupied molecular orbital level (also referred to as LUMO level) of 7CzPaBA can be estimated at −3.04 eV. This reveals that 7CzPaBA in the solid state has an energy gap as wide as 2.98 eV.

Example 2

In this example, a light-emitting element of one embodiment of the present invention in which a delayed fluorescence component due to TTA accounts for a large proportion of emissive components is described in detail using FIGS. 21A and 21B, FIG. 22, FIG. 23, and FIG. 24.

In this example, light-emitting elements (a light-emitting element 1 and a light-emitting element 2) each corresponding to the light-emitting element 150 in FIG. 1A and comparative light-emitting elements (a comparative light-emitting element 1 and a comparative light-emitting element 2) were fabricated, and the fluorescence lifetimes and characteristics of the light-emitting elements were measured.

The structures and abbreviations of the compounds used are given below.

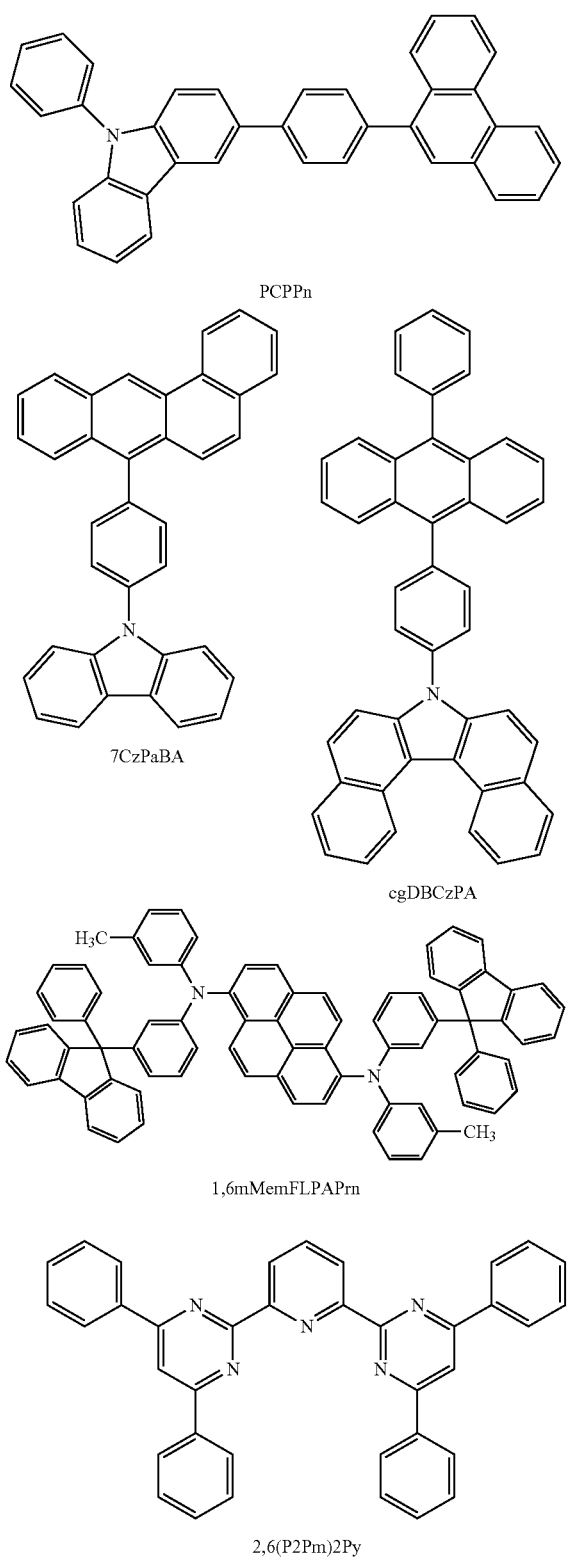

<Fabrication of Light-Emitting Elements>
<<Fabrication of Light-Emitting Element 1>>

As the electrode 101, a film of indium tin oxide containing silicon oxide (abbreviation: ITSO) was formed to a thickness of 110 nm over a substrate. Note that the area of the electrode 101 was 4 mm² (2 mm×2 mm).

Next, the EL layer 100 in which a plurality of layers were stacked was formed over the electrode 101. As the hole-injection layer 111, 3-[4-(9-phenanthryl)-phenyl]-9-phenyl-9H-carbazole (abbreviation: PCPPn) and molybdenum oxide (MoO₃) were deposited by co-evaporation to a thickness of 60 nm such that the weight ratio of PCPPn to MoO₃ was 1:0.5. Note that co-evaporation is an evaporation method in which a plurality of different substances are concurrently vaporized from respective different evaporation sources. As the hole-transport layer 112, PCPPn was deposited by evaporation to a thickness of 30 nm.

Next, as the light-emitting layer 130, 9-[4-(7-benzo[a]anthracene)phenyl]-9H-carbazole (abbreviation: 7CzPaBA) was deposited to a thickness of 25 nm.

Over the light-emitting layer 130, 2,2'-(pyridine-2,6-diyl)bis(4,6-diphenylpyrimidine) (abbreviation: 2,6(P2Pm)2Py) was deposited to a thickness of 25 nm as the electron-transport layer 118. Next, as the electron-injection layer 119, lithium fluoride (LiF) was deposited by evaporation to a thickness of 1 nm.

As the electrode 102, aluminum (Al) was deposited to a thickness of 200 nm.

Next, in a glove box containing a nitrogen atmosphere, the light-emitting element 1 was sealed by fixing a sealing substrate to the substrate provided with the EL layer 100 using a sealant for an organic EL device. Specifically, a sealant was applied to surround the EL layer 100 formed over the substrate, the substrate was bonded to the sealing substrate, and irradiation with ultraviolet light having a wavelength of 365 nm at 6 J/cm² and heat treatment at 80° C. for one hour were performed. Through the above steps, the light-emitting element 1 was obtained.

<<Fabrication of Light-Emitting Element 2 and Comparative Light-Emitting Elements 1 and 2>>

The light-emitting element 2 and the comparative light-emitting elements 1 and 2 were fabricated through the same steps as those for the above-mentioned light-emitting element 1 except for the step of forming the light-emitting layer 130.

As the light-emitting layer 130 of the light-emitting element 2, 7CzPaBA and N,N'-bis(3-methylphenyl)-N,N'-bis[3-(9-phenyl-9H-fluoren-9-yl)phenyl]pyrene-1,6-diamine (abbreviation: 1,6mMemFLPAPm) were deposited by co-evaporation to a thickness of 25 nm such that the weight ratio of 7CzPaBA to 1,6mMemFLPAPrn was 1:0.03. In the light-emitting layer 130, 7CzPaBA serves as a host material and 1,6mMemFLPAPm serves as a guest material (fluorescent material).

As the light-emitting layer 130 of the comparative light-emitting element 1, 7-[4-(10-phenyl-9-anthryl)phenyl]-7H-dibenzo[c,g]carbazole (abbreviation: cgDBCzPA) was deposited to a thickness of 25 nm.

As the light-emitting layer 130 of the comparative light-emitting element 2, cgDBCzPA and 1,6mMemFLPAPm were deposited by co-evaporation to a thickness of 25 mu such that the weight ratio of cgDBCzPA to 1,6mMemFL-PAPrn was 1:0.03. In the light-emitting layer 130, cgDBCzPA serves as a host material and 1,6mMemFLPAPm serves as a guest material (fluorescent material).

Element structures of the fabricated light-emitting elements (the light-emitting elements 1 and 2 and the comparative light-emitting elements 1 and 2) are shown in detail in Table 2.

TABLE 2

|  | Layer | Reference numeral | Thickness (nm) | Material | Weight ratio |
|---|---|---|---|---|---|
| Light-emitting element 1 | Electrode | 102 | 200 | Al | — |
|  | Electron-injection layer | 119 | 1 | LiF | — |
|  | Electron-transport layer | 118 | 25 | 2,6(P2Pm)2Py | — |
|  | Light-emitting layer | 130 | 25 | 7CzPaBA | — |
|  | Hole-transport layer | 112 | 30 | PCPPn | — |
|  | Hole-injection layer | 111 | 60 | PCPPn:MoO$_3$ | 1:0.5 |
|  | Electrode | 101 | 110 | ITSO | — |
| Light-emitting element 2 | Electrode | 102 | 200 | Al | — |
|  | Electron-injection layer | 119 | 1 | LiF | — |
|  | Electron-transport layer | 118 | 25 | 2,6(P2Pm)2Py | — |
|  | Light-emitting layer | 130 | 25 | 7CzPaBA:1,6mMemFLPAPrn | 1:0.03 |
|  | Hole-transport layer | 112 | 30 | PCPPn | — |
|  | Hole-injection layer | 111 | 60 | PCPPn:MoO$_3$ | 1:0.5 |
|  | Electrode | 101 | 110 | ITSO | — |
| Comparative light-emitting element 1 | Electrode | 102 | 200 | Al | — |
|  | Electron-injection layer | 119 | 1 | LiF | — |
|  | Electron-transport layer | 118 | 25 | 2,6(P2Pm)2Py | — |
|  | Light-emitting layer | 130 | 25 | cgDBCzPA | — |
|  | Hole-transport layer | 112 | 30 | PCPPn | — |
|  | Hole-injection layer | 111 | 60 | PCPPn:MoO$_3$ | 1:0.5 |
|  | Electrode | 101 | 110 | ITSO | — |
| Comparative light-emitting element 2 | Electrode | 102 | 200 | Al | — |
|  | Electron-injection layer | 119 | 1 | LiF | — |
|  | Electron-transport layer | 118 | 25 | 2,6(P2Pm)2Py | — |
|  | Light-emitting layer | 130 | 25 | cgDBCzPA:1,6mMemFLPAPrn | 1:0.03 |
|  | Hole-transport layer | 112 | 30 | PCPPn | — |
|  | Hole-injection layer | 111 | 60 | PCPPn:MoO$_3$ | 1:0.5 |
|  | Electrode | 101 | 110 | ITSO | — |

<Measurements of Fluorescence Lifetimes>

Figure 21A:
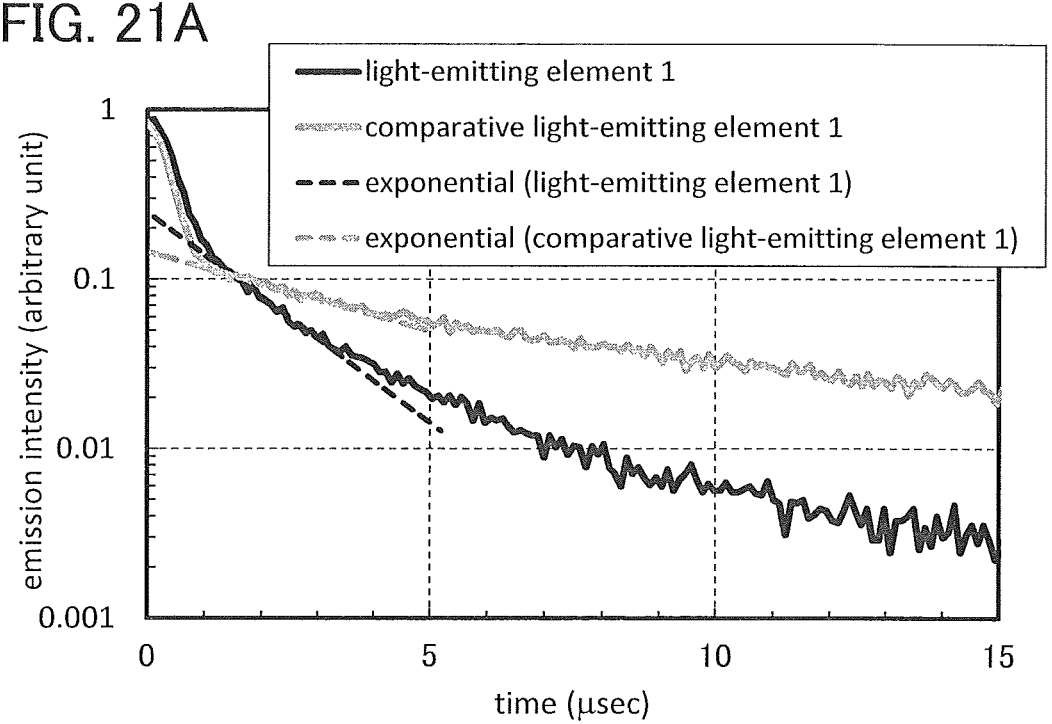
FIGS. 21A and 21B show fluorescence lifetime characteristics of light-emitting elements according to Example 2.
Figure 21B:
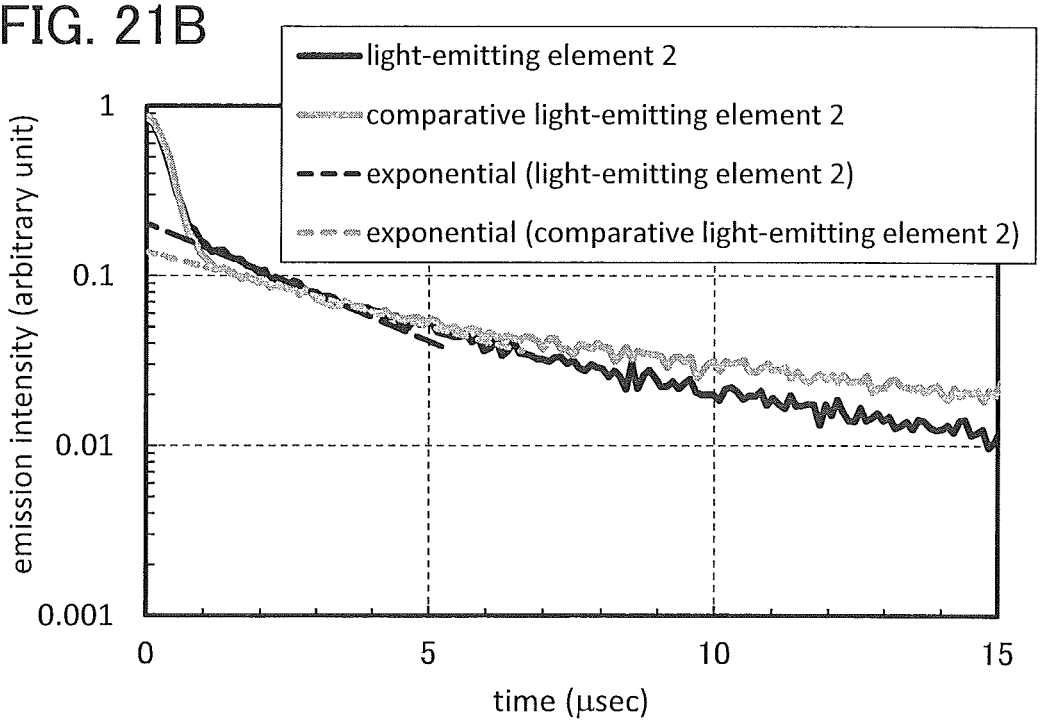

The fluorescence lifetimes of the light-emitting elements 1 and 2 and the comparative light-emitting elements 1 and 2 were measured. For the light-emitting element 1, blue light emitted from 7CzPaBA was observed. For the comparative light-emitting element 1, blue light emitted from cgDBCzPA was observed. For the light-emitting element 2 and the comparative light-emitting element 2, blue light emitted from 1,6mMemFLPAPm, which is a fluorescent material, was observed. A picosecond fluorescence lifetime measurement system (manufactured by Hamamatsu Photonics K.K.) was used for the measurements. To measure the lifetimes of fluorescence in the light-emitting elements, a square wave pulse voltage was applied to the light-emitting elements, and time-resolved measurements of light, which was attenuated from the falling of the voltage, was performed using a streak camera. The pulse voltage was applied at a frequency of 10 Hz. By integrating data obtained by repeated measurements, data with a high S/N ratio was obtained. The measurements were performed at room temperature (300 K). A pulse voltage of 5.0 V (for the light-emitting elements 1 and 2) and a pulse voltage of 3.5 V (for the comparative light-emitting elements 1 and 2) were applied while being adjusted so that currents flowing in the light-emitting elements have similar values. The measurements were performed under the conditions of a pulse time width of 100 μsec, a negative bias voltage of −5V, and a measurement time of 50 μs. The measurement results of the fluorescence lifetimes of the light-emitting elements are shown in FIGS. 21A and 21B. In FIGS. 21A and 21B, the vertical axis represents emission intensity normalized to that in a state where carriers are steadily injected (when the pulse voltage is ON), and the horizontal axis represents time elapsed after the falling of the pulse voltage.

The attenuation curves shown in FIGS. 21A and 21B were fitted with an exponential. As a result of the fitting, the fluorescence lifetimes τ of the light-emitting elements 1 and 2 were estimated at 2.1 μs and 2.2 μs, respectively, and the fluorescence lifetimes τ of the comparative light-emitting elements 1 and 2 were estimated at 3.2 μs and 3.1 μs, respectively. Since the lifetime of fluorescence is generally several nanoseconds, light observed from each of the light-emitting elements 1 and 2 and the comparative light-emitting elements 1 and 2 is probably fluorescence including a delayed fluorescence component.

In the fluorescence measurements described with reference to FIGS. 21A and 21B, possible causes of the delayed fluorescence other than the formation of a singlet exciton due to triplet-triplet annihilation (TTA) include the formation of a singlet exciton due to recombination of carriers remaining in the light-emitting elements when the pulse voltage is OFF. In these measurements, however, since a negative bias voltage (−5 V) was applied, recombination of the remaining carriers was suppressed. Therefore, the delayed fluorescence components shown in the measurement results in FIGS. 21A and 21B were attributed to light emission due to triplet-triplet annihilation (TTA).

Next, the proportion of the delayed fluorescence component in the total emissive components was calculated. The proportion of the delayed fluorescence component in each light-emitting element is shown in Table 3.

TABLE 3

| | Proportion of delayed fluorescence in emissive components |
|---|---|
| Light-emitting element 1 | 25% |
| Light-emitting element 2 | 20% |
| Comparative light-emitting element 1 | 15% |
| Comparative light-emitting element 2 | 12% |

The results show that the proportion of the delayed fluorescence component in the light-emitting element 1 is 25% and higher than that in the comparative light-emitting element 1. This reveals that TTA occurs more in the light-emitting element 1 including 7CzPaBA, which has a benzo[a]anthracene skeleton, in the light-emitting layer than in the comparative light-emitting element 1 including cgDBCzPA, which has an anthracene skeleton, in the light-emitting layer.

The results show that the proportion of the delayed fluorescence component in the light-emitting element 2 is 20% and higher than that in the comparative light-emitting element 2. This reveals that, even when light emitted from 1,6mMemFLPAPm as the guest material (fluorescent dopant) is observed in both elements, TTA occurs more in the light-emitting element 2 including 7CzPaBA, which has a benzo[a]anthracene skeleton, as the host material than in the comparative light-emitting element 2 including cgDBCzPA, which has an anthracene skeleton, as the host material.

<Emission Characteristics Light-Emitting Elements>

Then, emission characteristics of the fabricated light-emitting elements 1 and 2 and comparative light-emitting elements 1 and 2 were measured. Note that the measurements were performed at room temperature (in an atmosphere kept at 25° C.).

Figure 22:
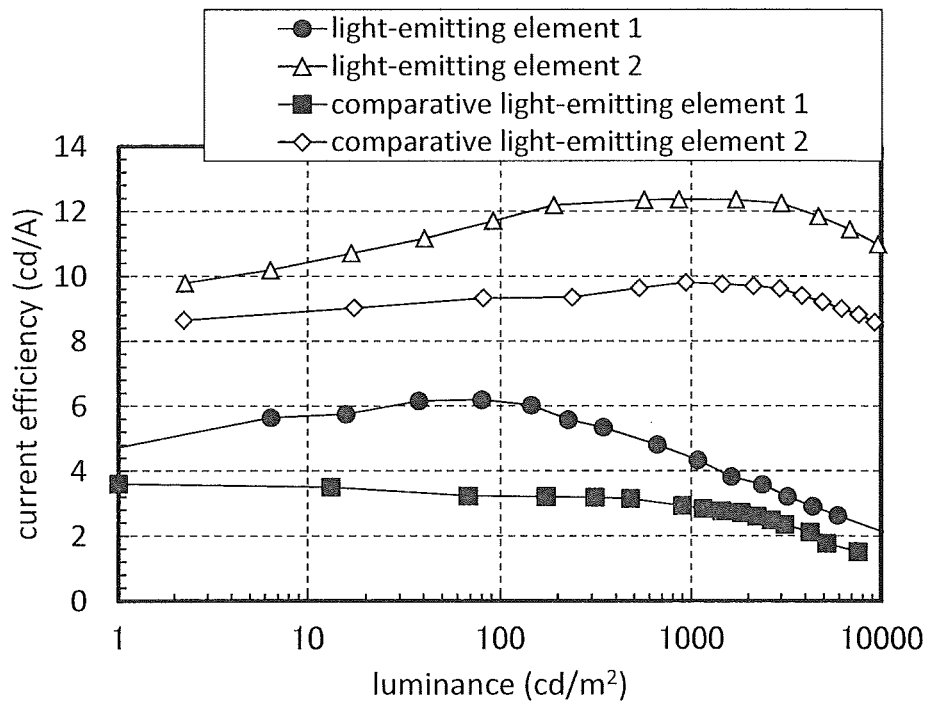
FIG. 22 shows current efficiency-luminance characteristics of the light-emitting elements according to Example 2.

The emission characteristics of the light-emitting elements at a luminance around 1000 cd/m² are shown below in Table 4. FIG. 22 shows current efficiency-luminance characteristics of the light-emitting elements, FIG. 23 external quantum efficiency-luminance characteristics thereof, and FIG. 24 luminance-voltage characteristics thereof.

TABLE 4

| | Voltage (v) | Electric current density (mA/cm²) | CIE chromaticity (x, y) | Luminance (cd/m²) | Current efficiency (cd/A) | External quantum efficiency (%) |
|---|---|---|---|---|---|---|
| Light-emitting element 1 | 4.4 | 25.0 | (0.17, 0.11) | 1090 | 4.3 | 4.7 |
| Light-emitting element 2 | 4.0 | 7.0 | (0.15, 0.19) | 861 | 12.4 | 9.4 |
| Comparative light-emitting element 1 | 3.4 | 30.6 | (0.15, 0.05) | 900 | 2.9 | 5.4 |
| Comparative light-emitting element 2 | 3.1 | 9.6 | (0.14, 0.16) | 939 | 9.8 | 8.5 |

Emission spectrum peaks of the light-emitting element 1 and the comparative light-emitting element 1 are at 435 nm and 440 nm, respectively. Blue light emitted from 7CzPaBA and cgDBCzPA was observed in the light-emitting element 1 and the comparative light-emitting element 1, respectively. Emission spectrum peaks of the light-emitting element 2 and the comparative light-emitting element 2 are at 466 nm and 464 nm, respectively. Blue light emitted from 1,6mMem-FLPAPm as a fluorescent material was observed in the light-emitting element 2 and the comparative light-emitting element 2. Thus, each light-emitting element emits blue light with an emission spectrum peak at a wavelength greater than or equal to 400 nm and less than or equal to 550 nm. Since only light emitted from the fluorescent material is observed in the light-emitting element 2 and the comparative light-emitting element 2; singlet excited energy generated by TTA is transferred from the host material to the fluorescent material.

Figure 23:
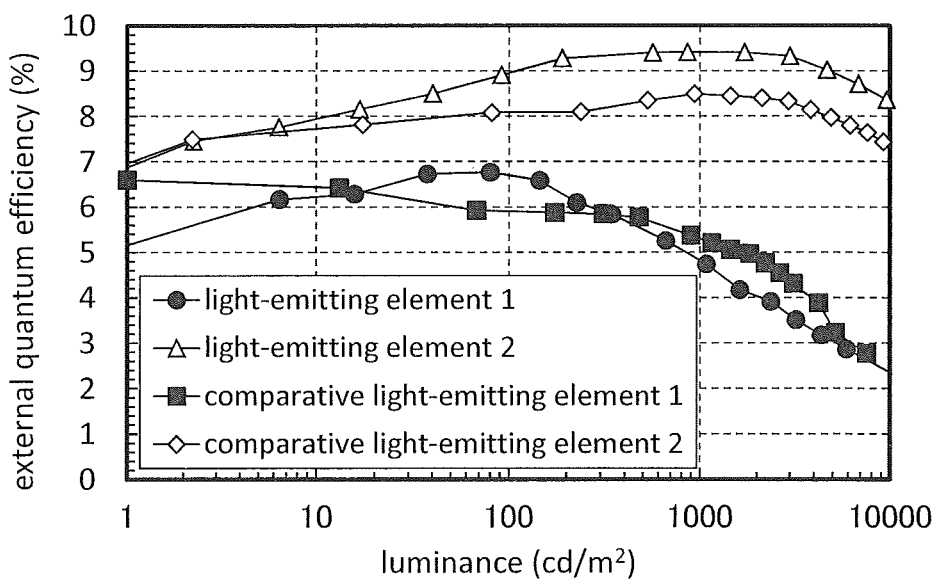
FIG. 23 shows external quantum efficiency-luminance characteristics of the light-emitting elements according to Example 2.
Figure 24:
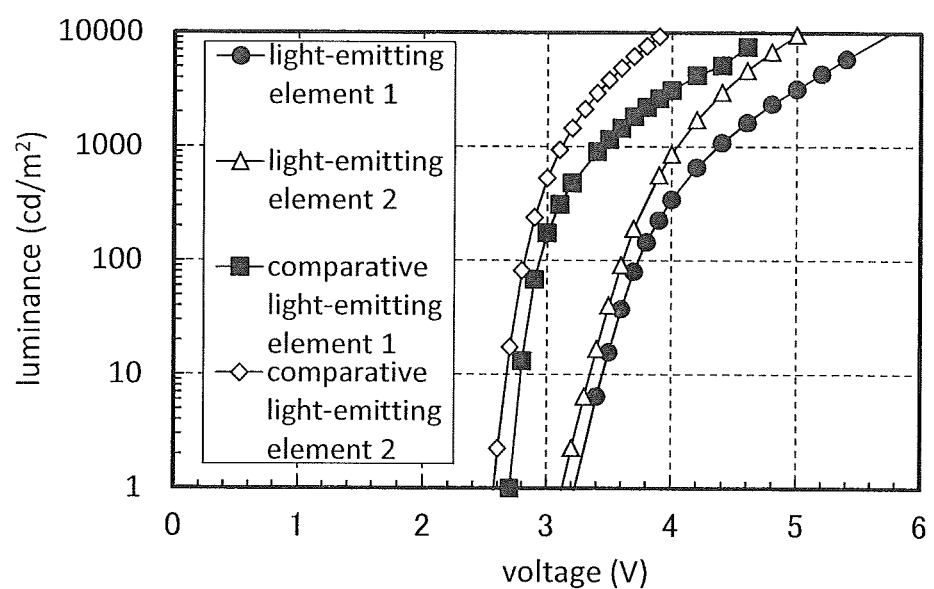
FIG. 24 shows luminance-voltage characteristics of the light-emitting elements according to Example 2.

The results in FIG. 22, FIG. 23, and Table 4 show that the light-emitting element 1 has higher efficiency than the comparative light-emitting element 1 and that the light-emitting element 2 has higher efficiency than the comparative light-emitting element 2. The results indicate that the light-emitting elements 1 and 2 each including 7CzPaBA in the light-emitting layer have higher emission efficiency than the comparative light-emitting elements 1 and 2 including cgDBCzPA in the light-emitting layer. The blue light-emitting elements with high emission efficiency were thus achieved using, in the light-emitting layer, 7CzPaBA which has a benzo[a]anthracene skeleton and in which a delayed fluorescence component due to TTA accounts for 20% or more.

The above-described structure can provide a light-emitting element in which a delayed fluorescence component due to TTA accounts for 20% or more of emissive components and which has an emission spectrum peak in the blue wavelength range. The above-described structure can provide a light-emitting element in which a delayed fluorescence component due to TTA accounts for 20% or more of emissive components and which has at least one emission spectrum peak at a wavelength greater than or equal to 400 nm and less than or equal to 550 nm.

<Measurements of Singlet Excited Energy Levels and Triplet Excited Energy Levels>

A factor of the delayed fluorescence in the fluorescence measurements described with reference to FIGS. 21A and 21B may be thermally activated delayed fluorescence due to reverse intersystem crossing from the triplet excited state to the singlet excited state. To efficiently cause the reverse intersystem crossing, an energy difference between the $S_1$ level and the $T_1$ level is preferably 0.2 eV or less. For this reason, to confirm whether the delayed fluorescence revealed from FIGS. 21A and 21B is due to TTA, the $S_1$ levels and $T_1$ levels of the materials of the light-emitting layer in each of the above light-emitting elements were measured.

The $S_1$ levels and $T_1$ levels of 7CzPaBA, cgDBCzPA, and 1,6mMemFLPAPm were measured. Note that the light-emitting elements of one embodiment of the present invention are fluorescent light-emitting elements. In the case of a fluorescent organic material, since intersystem crossing is not likely to occur and light emitted from the $T_1$ level is faint, measurement of the $T_1$ level might be difficult. Therefore, the $T_1$ levels were also examined by quantum chemical calculations.

First, to estimate each $S_1$ level, a thin film (having a thickness of approximately 50 nm) was formed over a quartz substrate by a vacuum evaporation method as a thin film sample, and an absorption spectrum of the thin film sample was measured. The absorption spectrum was measured with an ultraviolet-visible spectrophotometer (V-550 manufactured by JASCO Corporation). Then, the absorption spectrum of quartz was subtracted from the measured spectrum of the sample. The $S_1$ level was estimated from the Tauc plot assuming a direct transition, which was constructed from the data of the absorption spectrum of the thin film.

Next, to estimate each $T_1$ level, phosphorescence measurement was performed. The substance used in the light-emitting element which is one embodiment of the present invention has very high fluorescence quantum yield, and accordingly, phosphorescence from a thin film sample including the material alone is very difficult to directly observe by a low-temperature PL method. Hence, the following method using a triplet sensitizer was employed to measure phosphorescence and estimate the $T_1$ level.

A co-evaporated film in which tris(2-phenylpyridinato-N,$C^{2'}$)iridium(III) (abbreviation: Ir(ppy)$_3$) was added as a triplet sensitizer to the material whose $T_1$ level was to be measured was formed. The film was subjected to a low-temperature PL method, and the $T_1$ level thereof was estimated from the measured phosphorescence spectrum. The measurement was performed using a PL microscope, LabRAM HR-PL, produced by HORIBA, Ltd., a He—Cd laser (325 nm) as excitation light, and a CCD detector at a measurement temperature of 10 K. The co-evaporation with Ir(ppy)$_3$ increases the probability of occurrence of intersystem crossing in the fluorescent material to be measured. Thus, phosphorescence from the fluorescent material can be measured, which is difficult to achieve when the co-evaporation is not employed.

For the measurement, each thin film was formed over a quartz substrate to a thickness of 50 nm and another quartz substrate was attached to the deposition surface in a nitrogen atmosphere.

Next, to verify the $T_1$ levels measured in the above method, quantum chemical calculations of the $T_1$ levels were performed.

The calculating method is as follows. Note that Gaussian 09 was used as the quantum chemistry computational program. A high performance computer (ICE X, manufactured by SGI Japan, Ltd) was used for the calculation.

The most stable structure in the lowest excited triplet state and the singlet ground state was calculated using the density functional theory. As a basis function, 6-311G (d,p) was used. As a functional, B3LYP was used. Then, the energy of the $T_1$ levels was calculated from an energy difference between the most stable structures in the singlet ground state and in the lowest excited triplet state.

The measurement results (actual values) and calculation results of the estimated $S_1$ levels and $T_1$ levels are shown in Table 5.

TABLE 5

| Abbreviation | Singlet excited energy level (actual value) | Triplet excited energy level (actual value) | Triplet excited energy level (calculated value) |
|---|---|---|---|
| 7CzPaBA | 2.98 eV | 1.97 eV | 1.92 eV |
| cgDBCzPA | 2.95 eV | 1.72 eV | 1.65 eV |
| 1,6mMemFLPAPrn | 2.68 eV | 1.84 eV | 1.73 eV |

The above results indicate a small difference between the values of the $T_1$ levels measured in the above method and those obtained by the quantum chemical calculations. Therefore, the values of the $T_1$ levels obtained in this example are sufficiently reliable.

Table 5 also shows that the $S_1$ level of 7CzPaBA, which has a benzo[a]anthracene skeleton, is an energy level high enough to be used as the host material 131 when 1,6mMemFLPAPm, which is a fluorescent material that emits blue light, is used.

Table 5 also shows that an energy difference between the $S_1$ level and $T_1$ level of each of 7CzPaBA and cgDBCzPA is 0.5 eV or more. If delayed fluorescence is caused by thermally activated delayed fluorescence due to reverse intersystem crossing from the triplet excited state to the singlet excited state, an energy difference between the $S_1$ level and the $T_1$ level is preferably 0.2 eV or less to efficiently cause the reverse intersystem crossing. Hence, the delayed fluorescence component of the material of the light-emitting layer in each of the above light-emitting elements fabricated in this example is attributed not to the thermally activated delayed fluorescence but to TTA.

A spectrum peak of fluorescence emitted from the thin film of 7CzPaBA was at 429 nm (2.89 eV) and a spectrum peak of fluorescence emitted from the thin film of cgDBCzPA was at 442 nm (2.81 eV). Accordingly, a difference in equivalent energy value between the peak wavelengths of the fluorescence and phosphorescence spectra of 7CzPaBA and cgDBCzPA was 0.5 eV or more. This also shows that the delayed fluorescence component of the material of the light-emitting layer in each of the above light-emitting elements fabricated in this example is attributed not to the thermally activated delayed fluorescence but to TTA. Note that the fluorescence spectra were measured with a PL-EL measurement apparatus (manufactured by Hamamatsu Photonics K.K.).

As described above, a light-emitting element with high emission efficiency and an emission spectrum peak in the blue wavelength range, in which a delayed fluorescence component due to TTA accounts for 20% or more, can be fabricated.

This application is based on Japanese Patent Application serial no. 2014-222441 filed with Japan Patent Office on Oct. 31, 2014, the entire contents of which are hereby incorporated by reference.

What is claimed is:

1. A benzoanthracene compound represented by a formula (G1),

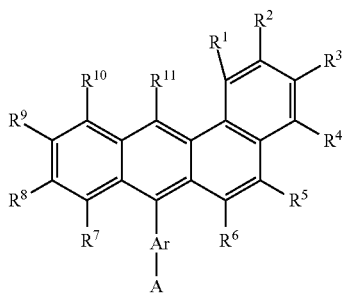

(G1)

wherein, in the formula (G1):
A represents a substituted or unsubstituted carbazolyl group;
$R^1$ to $R^{10}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms;
$R^{11}$ represents any of hydrogen, an alkyl group having 1 to 6 carbon atoms, and a cycloalkyl group having 3 to 6 carbon atoms;
Ar represents an arylene group having 6 to 13 carbon atoms;
wherein the arylene group represented by Ar includes one or more substituents; and
wherein each substituent of the arylene group is an alkyl group having 1 to 6 carbon atoms.

2. The benzoanthracene compound according to claim 1, wherein the substituents of the arylene group are bonded to each other to form a ring.

3. A light-emitting element comprising:
a pair of electrodes; and
an EL layer between the pair of electrodes,
wherein the EL layer comprises the benzoanthracene compound according to claim 1.

4. The light-emitting element according to claim 3, wherein the EL layer comprises a guest material capable of emitting fluorescence.

5. The light-emitting element according to claim 4, wherein the guest material is configured to exhibit an emission spectrum peak in a blue wavelength range.

6. The light-emitting element according to claim 4, wherein the guest material is capable of emitting delayed fluorescence.

7. The light-emitting element according to claim 4, wherein the guest material comprises a pyrene skeleton.

8. The benzoanthracene compound according to claim 1, wherein the benzoanthracene compound is represented by a formula (G2),

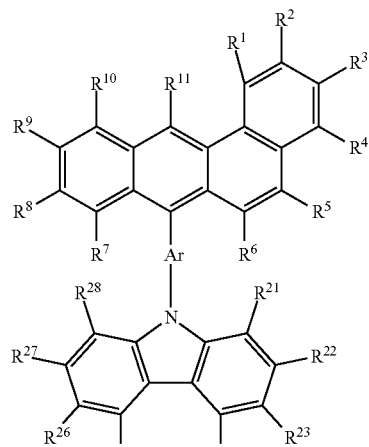

(G2)

and
wherein $R^{21}$ to $R^{28}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms.

9. The benzoanthracene compound according to claim 8, wherein Ar is an alkyl-substituted phenylene group.

10. The benzoanthracene compound according to claim 8, wherein Ar is an alkyl-substituted m-phenylene group.

11. The benzoanthracene compound according to claim 8, wherein the benzoanthracene compound is represented by a formula (G4),

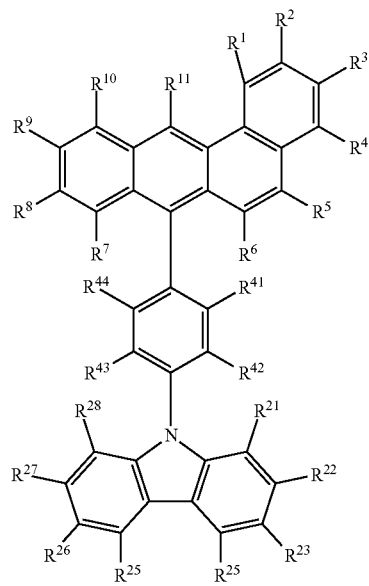

(G4)

wherein $R^{41}$ to $R^{44}$ each independently represent hydrogen or an alkyl group having 1 to 6 carbon atoms, and wherein at least one of $R^{41}$ to $R^{44}$ represents an alkyl group having 1 to 6 carbon atoms.

12. The benzoanthracene compound according to claim 1, wherein the benzoanthracene compound is represented by a formula (G3), (G3)

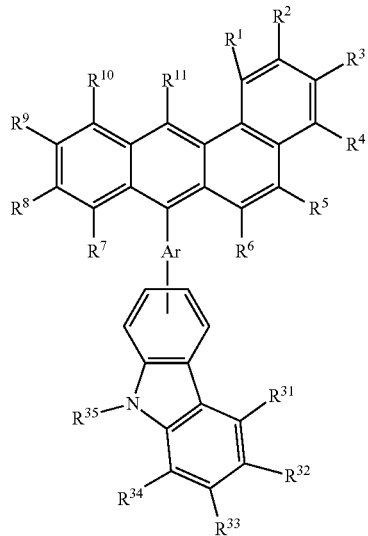

and
wherein $R^{31}$ to $R^{35}$ each independently represent any of hydrogen, an alkyl group having 1 to 6 carbon atoms, a cycloalkyl group having 3 to 6 carbon atoms, and a substituted or unsubstituted aryl group having 6 to 13 carbon atoms.

13. The benzoanthracene compound according to claim 12, wherein Ar is an alkyl-substituted phenylene group.

14. The benzoanthracene compound according to claim 12, wherein Ar is an alkyl-substituted m-phenylene group.

15. The benzoanthracene compound represented according to claim 12, wherein the benzoanthracene compound is represented by a formula (G5), (G5)

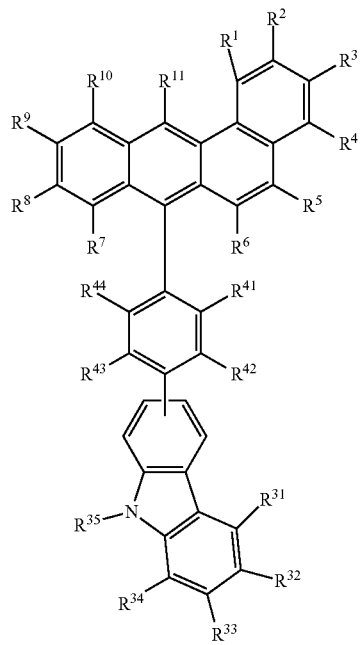

and
wherein $R^{41}$ to $R^{44}$ each independently represent hydrogen or an alkyl group having 1 to 6 carbon atoms, and wherein at least one of $R^{41}$ to $R^{44}$ represents an alkyl group having 1 to 6 carbon atoms.

* * * * *